US009018369B2

(12) United States Patent
Cook et al.

(10) Patent No.: US 9,018,369 B2
(45) Date of Patent: *Apr. 28, 2015

(54) DARK QUENCHERS FOR DONOR-ACCEPTOR ENERGY TRANSFER

(71) Applicant: Biosearch Technologies, Inc., Petaluma, CA (US)

(72) Inventors: Ronald M. Cook, Novato, CA (US); Matt Lyttle, San Rafael, CA (US); Daren Dick, San Rafael, CA (US)

(73) Assignee: Biosearch Technologies, Inc., Petaluma, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/158,521

(22) Filed: Jan. 17, 2014

(65) Prior Publication Data

US 2014/0323703 A1    Oct. 30, 2014

Related U.S. Application Data

(60) Continuation of application No. 12/765,844, filed on Apr. 22, 2010, now Pat. No. 8,633,307, which is a continuation of application No. 12/546,927, filed on Aug. 25, 2009, now Pat. No. 8,440,399, which is a continuation of application No. 11/437,991, filed on May 19, 2006, now Pat. No. 7,582,432, which is a division of application No. 11/192,705, filed on Jul. 29, 2005, now Pat. No. 7,109,312, which is a continuation of application No. 09/567,863, filed on May 9, 2000, now Pat. No. 7,019,129.

(51) Int. Cl.
| | |
|---|---|
| C07H 19/04 | (2006.01) |
| C07C 245/00 | (2006.01) |
| C07C 245/08 | (2006.01) |
| C07D 241/46 | (2006.01) |

(Continued)

(52) U.S. Cl.
CPC ............ *C07C 245/08* (2013.01); *C07B 2200/11* (2013.01); *C07D 241/46* (2013.01); *C07F 9/091* (2013.01); *C07F 9/2408* (2013.01); *C07H 21/00* (2013.01); *C09B 31/043* (2013.01); *C09B 56/00* (2013.01); *C12Q 1/6818* (2013.01); *C40B 40/00* (2013.01); *G01N 33/542* (2013.01); *G01N 33/582* (2013.01)

(58) Field of Classification Search
USPC ......................................... 536/26.6; 534/558
See application file for complete search history.

(56) References Cited

U.S. PATENT DOCUMENTS

| | | |
|---|---|---|
| 2,554,443 A | 5/1951 | Hayden |
| 2,653,109 A | 9/1953 | Switzer et al. |

(Continued)

FOREIGN PATENT DOCUMENTS

| | | |
|---|---|---|
| EP | 0008029 A1 | 2/1980 |
| EP | 0009191 A1 | 4/1980 |

(Continued)

OTHER PUBLICATIONS

Examination Report dated Nov. 19, 2013, received in European Application No. 01935256.6, which is related by priority to U.S. Appl. No. 09/567,863, 3 pages (Cook).

(Continued)

*Primary Examiner* — Jezia Riley
(74) *Attorney, Agent, or Firm* — Morgan, Lewis & Bockius LLP

(57) ABSTRACT

The present invention provides a family of dark quenchers, termed Black Hole Quenchers ("BHQs"), that are efficient quenchers of excited state energy but which are themselves substantially non-fluorescent. Also provided are methods of using the BHQs, probes incorporating the BHQs and methods of using the probes.

39 Claims, 9 Drawing Sheets

(51) Int. Cl.

| | | |
|---|---|---|
| C07F 9/09 | (2006.01) | |
| C07F 9/24 | (2006.01) | |
| C07H 21/00 | (2006.01) | |
| C09B 31/043 | (2006.01) | |
| C09B 56/00 | (2006.01) | |
| C12Q 1/68 | (2006.01) | |
| G01N 33/542 | (2006.01) | |
| G01N 33/58 | (2006.01) | |
| C40B 40/00 | (2006.01) | |

(56) References Cited

U.S. PATENT DOCUMENTS

| | | |
|---|---|---|
| 2,830,943 A | 4/1958 | Mackenzie |
| 2,945,849 A | 7/1960 | Kruckenberg et al. |
| 3,369,013 A | 2/1968 | Weaver et al. |
| 3,445,452 A | 5/1969 | Wallace et al. |
| 3,523,936 A | 8/1970 | Toji et al. |
| 3,709,870 A | 1/1973 | Wolfrum |
| 4,069,012 A | 1/1978 | Heinrich et al. |
| 4,313,872 A | 2/1982 | Heinrich et al. |
| 4,482,490 A | 11/1984 | Imahori et al. |
| 4,588,517 A | 5/1986 | Kaneko et al. |
| 4,623,716 A | 11/1986 | Stevenson et al. |
| 4,687,728 A | 8/1987 | Folkard et al. |
| 4,888,385 A | 12/1989 | Hudson |
| 4,965,349 A | 10/1990 | Woo et al. |
| 5,047,519 A | 9/1991 | Hobbs, Jr. et al. |
| 5,231,191 A | 7/1993 | Woo et al. |
| 5,312,738 A | 5/1994 | Hamill et al. |
| 5,384,411 A | 1/1995 | Robotti et al. |
| 5,401,847 A | 3/1995 | Glazer et al. |
| 5,484,908 A | 1/1996 | Froehler et al. |
| 5,612,221 A | 3/1997 | Simons et al. |
| 5,723,591 A | 3/1998 | Livak et al. |
| 5,736,626 A | 4/1998 | Mullah et al. |
| 5,874,587 A | 2/1999 | Donovan et al. |
| 5,925,517 A | 7/1999 | Tyagi et al. |
| 6,008,379 A | 12/1999 | Benson et al. |
| 6,037,130 A | 3/2000 | Tyagi et al. |
| 6,046,049 A | 4/2000 | Monia et al. |
| 6,103,476 A | 8/2000 | Tyagi et al. |
| 6,117,986 A | 9/2000 | Nardone et al. |
| 6,150,097 A | 11/2000 | Tyagi et al. |
| 6,288,221 B1 | 9/2001 | Grinstaff et al. |
| 6,291,203 B1 | 9/2001 | Poot et al. |
| 6,461,817 B1 | 10/2002 | Alland et al. |
| 6,531,581 B1 | 3/2003 | Nardone et al. |
| 6,653,473 B2 | 11/2003 | Reed et al. |
| 6,727,356 B1 | 4/2004 | Reed et al. |
| 6,790,945 B2 | 9/2004 | Lukhtanov et al. |
| 6,818,420 B2 | 11/2004 | Chou et al. |
| 7,019,129 B1 | 3/2006 | Cook et al. |
| 7,109,312 B2 | 9/2006 | Cook et al. |
| 7,160,996 B1 | 1/2007 | Cook |
| 7,160,997 B2 | 1/2007 | Chou et al. |
| 7,205,105 B2 | 4/2007 | Afonina et al. |
| 7,309,573 B2 | 12/2007 | Sorge |
| 7,385,043 B1 | 6/2008 | Kramer |
| 7,476,735 B2 | 1/2009 | Laikhter et al. |
| 7,485,442 B2 | 2/2009 | Afonina et al. |
| 7,582,432 B2 | 9/2009 | Cook et al. |
| 7,605,243 B2 | 10/2009 | Laikhter et al. |
| 7,645,872 B2 | 1/2010 | Laikhter et al. |
| 7,662,550 B1 | 2/2010 | Tyagi et al. |
| 7,662,942 B2 | 2/2010 | Reed et al. |
| 7,759,473 B2 | 7/2010 | Fujihara et al. |
| 7,803,936 B2 | 9/2010 | Laikhter et al. |
| 7,879,986 B2 | 2/2011 | Berry et al. |
| 7,897,736 B2 | 3/2011 | Reed et al. |
| 8,192,961 B2 | 6/2012 | Williams |
| 8,410,255 B2 | 4/2013 | Cook et al. |
| 8,440,399 B2 | 5/2013 | Cook et al. |
| 8,466,266 B2 | 6/2013 | Cook et al. |
| 8,633,307 B2 | 1/2014 | Cook et al. |
| 8,674,094 B2 | 3/2014 | Cook et al. |
| 8,946,404 B2 | 2/2015 | Cook et al. |
| 2002/0177695 A1 | 11/2002 | Grinstaff et al. |
| 2003/0165920 A1 | 9/2003 | Chou et al. |
| 2004/0005607 A1 | 1/2004 | Ewing et al. |
| 2005/0227254 A1 | 10/2005 | Lomholt et al. |
| 2005/0272088 A1 | 12/2005 | Cook et al. |
| 2006/0035262 A1 | 2/2006 | Cook et al. |
| 2006/0177857 A1 | 8/2006 | Berry et al. |
| 2006/0292589 A1 | 12/2006 | Reed et al. |
| 2007/0059752 A1 | 3/2007 | Cook |
| 2007/0154898 A1 | 7/2007 | Cook et al. |
| 2009/0259030 A1 | 10/2009 | Cook et al. |
| 2009/0275017 A1 | 11/2009 | Hirao et al. |
| 2010/0021922 A1 | 1/2010 | Cook et al. |
| 2010/0087634 A1 | 4/2010 | Berry et al. |
| 2010/0298554 A1 | 11/2010 | Laikhter et al. |
| 2011/0092679 A1 | 4/2011 | Cook et al. |
| 2011/0178280 A1 | 7/2011 | Cook et al. |
| 2011/0282041 A1 | 11/2011 | Cook et al. |
| 2014/0187763 A1 | 7/2014 | Cook et al. |
| 2014/0194611 A1 | 7/2014 | Cook et al. |
| 2014/0316118 A1 | 10/2014 | Cook et al. |

FOREIGN PATENT DOCUMENTS

| | | |
|---|---|---|
| EP | 0486477 A2 | 5/1992 |
| EP | 0601889 A2 | 6/1994 |
| EP | 0909823 A2 | 4/1999 |
| EP | 0876430 B1 | 8/2001 |
| FR | 1544951 | 11/1968 |
| FR | 2243438 A1 | 4/1975 |
| JP | H05-142600 A | 6/1993 |
| JP | H06-258676 A | 9/1994 |
| WO | WO 90/03446 A1 | 4/1990 |
| WO | WO 92/06102 A1 | 4/1992 |
| WO | WO 95/02848 A1 | 1/1995 |
| WO | WO 97/39008 A1 | 10/1997 |
| WO | WO 98/10096 A1 | 3/1998 |
| WO | WO 99/64431 A2 | 12/1999 |
| WO | WO 00/05411 A1 | 2/2000 |
| WO | WO 00/06778 A1 | 2/2000 |
| WO | WO 00/36152 A1 | 6/2000 |
| WO | WO 01/42505 A2 | 6/2001 |
| WO | WO 01/86001 A1 | 11/2001 |
| WO | WO 03/019145 A2 | 3/2003 |
| WO | WO 03/072051 A2 | 9/2003 |
| WO | WO 2006/002167 A2 | 1/2006 |
| WO | WO 2006/049297 A1 | 5/2006 |

OTHER PUBLICATIONS

Communication about intention to grant a European patent dated Mar. 5, 2014, received in European Application No. 09726629.0, which is related by priority to U.S. Appl. No. 12/416,901, 91 pages (Cook).

Examination Report Sep. 10, 2013, recieved in European Application no. 10184585.7, which is related by priority to U.S. Appl. No. 09/567,863, 3 pages (Cook).

Examination Report dated Apr. 9, 2014, received in European Application No. 10184585.7, which is related by priority to U.S. Appl. No. 09/567,863, 5 pages (Cook).

Examination Report dated Sep. 9, 2013, received in European Application No. 10184701.0, which is related by priority to U.S. Appl. No. 09/567,863, 5 pages (Cook).

Examination Report dated Mar. 13, 2014, received in European Application No. 10184701.0, which is related by priority to U.S. Appl. No. 09/567,863, 4 pages (Cook).

Communication about intention to grant a European patent dated Jun. 17, 2014, received in European Application No. 10184701.0, which is related by priority to U.S. Appl. No. 09/567,863, 83 pages (Cook).

European Search Report/Opinion dated Jun. 20, 2014, received in European Application No. 14152335.7, which is related by priority to U.S. Appl. No. 12/416,901, 6 pages (Cook).

Office Action dated Dec. 2, 2011, received in U.S. Appl. No. 12/765,844, 5 pages (Cook).

(56) References Cited

OTHER PUBLICATIONS

Office Action dated Jun. 28, 2012, received in U.S. Appl. No. 12/765,844, 5 pages (Cook).
Office Action dated Jan. 2, 2013, received in U.S. Appl. No. 12/765,844, 5 pages (Cook).
Notice of Allowance dated Sep. 17, 2013, received in U.S. Appl. No. 12/765,844, 6 pages (Cook).
Notice of Allowance dated Oct. 18, 2013, received in U.S. Appl. No. 13/193,517, 11 pages (Cook).
Office Action dated Sep. 24, 2014, received in U.S. Appl. No. 14,066,041, 4 pages (Cook).
Office Action dated Aug. 12, 2014, received in U.S. Appl. No. 14/318,932, 5 pages (Cook).
Notice of Allowance dated Sep. 22, 2014, receieved in U.S. Appl. No. 14,318,932, 5 pages (Cook).
Cardullo et al., "Detection of nucleic acid hybridization by nonradiative fluorescence resonance energy transfer," Proc. Natl. Acad. Sci. USA 1988, 85(23), 8790-8794.
Chou et al., "Use of dark-quenched FRET probes in real-time PCR," American Biotechnology Laboratory 2001, 19(8), 34.
Colour Index International, 3rd ed. (4th rev.); The Society of Dyers and Colourists: Bradford, West Yorkshire, England, 1992; p. v, Contents and p. viii.
Database CA [online], Chemical Abstracts Service, Columbus, Ohio, US; Blus, Kazimierz: "Synthesis and properties of disazo acid dyes"; retrieved from STN, Database accession No. 131:287725. [Source: Dyes and Pigments (1999), 43(3), 183-188.].
Database CA [online], Chemical Abstracts Service, Columbus, Ohio, US; Bumelis, V. et al: "Spectrophotometric study of the protonation of some azine dyes"; retrieved from STN, Database accession No. 85:125772. [Source: Nauchn. Konf. Khim.-Anal. Pribalt. Resp. B. SSR, [Tezisy Dokl.], 1st (1974), 62-8. Editor(s): Ramanauskas. E. Publisher: Vil'nyus. Gos. Univ., Vilnius, USSR.].
Database CA [online], Chemical Abstracts Service, Columbus, Ohio, US; Gonzalez-Gomez, C. et al: "Analytical method for determining color intensities based on Cherenkov radiation color quenching"; retrieved from STN, Database accession No. 98:209380. [Source: Journal of Radioanalytical Chemistry (1983), 77(1), 7-17.].
Database CA [online], Chemical Abstracts Service, Columbus, Ohio, US; Juarranz, A. et al: "Prediction of in situ fluorescence of histochemical reagents using a structure-staining correlation procedure"; retrieved from STN, Database accession No. 105:38550. [Source: Histochemistry (1986), 84(4-6), 426-31.].
Database CA [online], Chemical Abstracts Service, Columbus, Ohio, US; Po, Riccardo et al: "Synthesis and characterization of thermoplastic copolyesters containing copolymerized azoic dyes"; retrieved from STN, Database accession No. 122:215261. [Source: Polymers for Advanced Technologies (1995), 6(2), 63-8.].
Database CA [online], Chemical Abstracts Service, Columbus, Ohio, US; Szadowski, Jerzy et al: "Effect of dye solubility in polyglycol on its suitability for 'Cellestren' printing"; retrieved from STN, Database accession No. 110:136859. [Source: Przeglad Wlokienniczy (1988), 42(10), 436-9.].
De Clercq et al., "Nucleic Acid Related Compounds. 40. Synthesis and Biological Activities of 5-Alkynyluracil Nucleosides," J. Med. Chem. 1983, 26(5), 661-666.
Ediss et al., "A Broad Spectrum Colour Quencher for Liquid Scintillation Counting," Int. J. Appl. Radiat. Isot. 1982, 33(4), 296-297.
Endo et al., "Antitumor activity of phenazine derivatives against S 180 and C 63 in mice. I.," Chemical Abstracts 1966, 64, 1228e.
Endo et al., "Studies on Antitumor Activity of Phenazine Derivatives Against S 180 and C 63 in Mice (I)," Sci. Rep. Res. Inst. Tohoku Univ. C 1965, 12(1), 53-57.
Froehler et al., "Oligodeoxynucleotides Containing C-5 Propyne Analogs of 2'-Deoxyuridine and 2'-Deoxycytidine," Tetrahedron Lett. 1992, 33(37), 5307-5310.
Glen Research, "Catalog No. 10-5931-xx. Description: 5'-BHQ-1 Phosphoramidite," http://www.glenres.com/ProductFiles/10-5931.html, Nov. 4, 2011.
Glen Research, "Catalog No. 10-5941-xx. Description: BHQ-1-dT," http://www.glenres.com/ProductFiles/10-5941.html, Nov. 4, 2011.
Goodchild et al., "Structural Requirements of Olefinic 5-Substituted Deoxyuridines for Antiherpes Activity," J. Med. Chem. 1983, 26(9), 1252-1257.
Hodgkiss et al., "Fluorescent markers for hypoxic cells. A study of novel heterocyclic compounds that undergo bio-reductive binding," Biochem. Pharmacol. 1991, 41(4), 533-541.
Jäger et al., "A Versatile Toolbox for Variable DNA Functionalization at High Density," J. Am. Chem. Soc. 2005, 127(43), 15071-15082.
Johansson et al., "Intramolecular Dimers: A New Strategy to Fluorescence Quenching in Dual-Labeled Oligonucleotide. Probes," J. Am. Chem. Soc. 2002, 124(24), 6950-6956.
Juarranz et al., "Prediction of in situ fluorescence of histochemical reagents using a structure-staining correlation procedure," Histochemistry 1986, 84(4-6), 426-431.
Lukhtanov et al., "Novel DNA probes with low background and high hybridization-triggered fluorescence," Nucl. Acids. Res. 2007, 35(5), e30 (pp. 1-14).
Marras et al., "Efficiencies of fluorescence resonance energy transfer and contact-mediated quenching in oligonucleotide probes," Nucleic Acids Res. 2002, 30(21), e122 (pp. 1-8).
Marshall et al., "A technique for distinguishing between methylene violet and methylene violet Bernthsen," Stain Technol. 1975, 50(1), 51-53.
Marshall, P. N., "The composition of stains produced by the oxidation of Methylene Blue," Histochem. J. 1976, 8(4), 431-442.
May et al., "Synthesis and evaluation of a new non-fluorescent quencher in fluorogenic oligonucleotide probes for real-time PCR," Org. Biomol. Chem. 2005, 3(14), 2534-2542.
McKeen et al., "Synthesis of fluorophore and quencher monomers for use in Scorpion primers and nucleic acid structural probes," Org. Biomol. Chem. 2003, 1(13), 2267-2275.
Medina et al., "Improved thin-layer chromatographic detection of diethylstilbestrol and zeranol in plasma and tissues isolated with alumina and ion-exchange membrane columns in tandem," J. Chromatogr. 1993, 614(2), 315-323.
Medina et al., "Thin-layer chromatographic detection of zeranol and estradiol in fortified plasma and tissue extracts with Fast Corinth V," J. Chromatogr. 1992, 581(1), 119-128.
Moreira et al., "Effects of fluorescent dyes, quenchers, and dangling ends on DNA duplex stability," Biochem. Biophys. Res. Commun. 2005, 327(2), 473-484.
Nadeau et al., "Real-Time, Sequence-Specific Detection of Nucleic Acids during Strand Displacement Amplification," Anal. Biochem. 1999, 276(2), 177-187.
Nazarenko et al., "A closed tube format for amplification and detection of DNA based on energy transfer," Nucleic Acids Res. 1997, 25(12), 2516-2521.
Pelander et al., "Preparation of N-demethylated drug metabolites for analytical purposes using 1-chloroethyl chloroformate," Forensic Sci. Int. 1997, 85(3), 193-198.
Pelander et al., "Screening for cyanobacterial toxins in bloom and strain samples by thin layer chromatography," Water Research 1996, 30(6), 1464-1470.
Rahim et al., "5-Alkynyl Pyrimidine Nucleosides as Potent Selective Inhibitors of Varicella-Zoster Virus," Antivir. Chem. Chemother. 1992, 3(5), 293-297.
Sahlin et al., "Differentiation between attached and ingested immune complexes by a fluorescence quenching cytofluorometric assay," J. Immunol. Methods 1983, 60(1-2), 115-124.
Sawicki, E., "Physical Properties of the Aminoazobenzene Dyes. IX. Absorption Spectra in Alcohol and Acid Solution of Disazobenzene Dyes," J. Org. Chem. 1958, 23(4), 532-535.
Tsuda et al., "The comet assay in eight mouse organs: results with 24 azo compounds," Mutat. Res. 2000, 465(1-2), 11-26.
Tyagi et al., "Molecular beacons: Probes that Fluoresce upon Hybridization," Nat. Biotechnol. 1996, 14(3), 303-308.
Uzdensky, De la Cellule au Cerveau: le Cytosquelette, Communication Intra- et Inter-Cellulaire, le Systeme Nerveux Central, Les Houches, [Ecole d'Ete de Physique Theorique], 65th, Les Houches, Fr., Meeting Dates Jul. 8-26, 1996.

(56) References Cited

OTHER PUBLICATIONS

Valkó et al., "Application of Chromatographic Retention Data in an Investigation of a Quantitative Structure—Nucleotide Incorporation Rate Relationship," J. Chromatogr. 1990, 506, 35-44.
Valkó et al., "Correlation of Nucleotide Incorporation Rate and HPLC Retention Parameters of Substituted Nucleosides," J. Liq. Chromatogr. 1989, 12(11), 2103-2116.
Venkataraman, K., ed., The Chemistry of Synthetic Dyes, vol. I and II, Academic Press, New York, NY, 1952; pp. 658-667, 790-795.
Vennerstrom et al., "Antimalarial Dyes Revised: Xanthenes, Azines, Oxazines and Thiazines," Antimicrob. Agents Chemother. 1995, 39(12), 2671-2677.
Walton et al., "Evaluation of New Linkers and Synthetic Methods for Internal Modified Oligonucleotides," Bioconjugate Chem. 2002, 13(5), 1155-1158.
Wang, S.-S., "p-Alkoxybenzyl Alcohol Resin and p-Alkoxybenzyloxycarbonylhydrazide Resin for Solid Phase Synthesis of Protected Peptide Fragments," J. Am. Chem. Soc. 1973, 95(4), 1328-1333.
Wikipedia, "Phenazine," retrieved Mar. 21, 2012 from http://en.wikipedia.org/w/index.php?title=Phenazine&oldid=476096214.
Xie et al., "Synthesis and non-linear optical properties of four polyurethanes containing different chromophore groups," Eur. Polym. J. 2001, 37(3), 497-505. [Database CA [online], Chemical Abstracts Service, Columbus, Ohio, US; Xie, H.-Q. et al: "Synthesis and non-linear optical properties of four polyurethanes containing different chromophore groups"; retrieved from STN, Database accession No. 134:296174.].
Yang et al., "Evaluation of tetramethylrhodamine and black hole quencher 1 labeled probes and five commercial amplification mixes in TaqMan real-time RT-PCR assays for respiratory pathogens," J. Virol. Methods 2009, 162(1-2), 288-290.
Zollinger, H., Chapter 4 "Di- and Triarylmethine Dyes and their Aza Analogs" in Color Chemistry: Syntheses, Properties and Applications of Organic Dyes and Pigments, 2nd ed.; VCH Publishers: New York, NY, 1991; pp. 71-86.
European Search Report dated Jun. 30, 2003, received in European Application No. 01935256.6, which is related by priority to U.S. Appl. No. 09/567,863, 10 pages (Cook).
Examination Report dated Nov. 13, 2003, received in European Application No. 01935256.6, which is related by priority to U.S. Appl. No. 09/567,863, 7 pages (Cook).
Examination Report dated Mar. 3, 2005, received in European Application No. 01935256.6, which is related by priority to U.S. Appl. No. 09/567,863, 3 pages (Cook).
Examination Report dated Apr. 20, 2007, received in European Application No. 01935256.6, which is related by priority to U.S. Appl. No. 09/567,863, 7 pages (Cook).
Examination Report dated May 15, 2008, received in European Application No. 01935256.6, which is related by priority to U.S. Appl. No. 09/567,863, 8 pages (Cook).
Examination Report dated Dec. 29, 2009, received in European Application No. 01935256.6, which is related by priority to U.S. Appl. No. 09/567,863, 2 pages (Cook).
Examination Report dated Jan. 14, 2011, received in European Application No. 01935256.6, which is related by priority to U.S. Appl. No. 09/567,863, 4 pages (Cook).
Examination Report dated Oct. 22, 2012, received in European Application No. 01935256.6, which is related by priority to U.S. Appl. No. 09/567,863, 4 pages (Cook).
Examination Report dated Apr. 15, 2013, received in European Application No. 01935256.6, which is related by priority to U.S. Appl. No. 09/567,863, 3 pages (Cook).
European Search Report/Opinion dated Dec. 12, 2011, received in European Application No. 09726629.0, which is related by priority to U.S. Appl. No. 12/416,901, 4 pages (Cook).
Examination Report dated Sep. 11, 2012, received in European Application No. 09726629.0, which is related by priority to U.S. Appl. No. 12/416,901, 4 pages (Cook).
Communication about intention to grant a European patent dated Jun. 17, 2013, received in European Application No. 09726629.0, which is related by priority to U.S. Appl. No. 12/416,901, 90 pages (Cook).
European Search Report/Opinion dated May 9, 2011, received in European Application No. 10184585.7, which is related by priority to U.S. Appl. No. 09/567,863, 9 pages (Cook).
European Search Report/Opinion dated Mar. 28, 2011, received in European Application No. 10184701.0, which is related by priority to U.S. Appl. No. 09/567,863, 9 pages (Cook).
International Search Report dated Jul. 17, 2001, received in International Application No. PCT/US2001/015082, which is related by priority to U.S. Appl. No. 09/567,863, 2 pages (Cook).
Written Opinion dated May 9, 2002, received in International Application No. PCT/US2001/015082, which is related by priority to U.S. Appl. No. 09/567,863, 6 pages (Cook).
International Preliminary Examination Report dated Oct. 9, 2002, received in International Application No. PCT/US2001/015082, which is related by priority to U.S. Appl. No. 09/567,863, 6 pages (Cook).
International Search Report dated May 26, 2009, received in International Application No. PCT/US2009/039213, which is related by priority to U.S. Appl. No. 12/416,901, 2 pages (Cook).
Written Opinion dated May 26, 2009, received in International Application No. PCT/US2009/039213, which is related by priority to U.S. Appl. No. 12/416,901, 5 pages (Cook).
International Preliminary Report on Patentability dated Oct. 14, 2010, received in International Application No. PCT/US2009/039213, which is related by priority to U.S. Appl. No. 12/416,901, 6 pages (Cook).
Office Action dated Apr. 25, 2001, received in U.S. Appl. No. 09/567,863, 3 pages (Cook).
Office Action dated Dec. 9, 2002, received in U.S. Appl. No. 09/567,863, 9 pages (Cook).
Office Action dated Oct. 1, 2003, received in U.S. Appl. No. 09/567,863, 6 pages (Cook).
Office Action dated Sep. 23, 2004, received in U.S. Appl. No. 09/567,863, 5 pages (Cook).
Office Action dated Mar. 1, 2005, received in U.S. Appl. No. 09/567,863, 4 pages (Cook).
Notice of Allowance dated May 16, 2005, received in U.S. Appl. No. 09/567,863, 6 pages (Cook).
Office Action dated Nov. 21, 2005, received in U.S. Appl. No. 11/192,705, 4 pages (Cook).
Office Action dated Feb. 17, 2006, received in U.S. Appl. No. 11/192,705, 4 pages (Cook).
Notice of Allowance dated Apr. 13, 2006, received in U.S. Appl. No. 11/192,705, 4 pages (Cook).
Office Action dated Jul. 10, 2007, received in U.S. Appl. No. 11/226,852, 4 pages (Cook).
Office Action dated Apr. 24, 2008, received in U.S. Appl. No. 11/226,852, 6 pages (Cook).
Office Action dated Jun. 17, 2009, received in U.S. Appl. No. 11/226,852, 5 pages (Cook).
Notice of Allowance dated Jan. 15, 2010, received in U.S. Appl. No. 11/226,852, 4 pages (Cook).
Office Action dated Apr. 29, 2013, received in U.S. Appl. No. 11/226,852, 6 pages (Cook).
Office Action dated May 1, 2008, received in U.S. Appl. No. 11/437,991, 5 pages (Cook).
Notice of Allowance dated May 1, 2009, received in U.S. Appl. No. 11/437,991, 4 pages (Cook).
Office Action dated Oct. 18, 2011, received in U.S. Appl. No. 12/416,901, 13 pages (Cook).
Notice of Allowance dated Feb. 19, 2013, received in U.S. Appl. No. 12/416,901, 6 pages (Cook).
Office Action dated Nov. 12, 2009, received in U.S. Appl. No. 12,546,927, 4 pages (Cook).
Office Action dated Feb. 15, 2011, received in U.S. Appl. No. 12,546,927, 6 pages (Cook).
Notice of Allowance dated May 20, 2011, received in U.S. Appl. No. 12,546,927, 4 pages (Cook).
Notice of Allowance dated Sep. 28, 2011, received in U.S. Appl. No. 12/546,927, 5 pages (Cook).

(56) References Cited

OTHER PUBLICATIONS

Notice of Allowance dated Jan. 14, 2013, received in U.S. Appl. No. 12/546,927, 5 pages (Cook).
Notice of Allowance dated Nov. 10, 2011, received in U.S. Appl. No. 12/852,387, 5 pages (Cook).
Notice of Allowance dated Jul. 9, 2012, received in U.S. Appl. No. 12/852,387, 5 pages (Cook).
Notice of Allowance dated Dec. 4, 2012, received in U.S. Appl. No. 12/852,387, 5 pages (Cook).
Office Action dated Oct. 12, 2011, received in U.S. Appl. No. 12/193,517, 9 pages (Cook).
Office Action dated Sep. 17, 2012, received in U.S. Appl. No. 12/193,517, 15 pages (Cook).
Office Action dated May 24, 2013, received in U.S. Appl. No. 12,193,517, 11 pages (Cook).
Reexam—Non-Final Action dated Nov. 21, 2011, received in U.S. Reexamination No. 95/001,710, 89 pages (Cook).
Action Closing Prosecution dated Sep. 4, 2012, received in U.S. Reexamination No. 95/001,710, 26 pages (Cook).
Right of Appeal Notice dated Feb. 13, 2013, received in U.S. Reexamination No. 95/001,710, 22 pages (Cook).
Notice of Intent to Issue a Reexam Certificatie dated May 14, 2013, received in U.S. Reexamination No. 95/001,710, 4 pages (Cook).
Reexamination Certificate dated May 31, 2013, received in U.S. Reexamination No. 95,001,710, 2 pages (Cook).
Reexam—Non-Final Action dated Nov. 21, 2011, received in U.S. Reexamination No. 95,001,711, 36 pages (Cook).
Action Closing Prosecution dated Jun. 22, 2012, received in U.S. Reexamination No. 95/001,711, 25 pages (Cook).
Right of Appeal Notice dated Feb. 13, 2013, received in U.S. Reexamination No. 95/001,711, 22 pages (Cook).
Notice of Intent to Issue a Reexam Certificate dated Apr. 9, 2013, received in U.S. Reexamination No. 95/001,711, 4 pages (Cook).
Reexamination Certificate dated May 10, 2013, received in U.S. Reexamination No. 95/001,711, 2 pages (Cook).
Reexam—Non-Final Action dated Nov. 21, 2001, received in U.S. Reexamination No. 95/001,712, 48 pages (Cook).
Action Closing Prosecution dated Jun. 22, 2012, received in U.S. Reexamination No. 95/001,712, 36 pages (Cook).
Right of Appeal Notice dated Sep. 27, 2012, received in U.S. Reexamination No. 95/001,712, 37 pages (Cook).
Notice of INtenet to Issue a Reexam Certificate dated Feb. 8, 2013, received in U.S. Reexamination No. 95/001,712, 5 pages (Cook).
Reexamination Certificate dated Feb. 22, 2013, received in U.S. Reexamination No. 95/001,712, 2 pages (Cook).
Spitzer, J. C. and Wolff, D. A., "The Reaction of Cationic Dyes with Disodium Cromoglycate," J. Heterocycl. Chem. 1979, 16(5), 845-847.
Examination Report dated Feb. 5, 2015, received in European Application No. 01935256.6, which is related by priority to U.S. Appl. No. 09/567,863, 6 pages (Cook).
Office Action dated Feb. 24, 2015, received in U.S. Appl. No. 14/066,041, 4 pages (Cook).

DARK QUENCHERS FOR DONOR-ACCEPTOR ENERGY TRANSFER

CROSS-REFERENCES TO RELATED APPLICATIONS

This application is a continuation of U.S. patent application Ser. No. 12/765,844, filed Apr. 22, 2010, which is a continuation of U.S. patent application Ser. No. 12/546,927, filed Aug. 25, 2009, now U.S. Pat. No. 8,440,399, which is a continuation of U.S. patent application Ser. No. 11/437,991, filed May 19, 2006, now U.S. Pat. No. 7,582,432, which is a divisional of U.S. patent application Ser. No. 11/192,705, filed Jul. 29, 2005, now U.S. Pat. No. 7,109,312, which is a continuation of U.S. patent application Ser. No. 09/567,863, filed May 9, 2000, now U.S. Pat. No. 7,019,129, all of which are incorporated herein by reference in their entirety for all purposes.

STATEMENT OF GOVERNMENT RIGHTS

This invention was made with government support under Grant Nos. IR43GM60848-01 and 2R44GM60848-02 awarded by the National Institutes of Health. The government has certain rights in the invention.

BACKGROUND OF THE INVENTION

There is a continuous and expanding need for rapid, highly specific methods of detecting and quantifying chemical, biochemical and biological substances as analytes in research and diagnostic mixtures. Of particular value are methods for measuring small quantities of nucleic acids, peptides, pharmaceuticals, metabolites, microorganisms and other materials of diagnostic value. Examples of such materials include narcotics and poisons, drugs administered for therapeutic purposes, hormones, pathogenic microorganisms and viruses, antibodies, and enzymes and nucleic acids, particularly those implicated in disease states.

The presence of a particular analyte can often be determined by binding methods that exploit the high degree of specificity, which characterizes many biochemical and biological systems. Frequently used methods are based on, for example, antigen-antibody systems, nucleic acid hybridization techniques, and protein-ligand systems. In these methods, the existence of a complex of diagnostic value is typically indicated by the presence or absence of an observable "label" which has been attached to one or more of the interacting materials. The specific labeling method chosen often dictates the usefulness and versatility of a particular system for detecting an analyte of interest. Preferred labels are inexpensive, safe, and capable of being attached efficiently to a wide variety of chemical, biochemical, and biological materials without significantly altering the important binding characteristics of those materials. The label should give a highly characteristic signal, and should be rarely, and preferably never, found in nature. The label should be stable and detectable in aqueous systems over periods of time ranging up to months. Detection of the label is preferably rapid, sensitive, and reproducible without the need for expensive, specialized facilities or the need for special precautions to protect personnel. Quantification of the label is preferably relatively independent of variables such as temperature and the composition of the mixture to be assayed.

A wide variety of labels have been developed, each with particular advantages and disadvantages. For example, radioactive labels are quite versatile, and can be detected at very low concentrations, such labels are, however, expensive, hazardous, and their use requires sophisticated equipment and trained personnel. Thus, there is wide interest in non-radioactive labels, particularly in labels that are observable by spectrophotometric, spin resonance, and luminescence techniques, and reactive materials, such as enzymes that produce such molecules.

Labels that are detectable using fluorescence spectroscopy are of particular interest, because of the large number of such labels that are known in the art. Moreover, the literature is replete with syntheses of fluorescent labels that are derivatized to allow their facile attachment to other molecules, and many such fluorescent labels are commercially available.

In addition to being directly detected, many fluorescent labels operate to quench the fluorescence of an adjacent second fluorescent label. Because of its dependence on the distance and the magnitude of the interaction between the quencher and the fluorophore, the quenching of a fluorescent species provides a sensitive probe of molecular conformation and binding, or other, interactions. An excellent example of the use of fluorescent reporter quencher pairs is found in the detection and analysis of nucleic acids.

Fluorescent nucleic acid probes are important tools for genetic analysis, in both genomic research and development, and in clinical medicine. As information from the Human Genome Project accumulates, the level of genetic interrogation mediated by fluorescent probes will expand enormously. One particularly useful class of fluorescent probes includes self-quenching probes, also known as fluorescence energy transfer probes, or FET probes. The design of different probes using this motif may vary in detail. In an exemplary FET probe, both a fluorophore and a quencher are tethered to nucleic acid. The probe is configured such that the fluorophore is proximate to the quencher and the probe produces a signal only as a result of its hybridization to an intended target. Despite the limited availability of FET probes, techniques incorporating their use are rapidly displacing alternative methods.

Probes containing a fluorophore-quencher pair have been developed for nucleic acid hybridization assays where the probe forms a hairpin structure, i.e., where the probe hybridizes to itself to form a loop such that the quencher molecule is brought into proximity with the reporter molecule in the absence of a complementary nucleic acid sequence to prevent the formation of the hairpin structure (see, for example, WO 90/03446; European Patent Application No. 0 601 889 A2). When a complementary target sequence is present, hybridization of the probe to the complementary target sequence disrupts the hairpin structure and causes the probe to adopt a conformation where the quencher molecule is no longer close enough to the reporter molecule to quench the reporter molecule. As a result, the probes provide an increased fluorescence signal when hybridized to a target sequence than when they are unhybridized Assays have also been developed for detecting a selected nucleic acid sequence and for identifying the presence of a hairpin structure using two separate probes, one containing a reporter molecule and the other a quencher molecule (see, Meringue, et al., *Nucleic Acids Research*, 22: 920-928 (1994)). In these assays, the fluorescence signal of the reporter molecule decreases when hybridized to the target sequence due to the quencher molecule being brought into proximity with the reporter molecule.

One particularly important application for probes including a reporter-quencher molecule pair is their use in nucleic acid amplification reactions, such as polymerase chain reactions (PCR), to detect the presence and amplification of a target nucleic acid sequence. In general, nucleic acid amplification techniques have opened broad new approaches to genetic testing and DNA analysis (see, for example, Arnheim et al. *Ann. Rev. Biochem.,* 61: 131-156 (1992)). PCR, in particular, has become a research tool of major importance with applications in, for example, cloning, analysis of genetic expression, DNA sequencing, genetic mapping and drug discovery (see, Arnheim et al., supra; Gilliland et al., *Proc. Natl. Acad. Sci. USA,* 87: 2725-2729 (1990); Bevan et al., *PCR Methods and Applications,* 1: 222-228 (1992); Green et al., *PCR Methods and Applications,* 1: 77-90 (1991); Blackwell et al., *Science,* 250: 1104-1110 (1990)).

Commonly used methods for detecting nucleic acid amplification products require that the amplified product be separated from unreacted primers. This is typically achieved either through the use of gel electrophoresis, which separates the amplification product from the primers on the basis of a size differential, or through the immobilization of the product, allowing free primer to be washed away. However, a number of methods for monitoring the amplification process without prior separation of primer have been described. All of them are based on FET, and none of them detect the amplified product directly. Instead, the methods detect some event related to amplification. For that reason, they are accompanied by problems of high background, and are not quantitative, as discussed below.

One method, described in Wang et al. (U.S. Pat. No. 5,348,853; and *Anal. Chem.,* 67: 1197-1203 (1995)), uses an energy transfer system in which energy transfer occurs between two fluorophores on the probe. In this method, detection of the amplified molecule takes place in the amplification reaction vessel, without the need for a separation step. This method, however, does not detect the amplified product, but instead detects the dissociation of primer from the "energy-sink" nucleic acid. Thus, this method is dependent on detection of a decrease in emissions; a significant portion of labeled primer must be utilized in order to achieve a reliable difference between the signals before and after the reaction.

A second method detecting an amplification product without prior separation of primer and product is the 5'-nuclease PCR assay (also referred to as the TaqMan™ assay) (Holland et al., *Proc. Natl. Acad. Sci. USA,* 88: 7276-7280 (1991); Lee et al., *Nucleic Acids Res.,* 21: 3761-3766 (1993)). This assay detects the accumulation of a specific PCR product by hybridization and cleavage of a doubly labeled fluorogenic probe (the "TaqMan" probe) during the amplification reaction. The fluorogenic probe consists of an nucleic acid labeled with both a fluorescent reporter dye and a quencher dye. During PCR, this probe is cleaved by the 5'-exonuclease activity of DNA polymerase if, and only if, it hybridizes to the segment being amplified. Cleavage of the probe generates an increase in the fluorescence intensity of the reporter dye.

In the TaqMan assay, the donor and quencher are preferably located on the 3'- and 5'-ends of the probe, because the requirement that 5'-3' hydrolysis be performed between the fluorophore and quencher may be met only when these two moieties are not too close to each other (Lyamichev et al., *Science,* 260:778-783 (1993)). This requirement is a serious drawback of the assay as the efficiency of energy transfer decreases with the inverse sixth power of the distance between the reporter and quencher. Thus, if the quencher is not close enough to the reporter to achieve the most efficient quenching the background emissions from the probe can be quite high.

Yet another method of detecting amplification products that relies on the use of energy transfer is the "beacon probe" method described by Tyagi et al. (*Nature Biotech.,* 14:303-309 (1996)) which is also the subject of U.S. Pat. No. 5,312,728 to Lizardi et al. This method employs nucleic acid hybridization probes that can form hairpin structures. On one end of the hybridization probe (either the 5'- or 3'-end) there is a donor fluorophore, and on the other end, an acceptor moiety. In this method, the acceptor moiety is a quencher, absorbing energy from the donor. Thus when the beacon is in the open conformation, the fluorescence of the donor fluorophore is detectable, whereas when the beacon is in hairpin (closed) conformation, the fluorescence of the donor fluorophore is quenched. When employed in PCR, the molecular beacon probe, which hybridizes to one of the strands of the PCR product, is in "open conformation," and fluorescence is detected, while those that remain unhybridized will not fluoresce. As a result, the amount of fluorescence will increase as the amount of PCR product increases, and thus can be used as a measure of the progress of the PCR.

Certain limitations impede the application and use of FET probes, or result in assays that are less sensitive than they could be. Foremost among these limitations is the presence of background fluorescence attributable to the emission of the quencher, giving the probe a higher fluorescent noise background than is desirable. An approach that has been utilized to ameliorate this limitation is the use of a quencher that is not a fluorophore ("dark quenchers"), such as derivatives of 4-(dimethylamino)azobenzene (DABCYL). DABCYL is useful as a quenching agent for a limited group of fluorophores with whose emission characteristics, the absorption characteristics of DABCYL overlap. The limited absorption range of DABCYL restricts the utility of this compound by allowing the use of a limited number of fluorophores in conjunction with DABCYL. Because relatively few fluorophores can be used with DABCYL in FET pairs, multiplex applications, where it is desired to use two or more fluorophores with clearly resolved fluorescence emission spectra are difficult to design using this quencher.

In view of the limitations of presently available dark quenchers and probes, such as FET probes constructed with these quenchers, there exists in the art a need for improved quenchers that can be incorporated into probes for detecting analytes rapidly, sensitively, reliably and quantitatively. Ideal quenchers would be have little to no fluorescent quenching signal, and be easily and inexpensively prepared. Moreover, a series of quenchers having similar physical properties, but distinct spectral properties would be particularly advantageous. Quite surprisingly, the present invention provides such quenchers, probes incorporating these quenchers and methods for using the quenchers and probes.

SUMMARY OF THE INVENTION

The present invention provides a family of quenchers of excited state energy that are substantially non-fluorescent, termed "Black Hole Quenchers" ("BHQs"). The quenchers of the invention remedy many of the deficiencies of currently utilized dark quenchers, probes assembled using these quenchers and methods using such quenchers and probes. The present invention provides a class of dark quenchers that are functionalized to allow their rapid attachment to probe components using techniques well known in the art, or modifications of such techniques that are well within the abilities of those of skill in the art. Moreover, the present invention provides a class of dark quenchers that can be engineered to have a desired light absorption profile. The provision of this class of dark quenchers represents a substantial improvement in the design of probes incorporating dark quenchers and methods using such probes.

Many of the nucleic acid probes presently used rely on an interaction between the fluorophore and the quencher in order to minimize the fluorescence of the probe in the absence of its hybridization to a complementary nucleic acid. The interaction between the fluorophore and the quencher is typically brought about by using a nucleic acid probe sequence that forms a secondary structure (e.g., hairpin, loop, etc.). Requiring that a probe adopt a secondary structure significantly complicates the design of the probe and greatly restricts the nucleic acid sequences that can be used as components of the probes. In contrast, nucleic acid probes using BHQs of the present invention are found to facilitate the interaction between the quencher and the fluorophore without requiring concomitant formation of nucleic acid secondary structure, thereby allowing a much greater diversity of nucleic acid sequences to be used as components of fluorescent probes.

Moreover, by varying the number and identity of the members of the conjugated system of the BHQs, the spectral properties (e.g., absorbance) of a BHQ can be "tuned" to match the spectral characteristics (e.g., emission) of one or more fluorophores. For example, as the BHQs of the present invention can be selected to have a broad range of absorbance maxima, these quenchers are uniquely suited for use in multiplexing applications. Furthermore, the ability to select a BHQ having a particular spectral characteristic allows the use of BHQs in multiplexing applications using one or more distinct fluorophore in combination with one or more distinct BHQ, thereby expanding the choices of donor-acceptor pairs that can be incorporated into probes.

Thus, in a first aspect, the present invention provides a quencher of excited state energy having a structure comprising at least three radicals selected from substituted or unsubstituted aryl, substituted or unsubstituted heteroaryl and combinations thereof, wherein at least two of the residues are covalently linked via an exocyclic diazo bond, the quencher further comprising a reactive functional group providing a locus for conjugation of the quencher to a carrier molecule.

In a second aspect, the present invention provides a quencher of excited state energy having a structure according to Formula I:

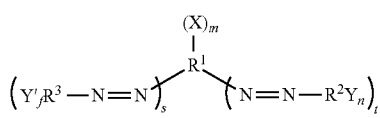

(I)

wherein $R^1$, $R^2$ and $R^3$ are members independently selected from substituted or unsubstituted aryl, substituted or unsubstituted heteroaryl and substituted or unsubstituted unsaturated alkyl, with the proviso that at least two of $R^1$, $R^2$ and $R^3$ are members selected from substituted or unsubstituted aryl, and substituted or unsubstituted heteroaryl. X, Y and Y' are members independently selected from reactive functional groups; f is a number selected from 0 to 4, inclusive, such that when (f×s) is greater than 1, the Y' groups are the same or different; m is a number selected from 1 to 4, inclusive, such that when m is greater than 1, the X groups are the same or different; n is a number from 0 to 6, inclusive, such that when (n×t) is greater than 1, the Y groups are the same or different; s is a number from 0 to 6, inclusive, such that when s is greater than 1 the $R^3$ groups are the same or different; and t is a number from 1 to 6, inclusive, such that when t is greater than 1 the $R^2$ groups are the same or different, and when t is 1 and s is 0, a member selected from $R^1$, $R^2$ and combinations thereof is a member selected from substituted or unsubstituted polycyclic aryl and substituted or unsubstituted polycyclic heteroaryl groups.

In a third aspect, the present invention provides a quencher of excited state energy having a structure according to Formula II:

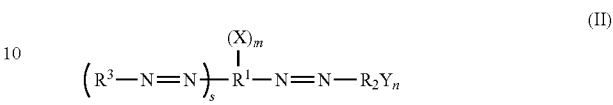

(II)

in which, X and Y are members independently selected from reactive functional groups; m is a number selected from 1 to 5, inclusive, such that when m is greater than 1, the X groups are the same or different; n is a number selected from 0 to 5, inclusive, such that when m is greater than 1, the Y groups are the same or different; s is a number selected from 1 to 5, inclusive, such that when s is greater than 1, the $R^3$ groups are the same or different. $R^1$, $R^2$, and $R^3$ are members independently selected from substituted or unsubstituted aryl, substituted or unsubstituted heteroaryl, and substituted or unsubstituted unsaturated alkyl, with the proviso that at least two of $R^1$, $R^2$ and $R^3$ are members independently selected from substituted or unsubstituted aryl, and substituted or unsubstituted heteroaryl.

In each of the above-described aspects of the invention X is preferably a member selected from —COOH, —OH and —NR'R", wherein R' and R" are members independently selected from the group consisting of H and substituted or unsubstituted alkyl groups.

In a fourth aspect, the invention provides compounds having a structure according to Formula IV:

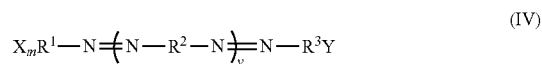

(IV)

in which, X and Y are members independently selected from reactive functional groups; m is a number selected from 0 to 4, inclusive, such that when m is greater than 1, the X groups are the same or different; c is a number selected from 0 to 4, inclusive, such that when c is greater than 1, the $R^3$ groups are the same or different; v is a number from 1 to 10, inclusive, more preferably from 1 to 6, inclusive and more preferably still between 2 and 4, inclusive. When v is greater than 1, the $R^2$ groups are the same or different. $R^1$, $R^2$, and $R^3$ are members independently selected from substituted or unsubstituted aryl, substituted or unsubstituted heteroaryl and substituted or unsubstituted unsaturated alkyl, with the proviso that at least two of $R^1$, $R^2$ and $R^3$ are members selected from substituted or unsubstituted aryl, substituted or unsubstituted heteroaryl and combinations thereof.

In a fifth aspect, the invention provides compounds having a structure according to Formula V:

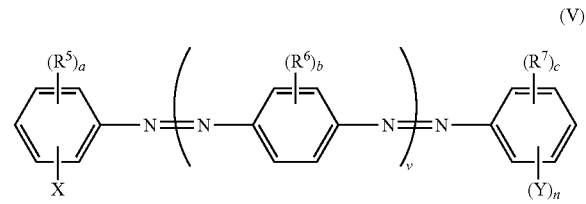

(V)

wherein, $R^5$, $R^6$ and $R^7$ are members independently selected from —NR'R", substituted or unsubstituted aryl, nitro, substituted or unsubstituted $C_1$-$C_6$ alkyl, and substituted or unsubstituted $C_1$-$C_6$ alkoxy, wherein R' and R" are independently selected from H and substituted or unsubstituted $C_1$-$C_6$ alkyl. X and Y are independently selected from the group consisting of reactive functional groups; m is a number from 1 to 2, inclusive, such that when m is 2, the X groups are the same or different; n is a number from 0 to 1, inclusive; a is a number from 0 to 4, inclusive, such that when a is greater than 1, the $R^5$ groups are the same or different; b is a number from 0 to 4, inclusive, such that when (v×b) is greater than 1, the $R^6$ groups are the same or different; c is a number from 0 to 5, inclusive, such that when c is greater than 1, the $R^7$ groups are the same or different; and v is a number from 1 to 10, inclusive, such that when v is greater than 1, the value of b on each of the b phenyl rings is the same or different.

In a sixth aspect, the present invention provides a quencher of excited state energy having a structure, which is a member selected from:

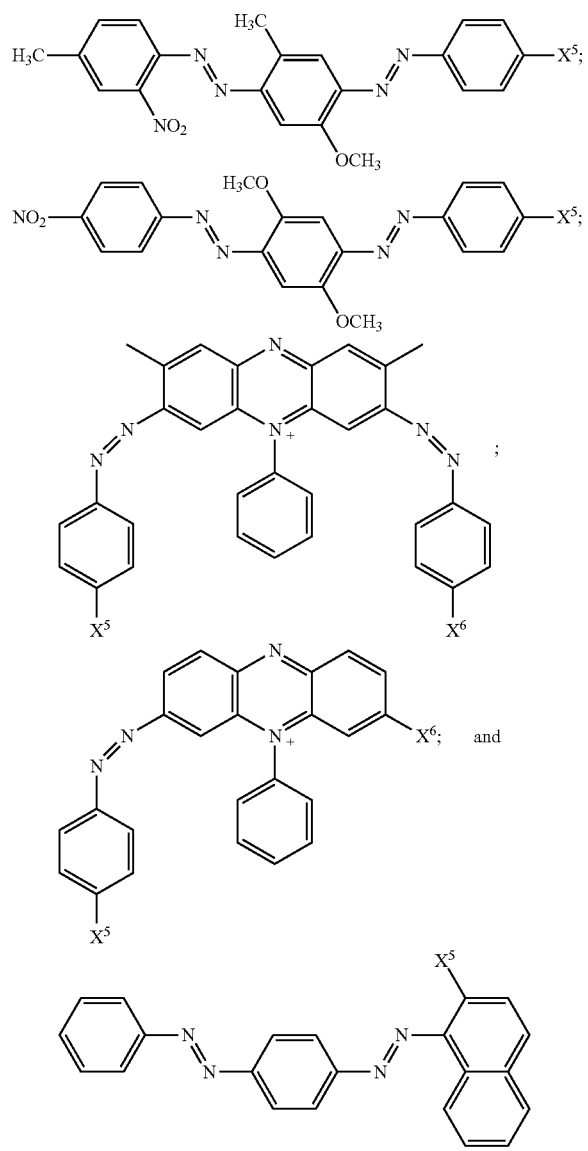

wherein, $X^5$ and $X^6$ are members independently selected from H, substituted or unsubstituted $C_1$-$C_6$ alkyl, —OR', —COOR', —NR'R", —SH, —OP($OX^3$)N($X^4$)$_2$, in which R' and R" are members independently selected from the group consisting of H, and alkyl or substituted alkyl, with the proviso that at least one of $X^5$ and $X^6$ is a reactive functional group. $X^3$ and $X^4$ are members independently selected from CN, and substituted or unsubstituted $C_1$-$C_6$ alkyl.

In an seventh aspect, the present invention provides a method for determining whether a sample contains an enzyme. The method includes: (a) contacting the sample with a peptide construct that includes a fluorophore; (b) exciting said fluorophore; and (c) determining a fluorescence property of said sample, wherein the presence of said enzyme in said sample results in a change in said fluorescence property.

Preferred peptide constructs include: i) a fluorophore; ii) a quencher comprising at least three residues selected from aryl, substituted aryl, heteroaryl, substituted heteroaryl and combinations thereof, wherein at least two of the residues are covalently linked via an exocyclic diazo bond; and iii) a cleavage recognition site for the enzyme. Moreover, the peptide is preferably in a conformation allowing donor-acceptor energy transfer between the fluorophore and the quencher when the fluorophore is excited.

In another aspect, the invention provides a method for determining whether a compound alters an activity of an enzyme. Preferred embodiments of this aspect of the invention include the steps recited in connection with the above-recited aspect of the invention and further include a step (c) determining a fluorescence property of the sample, wherein said activity of said enzyme in said sample results in a change in the fluorescence property.

In an ninth aspect, the present invention provides a method for detecting a nucleic acid target sequence. The method includes: (a) contacting the target sequence with a detector nucleic acid; (b) hybridizing the target binding sequence to the target sequence, thereby altering the conformation of the detector nucleic acid, causing a change in a fluorescence parameter; and (c) detecting the change in the fluorescence parameter, thereby detecting the nucleic acid target sequence.

In the methods described herein, unless otherwise noted, a preferred detector nucleic acid includes a single-stranded target binding sequence. The binding sequence has linked thereto: i) a fluorophore; and ii) a BHQ of the invention.

In an tenth aspect, the invention provides a method for detecting amplification of a target sequence. The method includes the use of an amplification reaction including the following steps: (a) hybridizing the target sequence and a detector nucleic acid. The detector nucleic acid includes a single-stranded target binding sequence and an intramolecularly associated secondary structure 5' to the target binding sequence. At least a portion of the detector sequence forms a single stranded tail which is available for hybridization to the target sequence; (b) extending the hybridized detector nucleic acid on the target sequence with a polymerase to produce a detector nucleic acid extension product and separating the detector nucleic acid extension product from the target sequence; (c) hybridizing a primer to the detector nucleic acid extension product and extending the primer with the polymerase, thereby linearizing the intramolecularly associated secondary structure and producing a change in a fluorescence parameter; and (d) detecting the change in the fluorescence parameter, thereby detecting the target sequence.

In an eleventh aspect, the invention provides a method of ascertaining whether a first nucleic acid and a second nucleic acid hybridize. In this method, the first nucleic acid includes a BHQ according to the invention. The method includes: (a)

contacting the first nucleic acid with the second nucleic acid; (b) detecting an alteration in a fluorescent property of a member selected from the first nucleic acid, the second nucleic acid and a combination thereof, thereby ascertaining whether the hybridization occurs.

In a twelfth aspect, the present invention provides a method for determining whether a sample contains an enzyme. The method comprises: (a) contacting the sample with a peptide construct; (b) exciting the fluorophore; and (c) determining a fluorescence property of the sample, wherein the presence of the enzyme in the sample results in a change in the fluorescence property.

Peptide constructs useful in practicing the invention include those with the following features: i) a fluorophore; ii) a BHQ of the invention; and iii) a cleavage recognition site for the enzyme.

In an thirteenth aspect, the invention provides methods of determining the amount of activity of an enzyme in a sample from an organism. The method includes: (a) contacting a sample comprising the enzyme and the compound with a peptide construct comprising (b) exciting the fluorophore; and (c) determining a fluorescence property of the sample, wherein the activity of the enzyme in the sample results in a change in the fluorescence property. Peptide constructs useful in this aspect of the invention are substantially similar to those described immediately above.

In a fourteenth aspect, the invention provides a microarray comprising a quencher of excited state energy having a structure comprising at least three residues selected from aryl, substituted aryl, heteroaryl, substituted heteroaryl and combinations thereof, wherein at least two of the residues are covalently linked via an exocyclic diazo bond. The quencher is conjugated directly to a solid support or to a carrier molecule attached to the solid support.

In a fifteenth aspect, the invention provides a method of probing a microarray for the presence of a compound. The method includes: (a) contacting the microarray with a probe interacting with the compound. Preferred probes include a quencher of excited state energy having a structure comprising at least three residues selected from aryl, substituted aryl, heteroaryl, substituted heteroaryl and combinations thereof, wherein at least two of the residues are covalently linked via an exocyclic diazo bond; and (b) detecting a difference in a fluorescence property of a member selected from the probe, the compound and combinations thereof, thereby ascertaining the presence of the compound.

In a sixteenth aspect, the present invention provides a mixture including at least a first carrier molecule and a second carrier molecule. The first carrier molecule has covalently bound thereto a first quencher of excited state energy having a structure comprising at least three residues selected from aryl, substituted aryl, heteroaryl, substituted heteroaryl and combinations thereof, wherein at least two of said residues are covalently linked via an exocyclic diazo bond. The second carrier molecule has covalently bound thereto a second quencher of excited state energy having a structure comprising at least three residues selected from aryl, substituted aryl, heteroaryl, substituted heteroaryl and combinations thereof, wherein at least two of said residues are covalently linked via an exocyclic diazo bond.

Additional objects and advantages of the present invention will be apparent to those of skill in the art upon examination of the detailed description that follows.

BRIEF DESCRIPTION OF THE DRAWINGS

FIG. 7A is an overlay plot of the absorbance spectra of BH1 and the emission spectra of three commonly used fluorophores FAM, TET and JOE;

FIG. 7B is an overlay plot of the absorbance spectra of DABCYL and the emission spectra of three commonly used fluorophores FAM, TET and JOE.

DETAILED DESCRIPTION OF THE INVENTION AND THE PREFERRED EMBODIMENTS

Abbreviations

Figure 1:
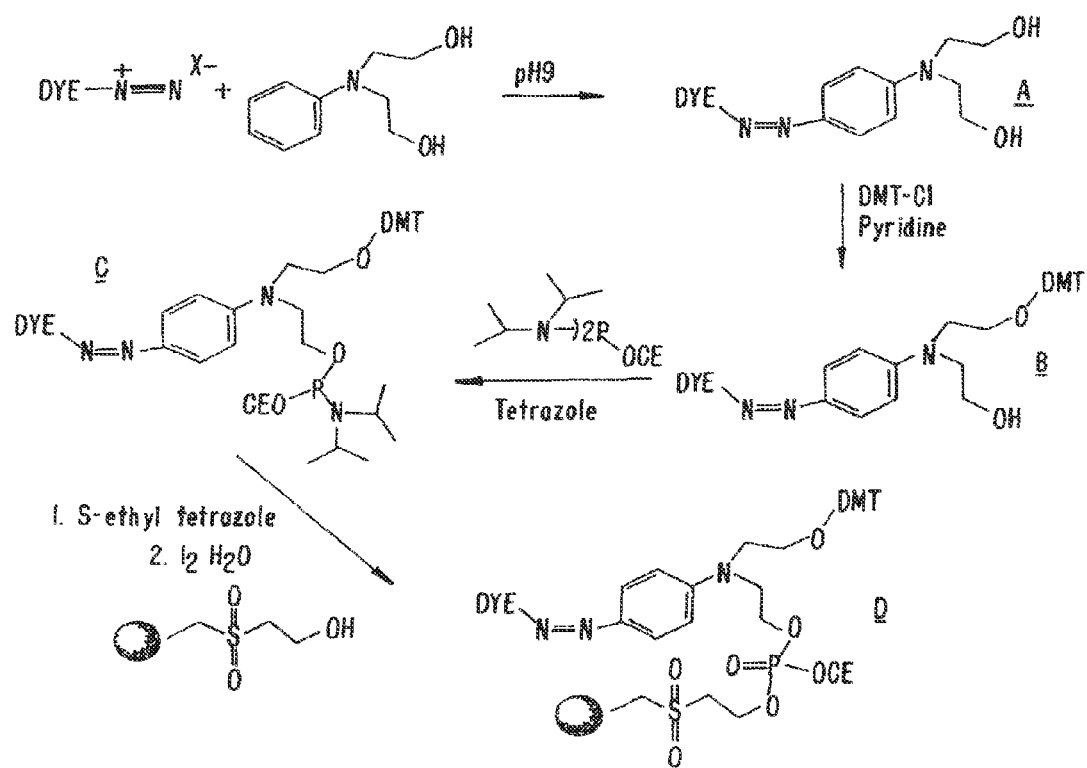
FIG. 1 is an exemplary synthetic scheme for preparing a BHQ of the invention.

"BHQ," as used herein, refers to "Black Hole Quenchers."
"FET," as used herein, refers to "Fluorescence Energy Transfer." "FRET," as used herein, refers to "Fluorescence Resonance Energy Transfer." These terms are used herein to refer to both radiative and non-radiative energy transfer processes. For example, processes in which a photon is emitted and those involving long range electron transfer are included within these terms. Throughout this specification, both of these phenomena are subsumed under the general term "donor-acceptor energy transfer."

DEFINITIONS

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization described below are those well known and commonly employed in the art. Standard techniques are used for nucleic acid and peptide synthesis. Generally, enzymatic reactions and purification steps are performed according to the manufacturer's specifications. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document. The nomenclature used herein and the laboratory procedures in analytical chemistry, and organic synthetic described below are those well known and commonly employed in the art. Standard techniques, or modifications thereof, are used for chemical syntheses and chemical analyses.

"Analyte", as used herein means any compound or molecule of interest for which a diagnostic test is performed. An analyte can be, for example, a protein, peptide, carbohydrate, polysaccharide, glycoprotein, hormone, receptor, antigen, antibody, virus, substrate, metabolite, transition state analog, cofactor, inhibitor, drug, dye, nutrient, growth factor, etc., without limitation.

As used herein, "energy transfer" refers to the process by which the excited state energy of an excited group is altered by a modifying group, such as a quencher. If the excited state energy-modifying group is a quenching group, then the fluorescence emission from the fluorescent group is attenuated (quenched). Energy transfer can occur through fluorescence resonance energy transfer, or through direct energy transfer. The exact energy transfer mechanisms in these two cases are different. It is to be understood that any reference to energy transfer in the instant application encompasses all of these mechanistically-distinct phenomena.

As used herein, "energy transfer pair" refers to any two molecules that participate in energy transfer. Typically, one of the molecules acts as a fluorescent group, and the other acts as a fluorescence-modifying group. The preferred energy transfer pair of the instant invention comprises a fluorescent group and a quenching group of the invention. There is no limitation on the identity of the individual members of the energy transfer pair in this application. All that is required is that the spectroscopic properties of the energy transfer pair as a whole change in some measurable way if the distance between the individual members is altered by some critical amount. "Energy transfer pair" is used to refer to a group of molecules that form a complex within which energy transfer occurs. Such complexes may include, for example, two fluorescent groups, which may be different from one another and one quenching group, two quenching groups and one fluorescent group, or multiple fluorescent groups and multiple quenching groups. In cases where there are multiple fluorescent groups and/or multiple quenching groups, the individual groups may be different from one another.

As used herein, "fluorescence-modifying group" refers to a molecule of the invention that can alter in any way the fluorescence emission from a fluorescent group. A fluorescence-modifying group generally accomplishes this through an energy transfer mechanism. Depending on the identity of the fluorescence-modifying group, the fluorescence emission can undergo a number of alterations, including, but not limited to, attenuation, complete quenching, enhancement, a shift in wavelength, a shift in polarity, and a change in fluorescence lifetime. One example of a fluorescence-modifying group is a quenching group.

As used herein, "quenching group" refers to any fluorescence-modifying group of the invention that can attenuate at least partly the light emitted by a fluorescent group. This attenuation is referred to herein as "quenching". Hence, illumination of the fluorescent group in the presence of the quenching group leads to an emission signal that is less intense than expected, or even completely absent. Quenching typically occurs through energy transfer between the fluorescent group and the quenching group.

As used herein, "nucleic acid" means DNA, RNA, single-stranded, double-stranded, or more highly aggregated hybridization motifs, and any chemical modifications thereof. Modifications include, but are not limited to, those providing chemical groups that incorporate additional charge, polarizability, hydrogen bonding, electrostatic interaction, and fluxionality to the nucleic acid ligand bases or to the nucleic acid ligand as a whole. Such modifications include, but are not limited to, peptide nucleic acids (PNAs), phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases, isocytidine and isoguanidine and the like. Nucleic acids can also include non-natural bases, such as, for example, nitroindole. Modifications can also include 3' and 5' modifications such as capping with a BHQ, a fluorophore or another moiety.

"Peptide" refers to a polymer in which the monomers are amino acids and are joined together through amide bonds, alternatively referred to as a polypeptide. When the amino acids are α-amino acids, either the L-optical isomer or the D-optical isomer can be used. Additionally, unnatural amino acids, for example, β-alanine, phenylglycine and homoarginine are also included. Commonly encountered amino acids that are not gene-encoded may also be used in the present invention. All of the amino acids used in the present invention may be either the D- or L-isomer. The L-isomers are generally preferred. In addition, other peptidomimetics are also useful in the present invention. For a general review, see, Spatola, A. F., in CHEMISTRY AND BIOCHEMISTRY OF AMINO ACIDS, PEPTIDES AND PROTEINS, B. Weinstein, eds., Marcel Dekker, New York, p. 267 (1983).

"Bioactive species," refers to molecules that, when administered to an organism, affect that organism. Exemplary bioactive species include pharmaceuticals, pesticides, herbicides, growth regulators and the like. Bioactive species encompasses small molecules (i.e., approximately <1000 daltons), oligomers, polymers and the like. Also included are nucleic acids and their analogues, peptides and their analogues and the like.

The term "alkyl" is used herein to refer to a branched or unbranched, saturated or unsaturated, monovalent and divalent hydrocarbon radical, generally having from about 1-30 carbons and preferably, from 4-20 carbons and more preferably from 6-18 carbons. When the alkyl group has from 1-6 carbon atoms, it is referred to as a "lower alkyl." Suitable alkyl radicals include, for example, structures containing one or more methylene, methine and/or methyne groups. Branched structures have a branching motif similar to i-propyl, t-butyl, i-butyl, 2-ethylpropyl, etc. As used herein, the term encompasses "substituted alkyls," and "cyclic alkyl."

"Substituted alkyl" refers to alkyl as just described including one or more substituents such as, for example, lower alkyl, aryl, acyl, halogen (i.e., alkylhalos, e.g., $CF_3$), hydroxy, amino, alkoxy, alkylamino, acylamino, thioamido, acyloxy, aryloxy, aryloxyalkyl, mercapto, thia, aza, oxo, both saturated and unsaturated cyclic hydrocarbons, heterocycles and the like. These groups may be attached to any carbon or substituent of the alkyl moiety. Additionally, these groups may be pendent from, or integral to, the alkyl chain.

The term "aryl" is used herein to refer to an aromatic substituent, which may be a single aromatic ring or multiple aromatic rings which are fused together, linked covalently, or linked to a common group such as a diazo, methylene or ethylene moiety. The common linking group may also be a carbonyl as in benzophenone. The aromatic ring(s) may include phenyl, naphthyl, biphenyl, diphenylmethyl and benzophenone among others. The term "aryl" encompasses "arylalkyl" and "substituted aryl."

"Substituted aryl" refers to aryl as just described including one or more functional groups such as lower alkyl, acyl, halogen, alkylhalos (e.g. $CF_3$), hydroxy, amino, alkoxy, alkylamino, acylamino, acyloxy, phenoxy, mercapto and both saturated and unsaturated cyclic hydrocarbons which are fused to the aromatic ring(s), linked covalently or linked to a common group such as a diazo, methylene or ethylene moiety. The linking group may also be a carbonyl such as in cyclohexyl phenyl ketone. The term "substituted aryl" encompasses "substituted arylalkyl."

The term "arylalkyl" is used herein to refer to a subset of "aryl" in which the aryl group is attached to another group by an alkyl group as defined herein.

"Substituted arylalkyl" defines a subset of "substituted aryl" wherein the substituted aryl group is attached to another group by an alkyl group as defined herein.

The term "acyl" is used to describe a ketone substituent, $C(O)R$, where R is alkyl or substituted alkyl, aryl or substituted aryl as defined herein.

The term "halogen" is used herein to refer to fluorine, bromine, chlorine and iodine atoms.

The term "hydroxy" is used herein to refer to the group —OH.

The term "amino" is used to —NRR', wherein R and R' are independently H, alkyl, aryl or substituted analogues thereof "Amino" encompasses "alkylamino" denoting secondary and tertiary amines and "acylamino" describing the group $RC(O)NR'$.

The term "alkoxy" is used herein to refer to the —OR group, where R is alkyl, or a substituted analogue thereof. Suitable alkoxy radicals include, for example, methoxy, ethoxy, t-butoxy, etc.

As used herein, the term "aryloxy" denotes aromatic groups that are linked to another group directly through an oxygen atom. This term encompasses "substituted aryloxy" moieties in which the aromatic group is substituted as described above for "substituted aryl." Exemplary aryloxy moieties include phenoxy, substituted phenoxy, benzyloxy, phenethyloxy, etc.

As used herein "aryloxyalkyl" defines aromatic groups attached, through an oxygen atom to an alkyl group, as defined herein. The term "aryloxyalkyl" encompasses "substituted aryloxyalkyl" moieties in which the aromatic group is substituted as described for "substituted aryl."

As used herein, the term "mercapto" defines moieties of the general structure —S—R wherein R is H, alkyl, aryl or heterocyclic as described herein.

The term "saturated cyclic hydrocarbon" denotes groups such as the cyclopropyl, cyclobutyl, cyclopentyl, etc., and substituted analogues of these structures. These cyclic hydrocarbons can be single- or multi-ring structures.

The term "unsaturated cyclic hydrocarbon" is used to describe a monovalent non-aromatic group with at least one double bond, such as cyclopentene, cyclohexene, etc. and substituted analogues thereof. These cyclic hydrocarbons can be single- or multi-ring structures.

The term "heteroaryl" as used herein refers to aromatic rings in which one or more carbon atoms of the aromatic ring(s) are replaced by a heteroatom such as nitrogen, oxygen or sulfur. Heteroaryl refers to structures that may be a single aromatic ring, multiple aromatic ring(s), or one or more aromatic rings coupled to one or more non-aromatic ring(s). In structures having multiple rings, the rings can be fused together, linked covalently, or linked to a common group such as a diazo, methylene or ethylene moiety. The common linking group may also be a carbonyl as in phenyl pyridyl ketone. As used herein, rings such as thiophene, pyridine, isoxazole, phthalimide, pyrazole, indole, furan, etc. or benzo-fused analogues of these rings are defined by the term "heteroaryl."

"Heteroarylalkyl" defines a subset of "heteroaryl" wherein an alkyl group, as defined herein, links the heteroaryl group to another group.

"Substituted heteroaryl" refers to heteroaryl as just described wherein the heteroaryl nucleus is substituted with one or more functional groups such as lower alkyl, acyl, halogen, alkylhalos (e.g. $CF_3$), hydroxy, amino, alkoxy, alkylamino, acylamino, acyloxy, mercapto, etc. Thus, substituted analogues of heteroaromatic rings such as thiophene, pyridine, isoxazole, phthalimide, pyrazole, indole, furan, etc. or benzo-fused analogues of these rings are defined by the term "substituted heteroaryl."

"Substituted heteroarylalkyl" refers to a subset of "substituted heteroaryl" as described above in which an alkyl group, as defined herein, links the heteroaryl group to another group.

The term "heterocyclic" is used herein to describe a monovalent saturated or unsaturated non-aromatic group having a single ring or multiple condensed rings from 1-12 carbon atoms and from 1-4 heteroatoms selected from nitrogen, sulfur or oxygen within the ring. Such heterocycles are, for example, tetrahydrofuran, morpholine, piperidine, pyrrolidine, etc.

The term "substituted heterocyclic" as used herein describes a subset of "heterocyclic" wherein the heterocycle nucleus is substituted with one or more functional groups such as lower alkyl, acyl, halogen, alkylhalos (e.g. $CF_3$), hydroxy, amino, alkoxy, alkylamino, acylamino, acyloxy, mercapto, etc.

The term "heterocyclicalkyl" defines a subset of "heterocyclic" wherein an alkyl group, as defined herein, links the heterocyclic group to another group.

Introduction

The present invention provides a class of fluorescence modifiers, particularly quenchers, of excited state energy. The compounds of the invention absorb excited state energy from a reporter fluorophore, but are themselves substantially non-fluorescent. The fluorophore transferring the excited state energy to the quenchers of the invention will generally be a label that is attached to an analyte or a species that interacts with, and allows detection and/or quantification of the analyte.

Fluorescent labels have the advantage of requiring few precautions in handling, and being amenable to high-throughput visualization techniques (optical analysis including digitization of the image for analysis in an integrated system comprising a computer). Preferred labels are typically characterized by one or more of the following: high sensitivity, high stability, low background, low environmental sensitivity and high specificity in labeling. Many fluorescent labels are commercially available from the SIGMA chemical company (Saint Louis, Mo.), Molecular Probes (Eugene, Oreg.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), and Applied Biosystems (Foster City, Calif.), as well as many other commercial sources known to one of skill. Furthermore, those of skill in the art will recognize how to select an appropriate fluorophore for a particular application and, if it not readily available commercially, will be able to synthesize the necessary fluorophore de novo or synthetically modify commercially available fluorescent compounds to arrive at the desired fluorescent label.

In addition to small molecule fluorophores, naturally occurring fluorescent proteins and engineered analogues of such proteins are useful in the present invention. Such proteins include, for example, green fluorescent proteins of cnidarians (Ward et al., *Photochem. Photobiol.* 35:803-808 (1982); Levine et al., *Comp. Biochem. Physiol.,* 72B:77-85 (1982)), yellow fluorescent protein from *Vibrio fischeri* strain (Baldwin et al., *Biochemistry* 29:5509-15 (1990)), Peridinin-chlorophyll from the dinoflagellate *Symbiodinium* sp. (Morris et al., *Plant Molecular Biology* 24:673:77 (1994)), phycobiliproteins from marine cyanobacteria, such as *Synechococcus*, e.g., phycoerythrin and phycocyanin (Wilbanks et al., *J. Biol. Chem.* 268:1226-35 (1993)), and the like.

The compounds, probes and methods discussed in the following sections are generally representative of the compositions of the invention and the methods in which such compositions can be used. The following discussion is intended as illustrative of selected aspects and embodiments of the present invention and it should not be interpreted as limiting the scope of the present invention.

Black Hole Quenchers

The present invention provides a family of dark quenchers that are referred to herein as "Black Hole Quenchers™" ("BHQ"s). The quenchers of the invention include conjugated π-bonded systems that are preferably azo-linked aromatic species.

In a first aspect, the present invention provides a quencher of excited state energy having a structure comprising at least three radicals selected from substituted or unsubstituted aryl, substituted or unsubstituted heteroaryl and combinations thereof, wherein at least two of the residues are covalently linked via an exocyclic diazo bond, the quencher further comprising a reactive functional group providing a locus for conjugation of the quencher to a carrier molecule. Although the quenchers can be used in their free unbound form, it is generally preferred that they be tethered to another species, thus, preferred quenchers further comprise a reactive functional group that provides a locus for conjugation of the quencher to a carrier molecule.

In another preferred embodiment, the BHQs of the invention described herein have substantially no native fluorescence, particularly near their absorbance maxima or near the absorbance maxima of fluorophores used in conjunction with the BHQs. The BHQs will preferably have an absorbance maximum of from about 400 nm to about 760 nm, and more preferably, of from about 500 nm to about 600 nm.

In a second aspect, the present invention provides a quencher of excited state energy having a structure according to Formula I:

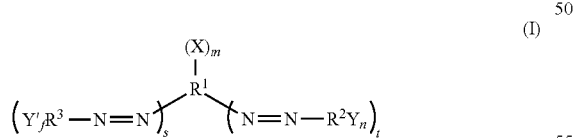

wherein $R^1$, $R^2$ and $R^3$ are members independently selected from substituted or unsubstituted aryl, substituted or unsubstituted heteroaryl and substituted or unsubstituted unsaturated alkyl, with the proviso that at least two of $R^1$, $R^2$ and $R^3$ are members selected from substituted or unsubstituted aryl, and substituted or unsubstituted heteroaryl. X, Y and Y' are members independently selected from reactive functional groups; f is a number selected from 0 to 4, inclusive, such that when (f×s) is greater than 1, the Y' groups are the same or different; m is a number selected from 1 to 4, inclusive, such that when m is greater than 1, the X groups are the same or different; n is a number from 0 to 6, inclusive, such that when (n×t) is greater than 1, the Y groups are the same or different; s is a number from 0 to 6, inclusive, such that when s is greater than 1 the $R^3$ groups are the same or different; and t is a number from 1 to 6, inclusive, such that when t is greater than 1 the $R^2$ groups are the same or different, and when t is 1 and s is 0, a member selected from $R^1$, $R^2$ and combinations thereof is a member selected from substituted or unsubstituted polycyclic aryl and substituted or unsubstituted polycyclic heteroaryl groups.

In a third aspect, the present invention provides a quencher of excited state energy having a structure according to Formula II:

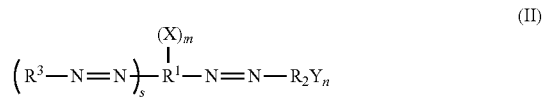

in which, X and Y are members independently selected from reactive functional groups; m is a number selected from 1 to 5, inclusive, such that when m is greater than 1, the X groups are the same or different; n is a number selected from 0 to 5, inclusive, such that when m is greater than 1, the Y groups are the same or different; s is a number selected from 1 to 5, inclusive, such that when s is greater than 1, the $R^3$ groups are the same or different. $R^1$, $R^2$, and $R^3$ are members independently selected from substituted or unsubstituted aryl, substituted or unsubstituted heteroaryl, and substituted or unsubstituted unsaturated alkyl, with the proviso that at least two of $R^1$, $R^2$ and $R^3$ are members independently selected from substituted or unsubstituted aryl, and substituted or unsubstituted heteroaryl.

In a preferred embodiment, m is 1; n is 0; c is 1; and $R^1$, $R^2$ and $R^3$ are members independently selected from aryl and substituted aryl.

In a preferred embodiment of each of the above-described aspects of the invention, $R^1$, $R^2$ and $R^3$ are members independently selected from aryl and aryl substituted with a member selected from amino, amino derivatives, nitro, $C_1$-$C_6$ alkyl, $C_1$-$C_6$ alkoxy and combinations thereof, and still more preferably, $R^1$ includes a structure according to Formula III:

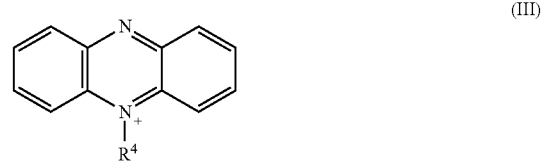

wherein $R^4$ is a member selected from alkyl, substituted alkyl, aryl, substituted aryl, heteroaryl and substituted heteroaryl.

In a fourth aspect, the invention provides compounds having a structure according to Formula IV:

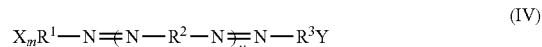

in which, X and Y are members independently selected from reactive functional groups; m is a number selected from 0 to 4, inclusive, such that when m is greater than 1, the X groups are the same or different; c is a number selected from 0 to 4, inclusive, such that when c is greater than 1, the $R^3$ groups are the same or different; v is a number from 1 to 10, inclusive, more preferably from 1 to 6, inclusive and more preferably still between 2 and 4, inclusive. When v is greater than one the $R^2$ groups are the same or different. $R^1$, $R^2$, and $R^3$ are members independently selected from substituted or unsubstituted aryl, substituted or unsubstituted heteroaryl and substituted or unsubstituted unsaturated alkyl, with the proviso that at least two of $R^1$, $R^2$ and $R^3$ are members selected from substituted or unsubstituted aryl, substituted or unsubstituted heteroaryl and combinations thereof.

In a fifth aspect, the invention provides compounds having a structure according to Formula V:

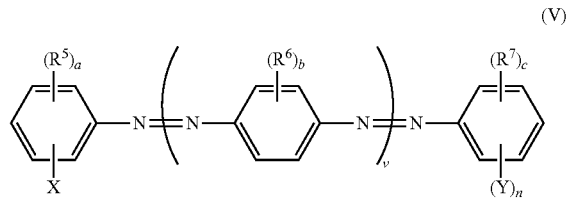

(V)

wherein, $R^5$, $R^6$ and $R^2$ are members independently selected from —NR'R", substituted or unsubstituted aryl, nitro, substituted or unsubstituted $C_1$-$C_6$ alkyl, and substituted or unsubstituted $C_1$-$C_6$ alkoxy, wherein R' and R" are independently selected from H and substituted or unsubstituted $C_1$-$C_6$ alkyl. X and Y are independently selected from the group consisting of reactive functional groups; n is a number from 0 to 1, inclusive; a is a number from 0 to 4, inclusive, such that when a is greater than 1, the $R^5$ groups are the same or different; b is a number from 0 to 4, inclusive, such that when (v×b) is greater than 1, the $R^6$ groups are the same or different; c is a number from 0 to 5, inclusive, such that when c is greater than 1, the $R^7$ groups are the same or different; and v is a number from 1 to 10, inclusive, such that when v is greater than 1, the value of b on each of the v phenyl rings is the same or different.

In a preferred embodiment, the present invention provides a quencher of excited state energy having a structure according to Formula VI:

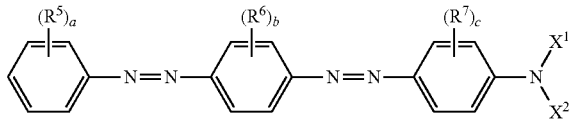

(VI)

wherein, $R^5$, $R^6$ and $R^7$ are members independently selected from amine, alkyl amine, substituted or unsubstituted aryl, nitro, substituted or unsubstituted $C_1$-$C_6$ alkyl, substituted or unsubstituted $C_1$-$C_6$ alkoxy; a is a number between 0 and 5, inclusive, such that when a is greater than 1, the $R^5$ groups are the same or different; b is a number between 0 and 4, inclusive, such that when b is greater than 1, the $R^6$ groups are the same or different; c is a number between 0 and 4, inclusive, such that when c is greater than 1, the $R^7$ groups are the same or different; and $X^1$ and $X^2$ are members independently selected from $C_1$-$C_6$ alkyl or $C_1$-$C_6$ substituted alkyl, —OH, —COOH, —NR'R", —SH, —OP($OX^3$)(NR'R"), in which R' and R" are members independently selected from the group consisting of H, and alkyl or substituted alkyl.

In a sixth aspect, the present invention provides a quencher of excited state energy having a structure, which is a member selected from:

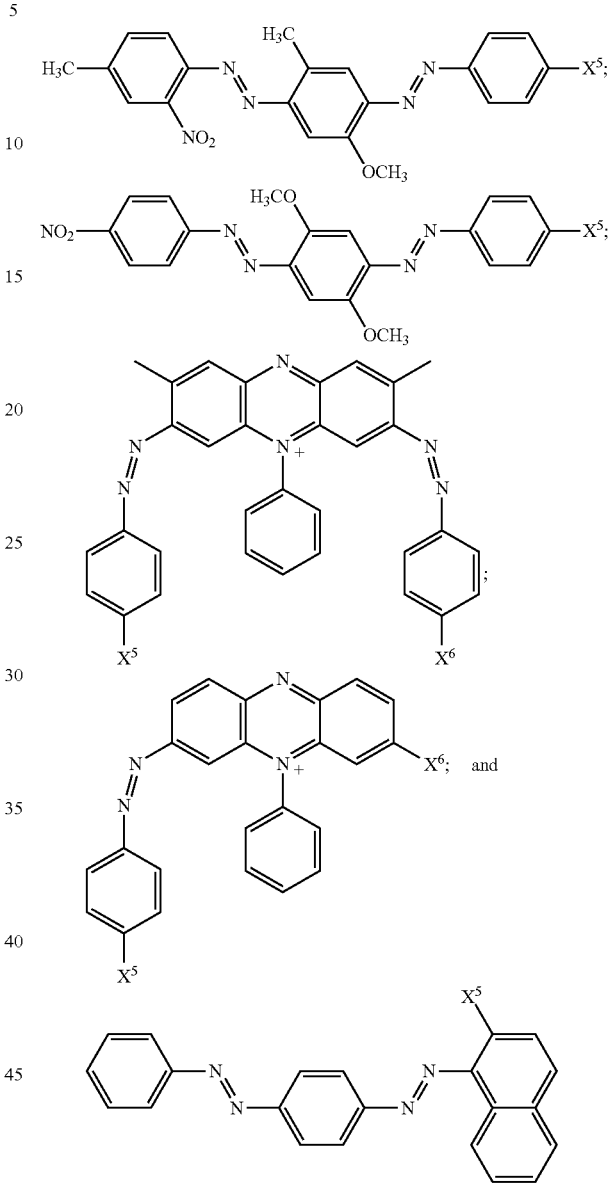

$X^5$ and $X^6$ are members independently selected from H, substituted or unsubstituted $C_1$-$C_6$ alkyl, —OR', —COOR', —NR'R", —SH, —OP($OX^3$)N($X^4$)$_2$, in which R' and R" are members independently selected from the group consisting of H, and alkyl or substituted alkyl. At least one of $X^5$ and $X^6$ is a reactive functional group. $X^3$ and $X^4$ are members independently selected from CN, and substituted or unsubstituted $C_1$-$C_6$ alkyl.

The following discussion is generally relevant to the identity of the reactive groups of the compounds of the invention and is particularly relevant to the groups X, $X^1$ and $X^2$ in each of the above-described aspects of the invention.

In a preferred embodiment, X is a member selected from amine, alkyl amine, substituted alkyl amine, and aryl amine groups, more preferably X has a structure according to Formula VII:

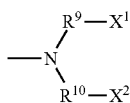

(VII)

wherein, $R^9$ and $R^{16}$ are members independently selected from alkyl and substituted alkyl; and $X^1$ and $X^2$ are members independently selected from —$CH_3$, —OH, —COOH, —$NH_2$, —SH, —OP($OX^3$)N($X^4$)$_2$, wherein, $X^3$ and $X^4$ are members independently selected from alkyl and substituted alkyl, and preferably $X^3$ is cyanoethyl; and $X^4$ is isopropyl.

In another preferred embodiment, a member selected from $R^9$, $R^{10}$ and combinations thereof comprises a polyether. Preferred polyethers include, for example, poly(ethylene glycol), poly(propyleneglycol) and copolymers thereof.

In a further preferred embodiment, X has a structure according to Formula VIII:

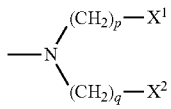

(VIII)

wherein, $X^1$, $X^2$, $X^3$ and $X^4$ are substantially as described above and p and q are numbers independently selected from 1 to 20, inclusive, preferably from 2 to 16, inclusive.

The compounds of the invention can be prepared as a single isomer or a mixture of isomers, including, for example cis-isomers, trans-isomers, diastereomers and stereoisomers. In a preferred embodiment, the compounds are prepared as substantially a single isomer. Isomerically pure compounds are prepared by using synthetic intermediates that are isomerically pure in combination with reactions that either leave the stereochemistry at a chiral center unchanged or result in its complete inversion. Alternatively, the final product or intermediates along the synthetic route can be resolved into a single isomer. Techniques for inverting or leaving unchanged a particular stereocenter, and those for resolving mixtures of stereoisomers are well known in the art and it is well within the ability of one of skill in the art to choose an appropriate resolution or synthetic method for a particular situation. See, generally, Furniss et al. (eds.) VOGEL'S ENCYCLOPEDIA OF PRACTICAL ORGANIC CHEMISTRY $5^{TH}$ ED., Longman Scientific and Technical Ltd., Essex, 1991, pp. 809-816; and Heller, *Acc. Chem. Res.* 23: 128 (1990).

Reactive Functional Groups

The compounds of the invention bear a reactive functional group, which can be located at any position on an aryl nucleus or on a chain, such as an alkyl chain, attached to an aryl nucleus. When the reactive group is attached to an alkyl, or substituted alkyl chain tethered to an aryl nucleus, the reactive group is preferably located at a terminal position of an alkyl chain. Reactive groups and classes of reactions useful in practicing the present invention are generally those that are well known in the art of bioconjugate chemistry. Currently favored classes of reactions available with reactive BHQs are those which proceed under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition).

These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

Useful reactive functional groups include, for example:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups, which can be converted to esters, ethers, aldehydes, etc.

(c) haloalkyl groups, wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups, which are capable of participating in Diels-Alder reactions such as, for example, maleimido groups;

(e) aldehyde or ketone groups, such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be, for example, converted to disulfides or reacted with acyl halides;

(h) amine or sulfhydryl groups, which can be, for example, acylated, alkylated or oxidized;

(i) alkenes, which can undergo, for example, cycloadditions, acylation, Michael addition, etc;

(j) epoxides, which can react with, for example, amines and hydroxyl compounds; and (k) phosphoramidites and other standard functional groups useful in nucleic acid synthesis.

The reactive functional groups can be chosen such that they do not participate in, or interfere with, the reactions necessary to assemble the reactive BHQ analogue. Alternatively, a reactive functional group can be protected from participating in the reaction by the presence of a protecting group. Those of skill in the art understand how to protect a particular functional group such that it does not interfere with a chosen set of reaction conditions. For examples of useful protecting groups, see, for example, Greene et al., PROTECTIVE GROUPS IN ORGANIC SYNTHESIS, John Wiley & Sons, New York, 1991.

Donor and Acceptor Moieties

One of the advantages of the compounds of the invention is that a wide range of energy donor molecules can be used in conjunction with the BHQs. A vast array of fluorophores are known to those of skill in the art. See, for example, Cardullo et al., *Proc. Natl. Acad. Sci. USA* 85: 8790-8794 (1988); Dexter, D. L., *J. of Chemical Physics* 21: 836-850 (1953); Hochstrasser et al., *Biophysical Chemistry* 45: 133-141 (1992); Selvin, P., *Methods in Enzymology* 246: 300-334 (1995); Steinberg, I. *Ann. Rev. Biochem.*, 40: 83-114 (1971); Stryer, L. *Ann. Rev. Biochem.*, 47: 819-846 (1978); Wang et al., *Tetrahedron Letters* 31: 6493-6496 (1990); Wang et al., *Anal. Chem.* 67: 1197-1203 (1995).

A non-limiting list of exemplary donors that can be used in conjunction with the quenchers of the invention is provided in Table 1.

TABLE 1

Suitable moieties that can be selected as donors or acceptors in donor-acceptor energy transfer pairs 4-acetamido-4'-isothiocyanatostilbene-2,2'disulfonic acid
acridine and derivatives:

acridine
acridine isothiocyanate
5-(2'-aminoethyl)aminonaphthalene-1-sulfonic acid (EDANS)
4-amino-N-[3-vinylsulfonyl)phenyl]naphthalimide-3,5 disulfonate
N-(4-anilino-1-naphthyl)maleimide
anthranilamide
BODIPY
Brilliant Yellow
coumarin and derivatives:

coumarin
7-amino-4-methylcoumarin (AMC, Coumarin 120)
7-amino-4-trifluoromethylcouluarin (Coumaran 151)
cyanine dyes
cyanosine
4',6-diaminidino-2-phenylindole (DAPI)
5',5''-dibromopyrogallol-sulfonaphthalein (Bromopyrogallol Red)
7-diethylamino-3-(4'-isothiocyanatophenyl)-4-methylcoumarin
diethylenetriamine pentaacetate
4,4'-diisothiocyanatodihydro-stilbene-2,2'-disulfonic acid
4,4'-diisothiocyanatostilbene-2,2'-disulfonic acid
5-[dimethylamino]naphthalene-1-sulfonyl chloride (DNS, dansylchloride)
4-(4'-dimethylaminophenylazo)benzoic acid (DABCYL)
4-dimethylaminophenylazophenyl-4'-isothiocyanate (DABITC)
eosin and derivatives:

eosin
eosin isothiocyanate
erythrosin and derivatives:

erythrosin B
erythrosin isothiocyanate
ethidium
fluorescein and derivatives:

5-carboxyfluorescein (FAM)
5-(4,6-dichlorotriazin-2-yl)aminofluorescein (DTAF)
2',7'-dimethoxy-4'5'-dichloro-6-carboxyfluorescein (JOE)
fluorescein
fluorescein isothiocyanate
QFITC (XRITC)
fluorescamine
IR144
IR1446
Malachite Green isothiocyanate
4-methylumbelliferone
ortho cresolphthalein
nitrotyrosine
pararosaniline
Phenol Red
B-phycoerythrin
o-phthaldialdehyde
pyrene and derivatives:

pyrene
pyrene butyrate
succinimidyl 1-pyrene butyrate
quantum dots
Reactive Red 4 (Cibacron™ Brilliant Red 3B-A)
rhodamine and derivatives:

6-carboxy-X-rhodamine (ROX)
6-carboxyrhodamine (R6G)
lissamine rhodamine B sulfonyl chloride rhodamine (Rhod)
rhodamine B
rhodamine 123
rhodamine X isothiocyanate
sulforhodamine B
sulforhodamine 101
sulfonyl chloride derivative of sulforhodamine 101 (Texas Red)
N,N,N',N'-tetramethyl-6-carboxyrhodamine (TAMRA)
tetramethyl rhodamine

TABLE 1-continued

Suitable moieties that can be selected as donors or acceptors in donor-acceptor energy transfer pairs tetramethyl rhodamine isothiocyanate (TRITC)
riboflavin
rosolic acid
terbium chelate derivatives There is a great deal of practical guidance available in the literature for selecting appropriate donor-acceptor pairs for particular probes, as exemplified by the following references: Pesce et al., Eds., FLUORESCENCE SPECTROSCOPY (Marcel Dekker, New York, 1971); White et al., FLUORESCENCE ANALYSIS: A PRACTICAL APPROACH (Marcel Dekker, New York, 1970); and the like. The literature also includes references providing exhaustive lists of fluorescent and chromogenic molecules and their relevant optical properties for choosing reporter-quencher pairs (see, for example, Berlman, HANDBOOK OF FLUORESCENCE SPECTRA OF AROMATIC MOLECULES, 2nd Edition (Academic Press, New York, 1971); Griffiths, COLOUR AND CONSTITUTION OF ORGANIC MOLECULES (Academic Press, New York, 1976); Bishop, Ed., INDICATORS (Pergamon Press, Oxford, 1972); Haugland, HANDBOOK OF FLUORESCENT PROBES AND RESEARCH CHEMICALS (Molecular Probes, Eugene, 1992) Pringsheim, FLUORESCENCE AND PHOSPHORESCENCE (Interscience Publishers, New York, 1949); and the like. Further, there is extensive guidance in the literature for derivatizing reporter and quencher molecules for covalent attachment via common reactive groups that can be added to a nucleic acid, as exemplified by the following references: Haugland (supra); Ullman et al., U.S. Pat. No. 3,996,345; Khanna et al., U.S. Pat. No. 4,351,760. Thus, it is well within the abilities of those of skill in the art to choose an energy exchange pair for a particular application and to conjugate the members of this pair to a probe molecule, such as, for example, a nucleic acid, peptide or other polymer.

Generally, it is preferred that an absorbance band of the BHQ substantially overlap the fluorescence emission band of the donor. When the donor (fluorophore) is a component of a probe that utilizes donor-acceptor energy transfer, the donor fluorescent moiety and the quencher (acceptor) of the invention are preferably selected so that the donor and acceptor moieties exhibit donor-acceptor energy transfer when the donor moiety is excited. One factor to be considered in choosing the fluorophore-quencher pair is the efficiency of donor-acceptor energy transfer between them. Preferably, the efficiency of FRET between the donor and acceptor moieties is at least 10%, more preferably at least 50% and even more preferably at least 80%. The efficiency of FRET can easily be empirically tested using the methods both described herein and known in the art.

The efficiency of energy transfer between the donor-acceptor pair can also be adjusted by changing the ability of the donor and acceptor groups to dimerize or closely associate. If the donor and acceptor moieties are known or determined to closely associate, an increase or decrease in association can be promoted by adjusting the length of a linker moiety, or of the probe itself, between the donor and acceptor. The ability of donor-acceptor pair to associate can be increased or decreased by tuning the hydrophobic or ionic interactions, or the steric repulsions in the probe construct. Thus, intramolecular interactions responsible for the association of the donor-acceptor pair can be enhanced or attenuated. Thus, for example, the association between the donor-acceptor pair can be increased by, for example, utilizing a donor bearing an overall negative charge and an acceptor with an overall positive charge.

In addition to fluorophores that are attached directly to a probe, the fluorophores can also be attached by indirect means. In this embodiment, a ligand molecule (e.g., biotin) is generally covalently bound to the probe species. The ligand then binds to another molecules (e.g., streptavidin) molecule, which is either inherently detectable or covalently bound to a signal system, such as a fluorescent compound, or an enzyme that produces a fluorescent compound by conversion of a non-fluorescent compound. Useful enzymes of interest as labels include, for example, hydrolases, particularly phosphatases, esterases and glycosidases, hydrolases, peptidases or oxidases, particularly peroxidases, and. Fluorescent compounds include fluorescein and its derivatives, rhodamine and its derivatives, dansyl, umbelliferone, etc., as discussed above. For a review of various labeling or signal producing systems that can be used, see, U.S. Pat. No. 4,391,904.

Presently preferred donors of use in conjunction with BHQ, include, for example, xanthene dyes, including fluoresceins, cyanine dyes and rhodamine dyes. Many suitable forms of these compounds are widely available commercially with substituents on their phenyl moieties, which can be used as the site for bonding or as the bonding functionality for attachment to an nucleic acid. Another group of preferred fluorescent compounds are the naphthylamines, having an amino group in the alpha or beta position. Included among such naphthylamino compounds are 1-dimethylaminonaphthyl-5-sulfonate, 1-anilino-8-naphthalene sulfonate and 2-p-touidinyl-6-naphthalene sulfonate. Other donors include 3-phenyl-7-isocyanatocoumarin, acridines, such as 9-isothiocyanatoacridine and acridine orange; N-(p-(2-benzoxazolyl)phenyl)maleimide; benzoxadiazoles, stilbenes, pyrenes, and the like.

For clarity of illustration, the discussion below focuses on attaching BHQs and fluorophores to nucleic acids. The focus on nucleic acid probes is not intended to limit the scope of probe molecules to which BHQs can be attached. Those of skill in the art will appreciate that BHQs can also be attached to small molecules, proteins, peptides, synthetic polymers, solid supports and the like using standard synthetic chemistry.

In a presently preferred embodiment, in which the probe is a nucleic acid probe, the reporter molecule is a fluorescein dye (FAM). The fluorescein moiety is preferably attached to either the 3'- or the 5'-terminus of the nucleic acid, although internal sites are also accessible and have utility for selected purposes. Whichever terminus the FAM derivative is attached to, the BHQ will generally be attached to its antipode, or at a position internal to the nucleic acid chain. The FAM donor is preferably introduced using a 6-FAM amidite. Different donor groups are also preferably introduced using an amidite derivative of the donor. Alternatively, donor groups comprising reactive groups (e.g., isothiocyanates, active esters, etc.) can be introduced via reaction with a reactive moiety on a tether or linker arm attached to the nucleic acid (e.g., hexyl amine).

In yet another preferred embodiment, the donor moiety can be attached at the 3'-terminus of a nucleic acid by the use of a derivatized synthesis support. For example, TAMRA (tetramethylrhodamine carboxylic acid) is attached to a nucleic acid 3'-terminus using a solid support that is derivatized with an analogue of this fluorophore (Biosearch Technologies, Inc.)

In view of the well-developed body of literature concerning the conjugation of small molecules to nucleic acids, many other methods of attaching donor/acceptor pairs to nucleic acids will be apparent to those of skill in the art. For example, rhodamine and fluorescein dyes are conveniently attached to the 5'-hydroxyl of an nucleic acid at the conclusion of solid phase synthesis by way of dyes derivatized with a phosphoramidite moiety (see, for example, Woo et al., U.S. Pat. No. 5,231,191; and Hobbs, Jr., U.S. Pat. No. 4,997,928).

More specifically, there are many linking moieties and methodologies for attaching groups to the 5'- or 3'-termini of nucleic acids, as exemplified by the following references: Eckstein, editor, Nucleic acids and Analogues: A Practical Approach (IRL Press, Oxford, 1991); Zuckerman et al., *Nucleic Acids Research*, 15: 5305-5321 (1987) (3'-thiol group on nucleic acid); Sharma et al., *Nucleic Acids Research*, 19: 3019 (1991) (3'-sulfhydryl); Giusti et al., *PCR Methods and Applications*, 2: 223-227 (1993) and Fung et al., U.S. Pat. No. 4,757,141 (5'-phosphoamino group via Aminolink TM II available from P.E. Biosystems, CA.) Stabinsky, U.S. Pat. No. 4,739,044 (3-aminoalkylphosphoryl group); Agrawal et al., *Tetrahedron Letters*, 31: 1543-1546 (1990) (attachment via phosphoramidate linkages); Sproat et al., *Nucleic Acids Research*, 15: 4837 (1987) (5-mercapto group); Nelson et al., *Nucleic Acids Research*, 17: 7187-7194 (1989) (3'-amino group), and the like.

Means of detecting fluorescent labels are well known to those of skill in the art. Thus, for example, fluorescent labels can be detected by exciting the fluorophore with the appropriate wavelength of light and detecting the resulting fluorescence. The fluorescence can be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product.

Synthesis

The compounds of the invention are synthesized by an appropriate combination of generally well-known synthetic methods. Techniques useful in synthesizing the compounds of the invention are both readily apparent and accessible to those of skill in the relevant art. The discussion below is offered to illustrate certain of the diverse methods available for use in assembling the compounds of the invention, it is not intended to define the scope of reactions or reaction sequences that are useful in preparing the compounds of the present invention.

One method of synthesizing compounds of the invention is set forth in Scheme 1 (FIG. 1). Scheme 1 is a generalized schematic of one synthetic scheme useful with the BHQs of the invention. An azido derivative of a dye is coupled to an aryl derivative 1, at pH 9, forming the corresponding diazo adduct 2. The diol 2 is monoprotected with a group, such as the dimethoxytrityl group to form compound 3, having one free hydroxyl moiety. Compound 3 is converted to phosphoramidite 4 by contacting it with an agent, such as 2-cyanoethyl diisopropylchlorophosphoramidite in the presence of a mildly acidic activator, such as tetrazole. The phosphoramidite is coupled to a hydroxyl-bearing controlled pore glass support and subsequently oxidized to the corresponding phosphotriester derivative, thereby forming an appropriate starting material, 5, for the synthesis of an array of nucleic acids derivatized at the 3'-position with a BHQ.

The above-recited synthetic scheme is intended to be exemplary of one embodiment of the invention, those of skill in the art will recognize that many other synthetic strategies employing reactive BHQ analogues are available. For example, by a slight modification of the method above, a derivative appropriate for modification of a nucleic acid at the 5'-position is easily accessible. In an alternative scheme, compound 4, is not tethered to a solid support, but is added as the final subunit during nucleic acid synthesis, to prepare a nucleic acid with a 5'-BHQ group.

Figure 2:
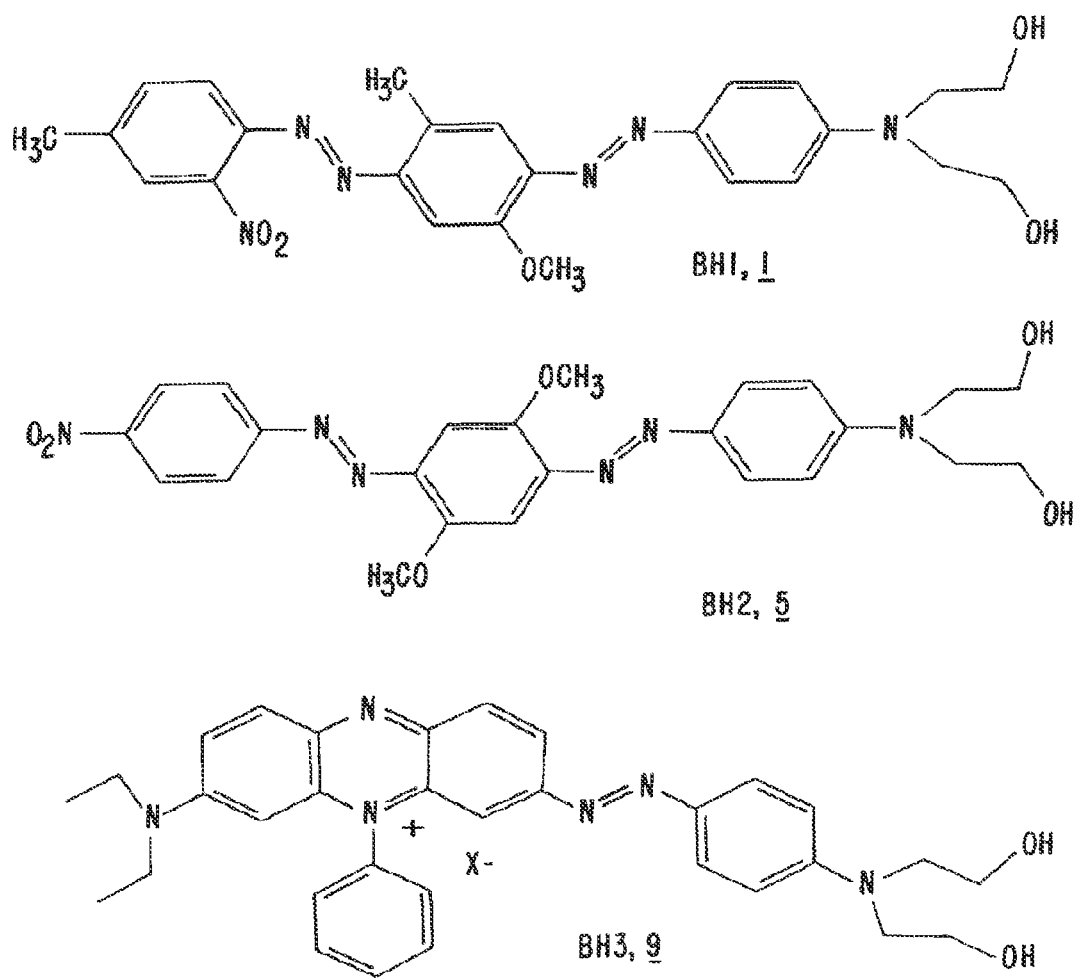
FIG. 2 is a collection of structures of exemplary BHQs (BH1, BH2 and BH3) of the invention.

The above-described synthetic scheme can be practiced using a variety of BHQ compounds of the invention, such as those set forth in FIG. 2. FIG. 2 provides the structures of three exemplary BHQs, BH1 (6), BH2 (10) and BH3 (14).

Figure 3:
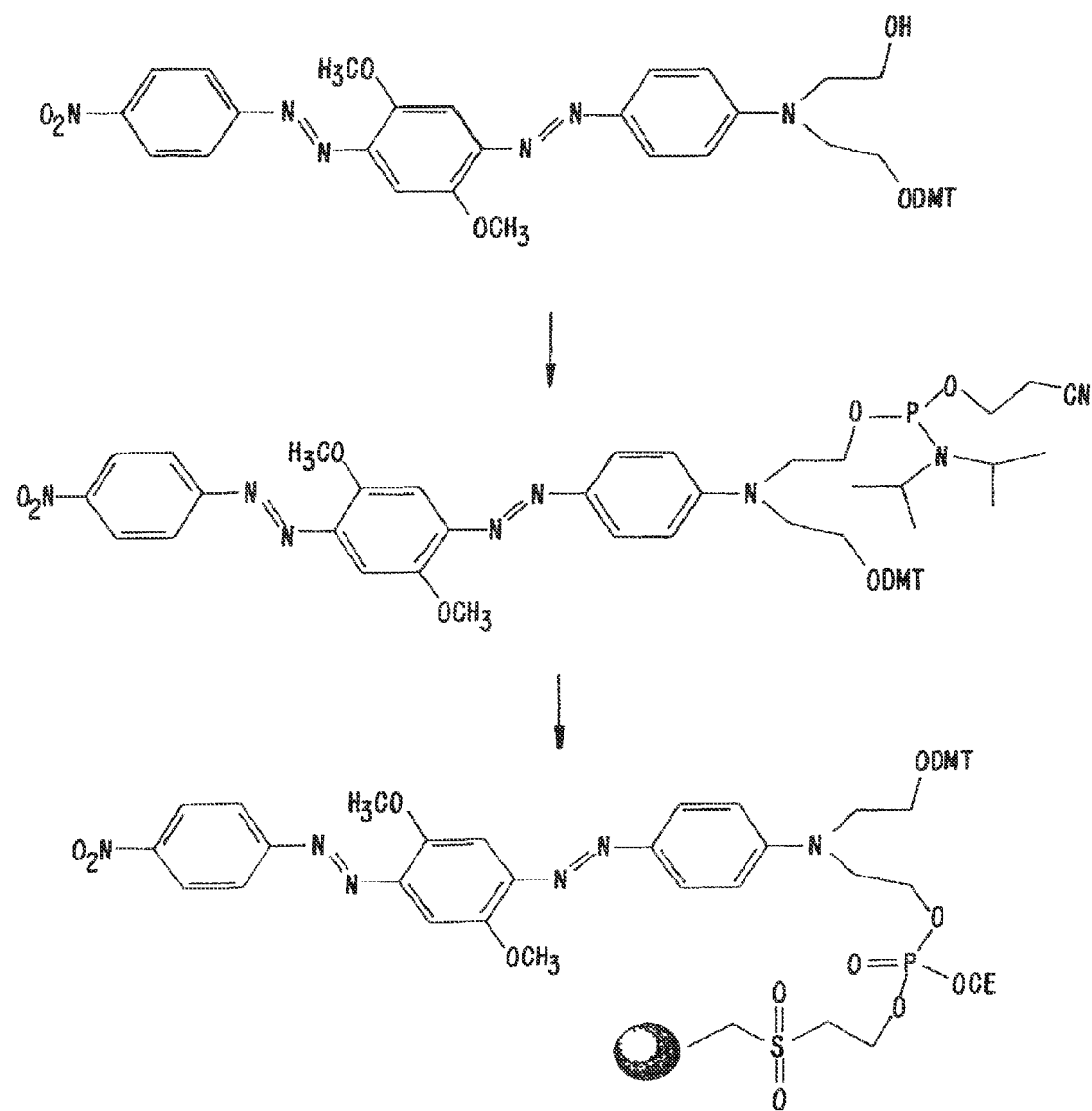
FIG. 3 is a collection of structures of an exemplary BHQ attached to a controlled pore glass support (BH1-CPG) and intermediates along the synthesis of BH1-CPG.
Figure 4:
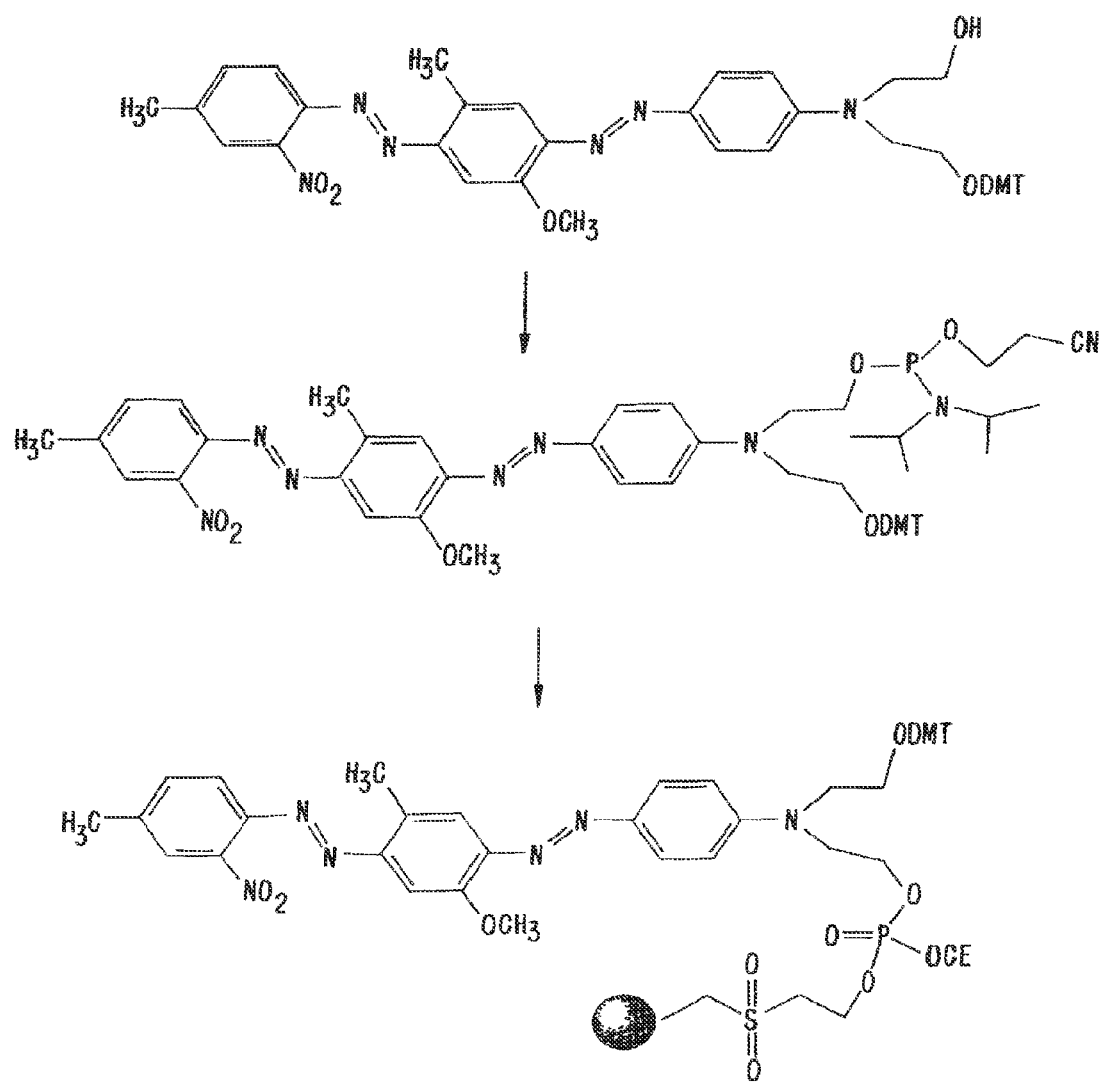
FIG. 4 is a collection of structures of an exemplary BHQ attached to a controlled pore glass support (BH2-CPG) and intermediates along the synthesis of BH2-CPG.
Figure 5:
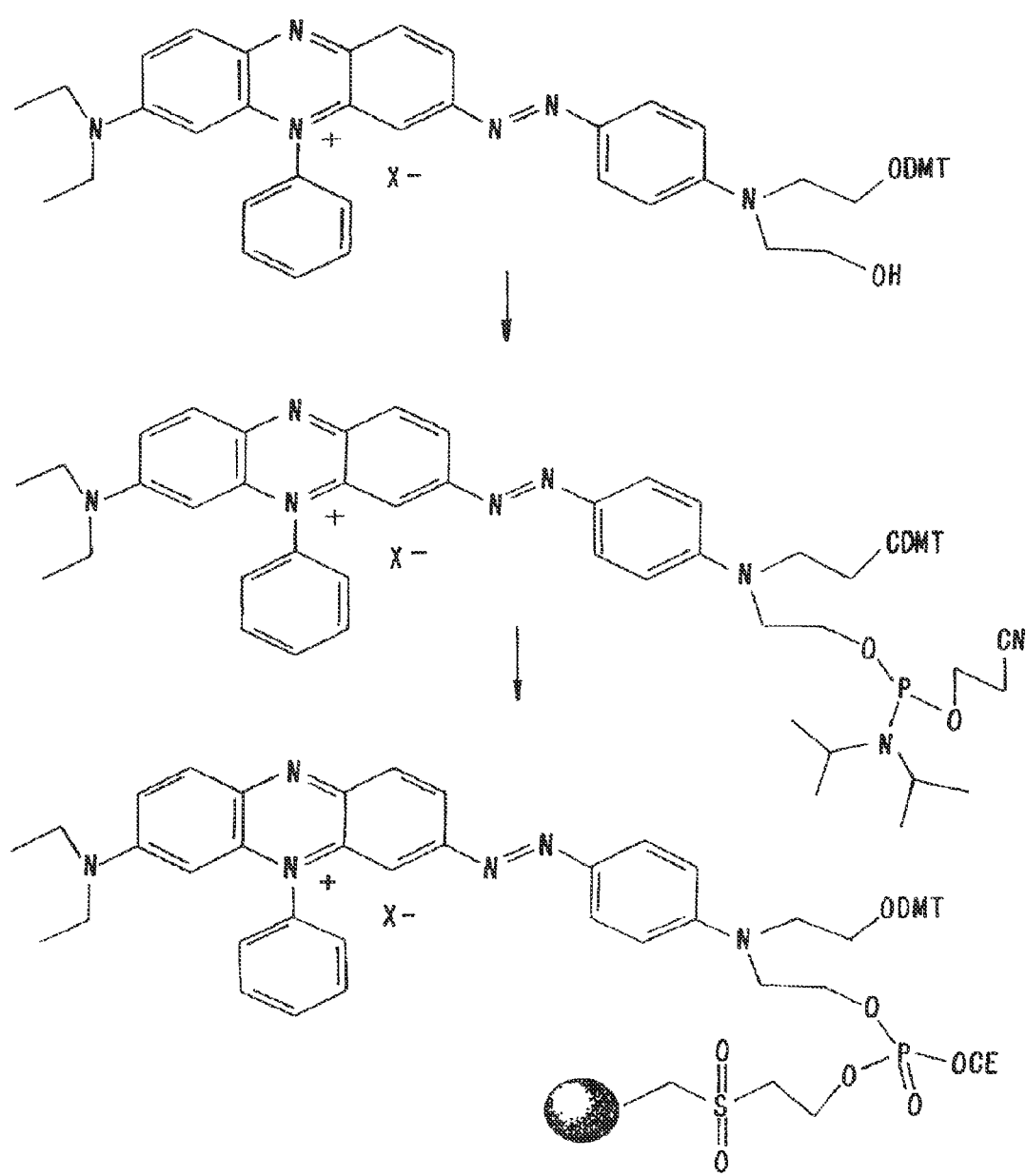
FIG. 5 is a collection of structures of an exemplary BHQ attached to a controlled pore glass support (BH3-CPG) and intermediates along the synthesis of BH3-CPG.
Figure 6:
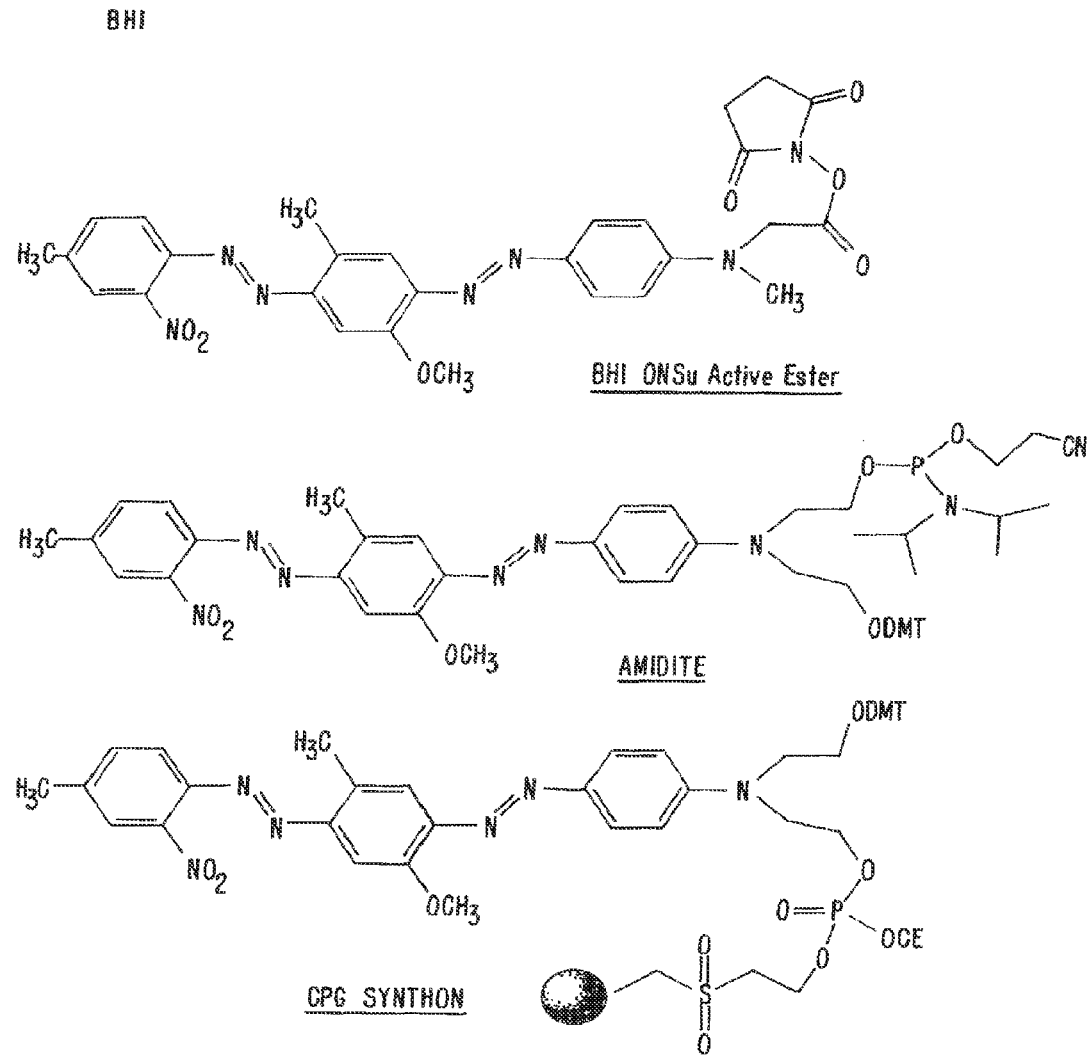
FIG. 6 is a collection of structures of activated derivatives of BH1.

FIG. 3 sets forth the structures of a phosphoramidite (8) of BH1 (7), and a derivative of BH1, which is tethered to a controlled pore glass support (9). Both the phosphoramidite and the CPG conjugate can be prepared by art-recognized methods, including those set forth herein. Similarly, FIG. 4 sets forth the structures of a phosphoramidite (12) of BH2 (11), and a derivative of BH2, which is tethered to a controlled pore glass support (13) and FIG. 5 sets forth the structures of a phosphoramidite (16) of BH1 (15), and a derivative of BH3, which is tethered to a controlled pore glass support (17).

In a still further modification of the scheme of FIG. 1, compound 4 is coupled to a nucleic acid intermediate between the 3'- and 5'-positions, the DMT group is removed using standard nucleic acid chemistry, or a modification thereof, and a nucleic acid subunit is tethered to the deprotected primary hydroxyl group as though the hydroxyl group were the 5'-hydroxyl of a preceding nucleic acid subunit, thereby providing a nucleic acid having a BHQ moiety at an internal position.

Assays and BHQ-Bearing Probes

In another preferred embodiment, the present invention provides a BHQ that is tethered to another molecule, such as a probe molecule and assays using these probes.

Assays

The following discussion is generally relevant to the assays described herein. This discussion is intended to illustrate the invention by reference to certain preferred embodiments and should not be interpreted as limiting the scope of probes and assay types in which the compounds of the invention find use. Other assay formats utilizing the compounds of the invention will be apparent to those of skill in the art.

In general, to determine the concentration of a target molecule, such as, for example, a nucleic acid, it is preferable to first obtain reference data in which constant amounts of probe and nucleic acid ligand are contacted with varying amounts of target. The fluorescence emission of each of the reference mixtures is used to derive a graph or table in which target concentration is compared to fluorescence emission. For example, a probe that: a) hybridizes to a target-free nucleic acid ligand; and b) has a stem-loop architecture with the 5' and 3' termini being the sites of fluorescent group and BHQ labeling, can be used to obtain such reference data. Such a probe gives a characteristic emission profile in which the fluorescence emission decreases as the target concentration increases in the presence of a constant amount of probe and nucleic acid ligand. Then, a test mixture with an unknown amount of target is contacted with the same amount of first nucleic acid ligand and second probe, and the fluorescence emission is determined. The value of the fluorescence emission is then compared with the reference data to obtain the concentration of the target in the test mixture.

Multiplex Analyses

In another preferred embodiment, the quenchers of the invention are utilized as a component of one or more probes used in a multiplex assay for detecting one or more species in a mixture.

Probes that include the BHQs of the invention are particularly useful in performing multiplex-type analyses and assays. In a typical multiplex analysis, two or more distinct species (or regions of one or more species) are detected using two or more probes, wherein each of the probes is labeled with a different fluorophore. Preferred species used in multiplex analyses relying on donor-acceptor energy transfer meet at least two criteria: the fluorescent species is bright and spectrally well-resolved; and the energy transfer between the fluorescent species and the quencher is efficient.

Thus, in a further embodiment, the invention provides a mixture comprising at least a first carrier molecule and a second carrier molecule. The first carrier molecule has covalently bound thereto a first quencher of excited state energy having a structure comprising at least three radicals selected from aryl, substituted aryl, heteroaryl, substituted heteroaryl and combinations thereof. At least two of the radicals are covalently linked via an exocyclic diazo bond. The mixture also includes a second carrier molecule. The second carrier molecule has covalently bound thereto a second quencher of excited state energy having a structure comprising at least three radicals selected from aryl, substituted aryl, heteroaryl, substituted heteroaryl and combinations thereof, wherein at least two of the radicals are covalently linked via an exocyclic diazo bond.

The BHQs of the invention allow for the design of multiplex assays in which more than one quencher structure is used in the assay. A number of different multiplex assays using the BHQs of the invention will be apparent to one of skill in the art. In one exemplary assay, each of the at least two distinct BHQ quenchers is used to quench energy derived from one or more identical fluorophore. Alternatively, an assay can be practiced in which each distinct BHQ quenches energy derived from a distinct fluorophore to which the BHQ is "matched." The fluorophores can be bound to the same molecule as the BHQ or to a different molecule. Moreover, similar to the BHQs and the fluorophores, the carrier molecules of use in a particular assay system can be the same or different.

In addition to the mixtures described above, the present invention also provides a method for detecting or quantifying a particular molecular species. The method includes: (a) contacting the species with a mixture such as that described above; and (b) detecting a change in a fluorescent property of one or more component of the mixture, the molecular species or a combination thereof, thereby detecting or quantifying the molecular species.

Figure 7A:
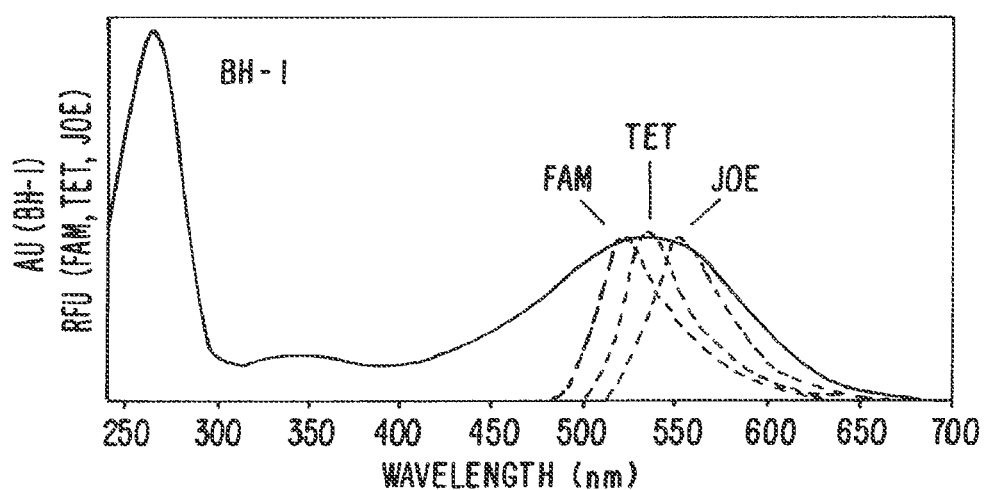
FIG. 7A-7B is a comparison of the absorbance spectra of Dabcyl and the BHQs of the invention.
Figure 7B:
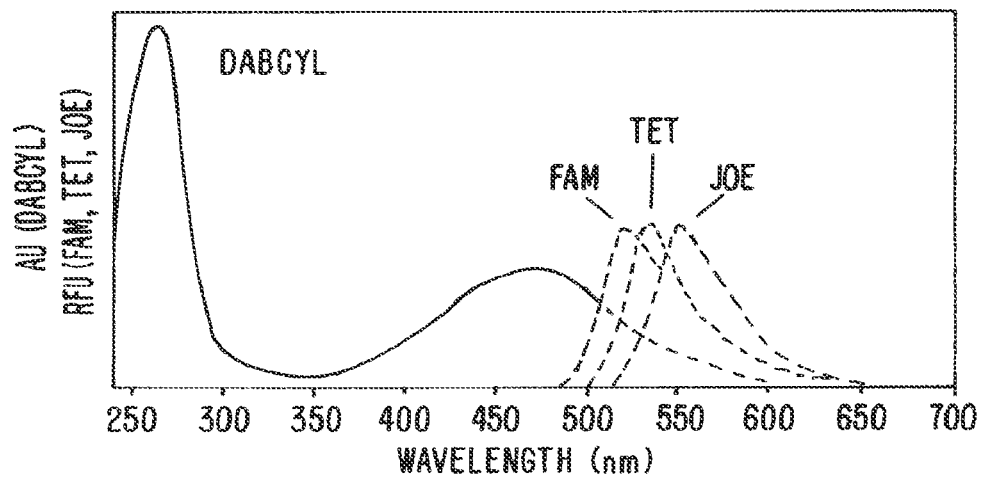
Figure 8A:
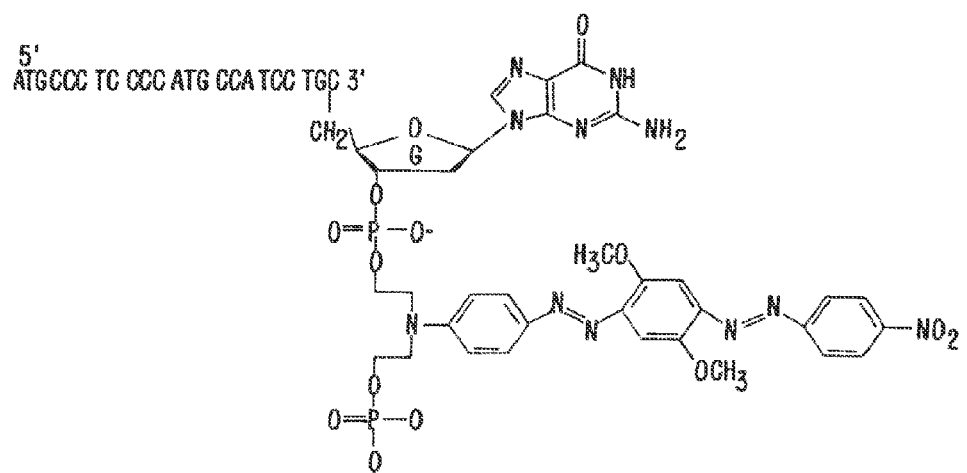
FIG. 8A-8B is a series of nucleic acid structures incorporating exemplary BHQs of the invention.
Figure 8A:
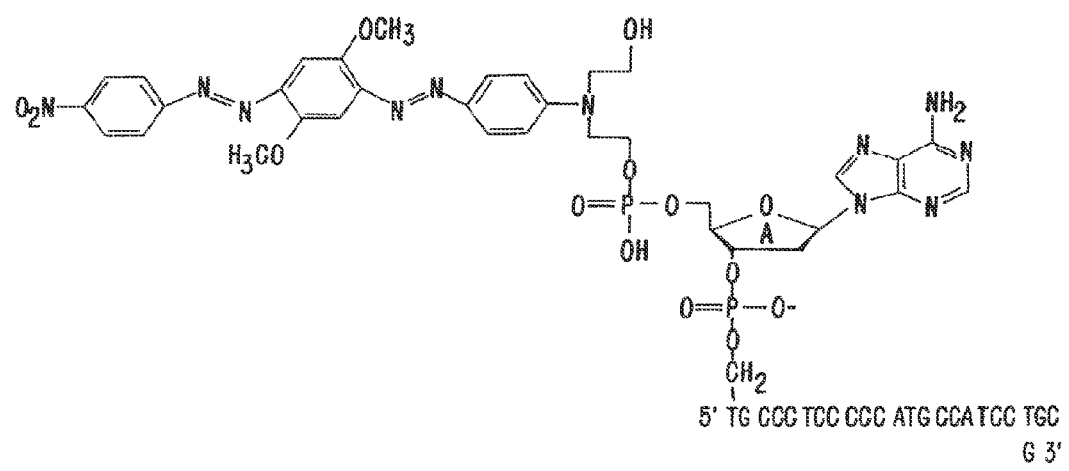
Figure 8B:
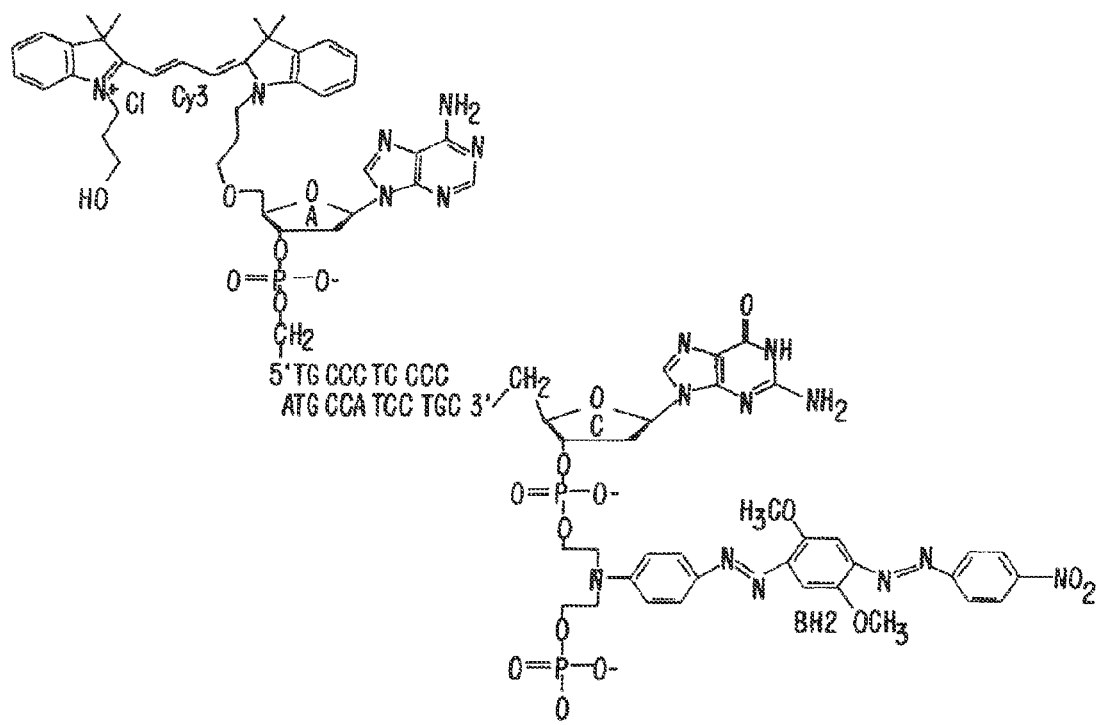

Because of the ready availability of BHQs of the invention having different absorbance characteristics, the compounds of the invention are particularly well suited for use in multiplex applications. Access to BHQs having a range of absorbance characteristics allows for the design of donor-acceptor energy transfer probes in which the acceptor emission properties and the BHQ absorbance properties are substantially matched, thereby providing a useful level of spectral overlap (see, for example, FIG. 7).

The simultaneous use of two or more probes using donor-acceptor energy transfer is known in the art. For example, multiplex assays using nucleic acid probes with different sequence specificities have been described. Fluorescent probes have been used to determine whether an individual is homozygous wild-type, homozygous mutant or heterozygous for a particular mutation. For example, using one quenched-fluorescein molecular beacon that recognizes the wild-type sequence and another rhodamine-quenched molecular beacon that recognizes a mutant allele, it is possible to genotype individuals for the β-chemokine receptor (Kostrikis et al. *Science* 279:1228-1229 (1998)). The presence of only a fluorescein signal indicates that the individual is wild-type, and the presence of rhodamine signal only indicates that the individual is a homozygous mutant. The presence of both rhodamine and fluorescein signal is diagnostic of a heterozygote. Tyagi et al. *Nature Biotechnology* 16: 49-53 (1998))

have described the simultaneous use of four differently labeled molecular beacons for allele discrimination, and Lee et al., *BioTechniques* 27: 342-349 (1999) have described seven color homogenous detection of six PCR products.

The quenchers of the present invention can be used in multiplex assays designed to detect and/or quantify substantially any species, including, for example, whole cells, viruses, proteins (e.g., enzymes, antibodies, receptors), glycoproteins, lipoproteins, subcellular particles, organisms (e.g., Salmonella), nucleic acids (e.g., DNA, RNA, and analogues thereof), polysaccharides, lipopolysaccharides, lipids, fatty acids, non-biological polymers and small molecules (e.g., toxins, drugs, pesticides, metabolites, hormones, alkaloids, steroids).

Probes

The invention provides probes including BHQ moieties conjugated to, for example, a target species (e.g., receptor, enzyme, etc.) a ligand for a target species (e.g., nucleic acid, peptide, etc.), a small molecule (e.g., drug, pesticide, etc.), and the like. The probes can be used for in vitro and in vivo applications.

A particularly unexpected and surprising advantage of the BHQs is their ability to quench excited state energy from fluorophores attached to carrier molecules (e.g., nucleic acids) without the need to design secondary structure forming components (e.g., hairpins, loops, etc.) into the carrier molecule to bring the fluorophore and the BHQ into proximity. The energy transfer pairs of probes presently used in the art typically require the introduction of some form of secondary structure in order to function properly, thereby seriously constraining the identity of species that can be used as carrier molecules. Thus, the probes of the present invention can be of simple design, can be produced more inexpensively and used to probe a much greater array of systems in much less time than current art-recognized probes.

Yet another unexpected property of the BHQs of the invention is their robustness under a variety of synthetic conditions used to attach the BHQs to a carrier molecule. For example, many of the BHQs of the invention survive the conditions necessary for automated synthesis of nucleic acids without undergoing any substantial degree of degradation or alteration. In contrast, many of the art-recognized quenchers presently in use require the use of special conditions to assemble the carrier molecule to which they are attached, or they have to be attached after the completion of the carrier molecule synthesis. The additional complexity of the synthesis of a probe increases both the duration of the synthesis and its cost.

Small Molecule Probes

The BHQs of the invention can be used as components of small molecule probes. In a preferred design, a small molecule probe includes a fluorophore or fluorophore precursor and a BHQ. In an exemplary embodiment, an agent, such as an enzyme cleaves the BHQ, the fluorophore or both from the small molecule generating fluorescence in the system under investigation (see, for example, Zlokarnik et al., *Science* 279: 84-88 (1998)).

Nucleic Acid Probes

The dark quenchers of the invention are useful in conjunction with nucleic-acid probes and they can be used as components of detection agents in a variety of DNA amplification/quantification strategies including, for example, 5'-nuclease assay, Strand Displacement Amplification (SDA), Nucleic Acid Sequence-Based Amplification (NASBA), Rolling Circle Amplification (RCA), as well as for direct detection of targets in solution phase or solid phase (e.g., array) assays. Furthermore, the BHQ-derivatized nucleic acids can be used in probes of substantially any format, including, for example, format selected from molecular beacons, Scorpion Probes™, Sunrise Probes™, conformationally assisted probes, light up probes, Invader Detection probes, and TaqMan™ probes. See, for example, Cardullo, R., et al., *Proc. Natl. Acad. Sci. USA*, 85:8790-8794 (1988); Dexter, D. L., J. Chem. Physics, 21:836-850 (1953); Hochstrasser, R. A., et al., *Biophysical Chemistry*, 45:133-141 (1992); Selvin, P., *Methods in Enzymology*, 246:300-334 (1995); Steinberg, I., *Ann. Rev. Biochem.*, 40:83-114 (1971); Stryer, L., *Ann. Rev. Biochem.*, 47:819-846 (1978); Wang, G., et al., *Tetrahedron Letters*, 31:6493-6496 (1990); Wang, Y., et al., *Anal. Chem.*, 67:1197-1203 (1995); Debouck, C., et al., in supplement to *nature genetics*, 21:48-50 (1999); Rehman, F. N., et al., *Nucleic Acids Research*, 27:649-655 (1999); Cooper, J. P., et al., *Biochemistry*, 29:9261-9268 (1990); Gibson, E. M., et al., *Genome Methods*, 6:995-1001 (1996); Hochstrasser, R. A., et al., *Biophysical Chemistry*, 45:133-141 (1992); Holland, P. M., et al., *Proc Natl. Acad. Sci. USA*, 88:7276-7289 (1991); Lee, L. G., et al., *Nucleic Acids Rsch.*, 21:3761-3766 (1993); Livak, K. J., et al., *PCR Methods and Applications*, Cold Spring Harbor Press (1995); Vamosi, G., et al., *Biophysical Journal*, 71:972-994 (1996); Wittwer, C. T., et al., *Biotechniques*, 22:176-181 (1997); Wittwer, C. T., et al., *Biotechniques*, 22:130-38 (1997); Giesendorf, B. A. J., et al., *Clinical Chemistry*, 44:482-486 (1998); Kostrikis, L. G., et al., *Science*, 279:1228-1229 (1998); Matsuo, T., *Biochemica et Biophysica Acta*, 1379:178-184 (1998); Piatek, A. S., et al., *Nature Biotechnology*, 16:359-363 (1998); Schofield, P., et al., *Appl. Environ. Microbiology*, 63:1143-1147 (1997); Tyagi S., et al., *Nature Biotechnology*, 16:49-53 (1998); Tyagi, S., et al., *Nature Biotechnology*, 14:303-308 (1996); Nazarenko, I. A., et al., *Nucleic Acids Research*, 25:2516-2521 (1997); Uehara, H., et al., *Biotechniques*, 26:552-558 (1999); D. Whitcombe, et al., *Nature Biotechnology*, 17:804-807 (1999); Lyamichev, V., et al., *Nature Biotechnology*, 17:292 (1999); Daubendiek, et al., *Nature Biotechnology*, 15:273-277 (1997); Lizardi, P. M., et al., *Nature Genetics*, 19:225-232 (1998); Walker, G., et al., *Nucleic Acids Res.*, 20:1691-1696 (1992); Walker, G. T., et al., *Clinical Chemistry*, 42:9-13 (1996); and Compton, J., *Nature*, 350:91-92 (1991).

Thus, in a further aspect, the present invention provides a method for detecting a nucleic acid target sequence. The method includes: (a) contacting the target sequence with a detector nucleic acid; (b) hybridizing the target binding sequence to the target sequence, thereby altering the conformation of the detector nucleic acid, causing a change in a fluorescence parameter; and (c) detecting the change in the fluorescence parameter, thereby detecting the nucleic acid target sequence.

In the methods described herein, unless otherwise noted, a preferred detector nucleic acid includes a single-stranded target binding sequence. The binding sequence has linked thereto: i) a fluorophore; and ii) a BHQ of the invention. Moreover, prior to its hybridization to a complementary sequence, the detector nucleic acid is preferably in a conformation that allows donor-acceptor energy transfer between the fluorophore and the BHQ when the fluorophore is excited. Furthermore, in each of the methods described in this section, a change in fluorescence is detected as an indication of the presence of the target sequence. The change in fluorescence is preferably detected in-real time.

Presently preferred nucleic acid probes do not require the carrier molecule to adopt a secondary structure for the probe to function.

In this method, and unless otherwise noted, the other methods described in this section, the detector nucleic acid can assume substantially any intramolecularly associated secondary structure, but this structure is preferably a member selected from hairpins, stem-loop structures, pseudoknots, triple helices and conformationally assisted structures. Moreover, the intramolecularly base-paired secondary structure preferably comprises a portion of the target binding sequence.

In another aspect, the invention provides a method for detecting amplification of a target sequence. The method includes the use of an amplification reaction including the following steps: (a) hybridizing the target sequence and a detector nucleic acid. The detector nucleic acid includes a single-stranded target binding sequence and an intramolecularly associated secondary structure 5' to the target binding sequence. At least a portion of the detector sequence forms a single stranded tail which is available for hybridization to the target sequence; (b) extending the hybridized detector nucleic acid on the target sequence with a polymerase to produce a detector nucleic acid extension product and separating the detector nucleic acid extension product from the target sequence; (c) hybridizing a primer to the detector nucleic acid extension product and extending the primer with the polymerase, thereby linearizing the intramolecularly associated secondary structure and producing a change in a fluorescence parameter; and (d) detecting the change in the fluorescence parameter, thereby detecting the target sequence.

In yet a further aspect, the invention provides a method of ascertaining whether a first nucleic acid and a second nucleic acid hybridize. In this method, the first nucleic acid includes a BHQ according to the invention. The method includes: (a) contacting the first nucleic acid with the second nucleic acid; (b) detecting an alteration in a fluorescent property of a member selected from the first nucleic acid, the second nucleic acid and a combination thereof, thereby ascertaining whether the hybridization occurs.

A probe bearing both a BHQ and a fluorophore can be used or, alternatively, one or more of the nucleic acids can be singly labeled with a BHQ or fluorophore. When a nucleic acid singly labeled with a BHQ is the probe, the interaction between the first and second nucleic acids can be detected by observing the interaction between the BHQ and the nucleic acid or, more preferably, the quenching by the BHQ of the fluorescence of a fluorophore attached to the second nucleic acid.

In addition to their general utility in probes designed to investigate nucleic acid amplification, detection and quantification, the present dark quenchers can be used in substantially any nucleic acid probe format now known or later discovered. For example, the dark quenchers of the invention can be incorporated into probe motifs, such as Taqman™ probes (Held et al., *Genome Res.* 6: 986-994 (1996), Holland et al., *Proc. Nat. Acad. Sci. USA* 88: 7276-7280 (1991), Lee et al., *Nucleic Acids Res.* 21: 3761-3766 (1993)), molecular beacons (Tyagi et al., *Nature Biotechnology* 14:303-308 (1996), Jayasena et al., U.S. Pat. No. 5,989,823, issued Nov. 23, 1999)) scorpion probes (Whitcomb et al., *Nature Biotechnology* 17: 804-807 (1999)), sunrise probes (Nazarenko et al., *Nucleic Acids Res.* 25: 2516-2521 (1997)), conformationally assisted probes (Cook, R., copending and commonly assigned U.S. Provisional Application 60/138,376, filed Jun. 9, 1999), peptide nucleic acid (PNA)-based light up probes (Kubista et al., WO 97/45539, December 1997), double-strand specific DNA dyes (Higuchi et al, *Bio/Technology* 10: 413-417 (1992), Wittwer et al, *BioTechniques* 22: 130-138 (1997)) and the like. These and other probe motifs with which the present quenchers can be used are reviewed in NONISOTOPIC DNA PROBE TECHNIQUES, Academic Press, Inc. 1992.

The nucleic acids for use in the probes of the invention can be any suitable size, and are preferably in the range of from about 10 to about 100 nucleotides, more preferably from about 10 to about 80 nucleotides and more preferably still, from about 20 to about 40 nucleotides. The precise sequence and length of a nucleic acid probe of the invention depends in part on the nature of the target polynucleotide to which it binds. The binding location and length may be varied to achieve appropriate annealing and melting properties for a particular embodiment. Guidance for making such design choices can be found in many art-recognized references.

Preferably, the 3'-terminal nucleotide of the nucleic acid probe is blocked or rendered incapable of extension by a nucleic acid polymerase. Such blocking is conveniently carried out by the attachment of a donor or acceptor moiety to the terminal 3'-position of the nucleic acid probe, either directly or by a linking moiety.

The nucleic acid can comprise DNA, RNA or chimeric mixtures or derivatives or modified versions thereof. Both the probe and target nucleic acid can be present as a single strand, duplex, triplex, etc. Moreover, the nucleic acid can be modified at the base moiety, sugar moiety, or phosphate backbone with other groups such as radioactive labels, minor groove binders, intercalating agents, donor and/or acceptor moieties and the like.

For example, the nucleic acid can comprise at least one modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methyl ester, uracil-5-oxyacetic acid (v), 5-methyl-2-thiouracil, 3-(3-amino-3-N-2-carboxypropyl)uracil, (acp3)w, nitroindole, and 2,6-diaminopurine.

In another embodiment, the nucleic acid comprises at least one modified sugar moiety selected from the group including, but not limited to, arabinose, 2-fluoroarabinose, xylulose, and hexose.

In yet another embodiment, the nucleic acid comprises at least one modified phosphate backbone selected from the group including, but not limited to, a peptide nucleic acid hybrid, a phosphorothioate, a phosphorodithioate, a phosphoramidothioate, a phosphoramidate, a phosphordiamidate, a methylphosphonate, an alkyl phosphotriester, and a formacetal or analog thereof.

Phosphodiester linked nucleic acids of the invention can be synthesized by standard methods known in the art, e.g. by use of an automated DNA synthesizer (such as are commercially available from P.E. Biosystems, etc.) using commercially available amidite chemistries. Nucleic acids bearing modified phosphodiester linking groups can be synthesized by methods known in the art. For example, phosphorothioate nucleic acids may be synthesized by the method of Stein et al. (*Nucl. Acids Res.* 16:3209 (1988)), methylphosphonate nucleic acids can be prepared by use of controlled pore glass polymer supports (Sarin et al., *Proc. Natl. Acad. Sci. U.S.A.* 85:7448-7451 (1988)). Other methods of synthesizing both phosphodiester- and modified phosphodiester-linked nucleic acids will be apparent to those of skill in the art.

Nucleic acid probes of the invention can be synthesized by a number of approaches, e.g., Ozaki et al., *Nucleic Acids Research*, 20: 5205-5214 (1992); Agrawal et al., *Nucleic Acids Research*, 18: 5419-5423 (1990); or the like. The nucleic acid probes of the invention are conveniently synthesized on an automated DNA synthesizer, e.g., a P.E. Biosystems, Inc. (Foster City, Calif.) model 392 or 394 DNA/RNA Synthesizer, using standard chemistries, such as phosphoramidite chemistry (see, for example, disclosed in the following references, Beaucage et al., *Tetrahedron*, 48: 2223-2311 (1992); Molko et al., U.S. Pat. No. 4,980,460; Koster et al., U.S. Pat. No. 4,725,677; Caruthers et al., U.S. Pat. Nos. 4,415,732; 4,458,066; and 4,973,679. Alternative chemistries resulting in non-natural backbone groups, such as phosphorothioate, phosphoramidate, and the like, can also be employed.

When the nucleic acids are synthesized utilizing an automated nucleic acid synthesizer, the donor and acceptor moieties are preferably introduced during automated synthesis. Alternatively, one or more of these moieties can be introduced either before or after the automated synthesis procedure has commenced. For example, donor and/or acceptor groups can be introduced at the 3'-terminus using a solid support modified with the desired group(s). Additionally, donor and/or acceptor groups can be introduced at the 5'-terminus by, for example a derivative of the group that includes a phosphoramidite. In another exemplary embodiment, one or more of the donor and/or acceptor groups is introduced after the automated synthesis is complete.

In the dual labeled probes, the donor moiety is preferably separated from the BHQ by at least about 10 nucleotides, and more preferably by at least about 15 nucleotides. The donor moiety is preferably attached to either the 3'- or 5'-terminal nucleotides of the probe. The BHQ moiety is also preferably attached to either the 3'- or 5'-terminal nucleotides of the probe. More preferably, the donor and acceptor moieties are attached to the 3'- and 5'- or 5'- and 3'-terminal nucleotides of the probe, respectively, although internal placement is also useful.

Once the desired nucleic acid is synthesized, it is preferably cleaved from the solid support on which it was synthesized and treated, by methods known in the art, to remove any protecting groups present (e.g., 60° C., 5 h, concentrated ammonia). In those embodiments in which a base-sensitive group is attached to the nucleic acids (e.g., TAMRA), the deprotection will preferably use milder conditions (e.g., butylamine: water 1:3, 8 hours, 70° C.). Deprotection under these conditions is facilitated by the use of quick deprotect amidites (e.g., dC-acetyl, dG-dmf).

Following cleavage from the support and deprotection, the nucleic acid is purified by any method known in the art, including chromatography, extraction and gel purification. In a preferred embodiment, the nucleic acid is purified using HPLC. The concentration and purity of the isolated nucleic acid is preferably determined by measuring the optical density at 260 nm in a spectrophotometer.

Peptide Probes

Peptides, proteins and peptide nucleic acids that are labeled with a fluorophore and a quencher of the invention can be used in both in vivo and in vitro enzymatic assays.

Thus, in another aspect, the present invention provides a method for determining whether a sample contains an enzyme. The method comprises: (a) contacting the sample with a peptide construct; (b) exciting the fluorophore; and (c) determining a fluorescence property of the sample, wherein the presence of the enzyme in the sample results in a change in the fluorescence property.

Peptide constructs useful in practicing the invention include those with the following features: i) a fluorophore; ii) a BHQ of the invention; and iii) a cleavage or assembly recognition site for the enzyme. Moreover, the peptide construct is preferably of a length and orientation and in a conformation allowing donor-acceptor energy transfer between the fluorophore and the BHQ when the fluorophore is excited.

When the probe is used to detect an enzyme, such as a degradative enzyme (e.g., protease), and a degree of donor-acceptor energy transfer that is lower than an expected amount is observed, this is generally indicative of the presence of an enzyme. The degree of donor-acceptor energy transfer in the sample can be determined, for example, as a function of the amount of fluorescence from the donor moiety, the amount of fluorescence from the acceptor moiety, the ratio of the amount of fluorescence from the donor moiety to the amount of fluorescence from the acceptor moiety or the excitation state lifetime of the donor moiety.

The assay also is useful for determining the amount of enzyme in a sample by determining the degree of donor-acceptor energy transfer at a first and second time after contact between the enzyme and the tandem construct, and determining the difference in the degree of donor-acceptor energy transfer. The difference in the degree of donor-acceptor energy transfer reflects the amount of enzyme in the sample.

The assay methods also can also be used to determine whether a compound alters the activity of an enzyme, i.e., screening assays. Thus, in a further aspect, the invention provides methods of determining the amount of activity of an enzyme in a sample from an organism. The method includes: (a) contacting a sample comprising the enzyme and the compound with a peptide construct comprising (b) exciting the fluorophore; and (c) determining a fluorescence property of the sample, wherein the activity of the enzyme in the sample results in a change in the fluorescence property. Peptide constructs useful in this aspect of the invention are substantially similar to those described immediately above.

In a preferred embodiment, the amount of enzyme activity in the sample is determined as a function of the degree of donor-acceptor energy transfer in the sample and the amount of activity in the sample is compared with a standard activity for the same amount of the enzyme. A difference between the amount of enzyme activity in the sample and the standard activity indicates that the compound alters the activity of the enzyme.

Representative enzymes with which the present invention can be practiced include, for example, trypsin, enterokinase, HIV-1 protease, prohormone convertase, interleukin-1b-converting enzyme, adenovirus endopeptidase, cytomegalovirus assemblin, leishmanolysin, β-secretase for amyloid precursor protein, thrombin, renin, angiotensin-converting enzyme, cathepsin-D and a kininogenase, and proteases in general.

Proteases play essential roles in many disease processes such as Alzheimer's, hypertension, inflammation, apoptosis, and AIDS. Compounds that block or enhance their activity have potential as therapeutic agents. Because the normal substrates of peptidases are linear peptides and because established procedures exist for making non-peptidic analogs, compounds that affect the activity of proteases are natural subjects of combinatorial chemistry. Screening compounds produced by combinatorial chemistry requires convenient enzymatic assays.

The most convenient assays for proteases are based on donor-acceptor energy transfer from a donor fluorophore to a quencher placed at opposite ends of a short peptide chain containing the potential cleavage site (see, Knight C. G., *Methods in Enzymol.* 248:18-34 (1995)). Proteolysis separates the fluorophore and quencher, resulting in increased intensity in the emission of the donor fluorophore. Existing protease assays use short peptide substrates incorporating unnatural chromophoric amino acids, assembled by solid phase peptide synthesis.

Assays of the invention are also useful for determining and characterizing substrate cleavage sequences of proteases or for identifying proteases, such as orphan proteases. In one embodiment the method involves the replacement of a defined linker moiety amino acid sequence with one that contains a randomized selection of amino acids. A library of fluorescent BHQ-bearing probes, wherein the fluorophore and the BHQ are linked by a randomized peptide linker moiety can be generated using recombinant engineering techniques or synthetic chemistry techniques. Screening the members of the library can be accomplished by measuring a signal related to cleavage, such as donor-acceptor energy transfer, after contacting the cleavage enzyme with each of the library members of the tandem fluorescent peptide construct. A degree of donor-acceptor energy transfer that is lower than an expected amount indicates the presence of a linker sequence that is cleaved by the enzyme. The degree of donor-acceptor energy transfer in the sample can be determined, for example, as a function of the amount of fluorescence from the donor moiety, the amount of fluorescence from the acceptor donor moiety, or the ratio of the amount of fluorescence from the donor moiety to the amount of fluorescence from the acceptor moiety or the excitation state lifetime of the donor moiety.

In the tandem constructs of the invention, the donor and acceptor moieties are connected through a linker moiety. The linker moiety, preferably, includes a peptide moiety, but can be or can include another organic molecular moiety, as well. In a preferred embodiment, the linker moiety includes a cleavage recognition site specific for an enzyme or other cleavage agent of interest. A cleavage site in the linker moiety is useful because when a tandem construct is mixed with the cleavage agent, the linker is a substrate for cleavage by the cleavage agent. Rupture of the linker moiety results in separation of the fluorophore and the quencher of the invention. The separation is measurable as a change in donor-acceptor energy transfer. Alternatively, peptide assembly can be detected by an increase in donor-acceptor energy transfer between a peptide fragment bearing a BHQ and a peptide fragment bearing a donor moiety.

When the cleavage agent of interest is a protease, the linker generally includes a peptide containing a cleavage recognition sequence for the protease. A cleavage recognition sequence for a protease is a specific amino acid sequence recognized by the protease during proteolytic cleavage. Many protease cleavage sites are known in the art, and these and other cleavage sites can be included in the linker moiety. See, e.g., Matayoshi et al. *Science* 247: 954 (1990); Dunn et al. *Meth. Enzymol.* 241: 254 (1994); Seidah et al. *Meth. Enzymol.* 244: 175 (1994); Thornberry, *Meth. Enzymol.* 244: 615 (1994); Weber et al. *Meth. Enzymol.* 244: 595 (1994); Smith et al. *Meth. Enzymol.* 244: 412 (1994); Bouvier et al. *Meth. Enzymol.* 248: 614 (1995), Hardy et al., in AMYLOID PROTEIN PRECURSOR IN DEVELOPMENT, AGING, AND ALZHEIMER'S DISEASE, ed. Masters et al. pp. 190-198 (1994).

Solid Support Immobilized BHQ Analogues

The BHQs of the invention can be immobilized on substantially any polymer, biomolecule, and solid or semi-solid material having any useful configuration. Moreover, any conjugate comprising one or more BHQs can be similarly immobilized. When the support is a solid or semi-solid, examples of preferred types of supports for immobilization of the nucleic acid probe include, but are not limited to, controlled pore glass, glass plates, polystyrene, avidin coated polystyrene beads, cellulose, nylon, acrylamide gel and activated dextran. These solid supports are preferred because of their chemical stability, ease of functionalization and well-defined surface area. Solid supports such as, controlled pore glass (CPG, 500 Å, 1000 Å) and non-swelling high cross-linked polystyrene (1000 Å) are particularly preferred.

According to the present invention, the surface of a solid support is functionalized with a quencher of the invention or a species including a quencher of the invention. For clarity of illustration, the following discussion focuses on attaching a reactive BHQ to a solid support. The following discussion is also broadly relevant to attaching a species that includes within its structure a reactive BHQ to a solid support, and the attachment of such species and reactive BHQ analogues to other molecules and structures.

The BHQs are preferably attached to a solid support by forming a bond between a reactive group on the BHQ and a reactive group on the surface of the solid support or a linker attached to the solid support, thereby derivatizing the solid support with one or more BHQ analogues. The bond between the solid support and the BHQ is preferably a covalent bond, although ionic, dative and other such bonds are useful as well. Reactive groups which can be used in practicing the present invention are discussed in detail above and include, for example, amines, hydroxyl groups, carboxylic acids, carboxylic acid derivatives, alkenes, sulfhydryls, siloxanes, etc.

A large number of solid supports appropriate for practicing the present invention are available commercially and include, for example, peptide synthesis resins, both with and without attached amino acids and/or peptides (e.g., alkoxybenzyl alcohol resin, aminomethyl resin, aminopolystyrene resin, benzhydrylamine resin, etc. (Bachem)), functionalized controlled pore glass (BioSearch Technologies, Inc.), ion exchange media (Aldrich), functionalized membranes (e.g., —COOH membranes; Asahi Chemical Co., Asahi Glass Co., and Tokuyama Soda Co.), and the like.

Moreover, for applications in which an appropriate solid support is not commercially available, a wide variety of reaction types are available for the functionalization of a solid support surface. For example, supports constructed of a plastic such as polypropylene, can be surface derivatized by chromic acid oxidation, and subsequently converted to hydroxylated or aminomethylated surfaces. The functionalized support is then reacted with a BHQ of complementary reactivity, such as a BHQ active ester, acid chloride or sulfonate ester, for example. Supports made from highly crosslinked divinylbenzene can be surface derivatized by chloromethylation and subsequent functional group manipulation. Additionally, functionalized substrates can be made from etched, reduced polytetrafluoroethylene.

When the support is constructed of a siliceous material such as glass, the surface can be derivatized by reacting the surface Si—OH, SiO—H, and/or Si—Si groups with a functionalizing reagent.

In a preferred embodiment, wherein the substrates are made from glass, the covalent bonding of the reactive group to the glass surface is achieved by conversion of groups on the substrate's surface by a silicon-modifying reagent such as:

$$(R^aO)_3-Si-R^b-X^a \quad \quad \text{(VII)}$$

where $R^a$ is an alkyl group, such as methyl or ethyl, $R^b$ is a linking group between silicon and $X^a$, and $X^a$ is a reactive group or a protected reactive group. Silane derivatives having halogens or other leaving groups beside the displayed alkoxy groups are also useful in the present invention.

In another preferred embodiment, the reagent used to functionalize the solid support provides for more than one reactive group per each reagent molecule. Using reagents, such as the compound below, each reactive site on the substrate surface is, in essence, "amplified" to two or more functional groups:

 (VIII)

where $R^a$ is an alkyl group (e.g., methyl, ethyl), $R^b$ is a linking group between silicon and $X^a$, $X^a$ is a reactive group or a protected reactive group and n is an integer between 2 and 50, and more preferably between 2 and 20. The amplification of a BHQ by its attachment to a silicon-containing substrate is intended to be exemplary of the general concept of BHQ amplification. This amplification strategy is equally applicable to other aspects of the invention in which a BHQ analogue is attached to another molecule or solid support.

A number of siloxane functionalizing reagents can be used, for example:
1. Hydroxyalkyl siloxanes (Silylate surface, functionalize with diborane, and $H_2O_2$ to oxidize to the alcohol)
   a. allyl trichlorosilane→→3-hydroxypropyl
   b. 7-oct-1-enyl trichlorchlorosilane→→8-hydroxyoctyl
2. Diol (dihydroxyalkyl) siloxanes (silylate surface and hydrolyze to diol) a. (glycidyl trimethoxysilane→→(2, 3-dihydroxypropyloxy)propyl
3. Aminoalkyl siloxanes (amines requiring no intermediate functionalizing step)
   a. 3-aminopropyl trimethoxysilane→aminopropyl
4. Dimeric secondary aminoalkyl siloxanes
   a. bis(3-trimethoxysilylpropyl)amine→bis(silyloxylpropyl)amine It will be apparent to those of skill in the art that an array of similarly useful functionalizing chemistries is available when support components other than siloxanes are used. Thus, for example alkyl thiols, functionalized as discussed above in the context of siloxane-modifying reagents, can be attached to metal films and subsequently reacted with a BHQ to produce the immobilized compound of the invention.

R groups of use for $R^b$ in the above described embodiments of the present invention include, but are not limited to, alkyl, substituted alkyl, aryl, arylalkyl, substituted aryl, substituted arylalkyl, acyl, halogen, hydroxy, amino, alkylamino, acylamino, alkoxy, acyloxy, aryloxy, aryloxyalkyl, mercapto, saturated cyclic hydrocarbon, unsaturated cyclic hydrocarbon, heteroaryl, heteroarylalkyl, substituted heteroaryl, substituted heteroarylalkyl, heterocyclic, substituted heterocyclic and heterocyclicalkyl groups and combinations thereof.

Nucleic Acid Capture Probes

In one embodiment, an immobilized nucleic acid comprising a BHQ is used as a capture probe. The nucleic acid probe can be attached directly to a solid support, for example by attachment of the 3'- or 5'-terminal nucleotide of the probe to the solid support. More preferably, however, the probe is attached to the solid support by a linker (i.e., spacer arm, supra). The linker serves to distance the probe from the solid support. The linker is most preferably from about 5 to about 30 atoms in length, more preferably from about 10 to about 50 atoms in length.

In yet another preferred embodiment, the solid support is also used as the synthesis support in preparing the probe. The length and chemical stability of the linker between the solid support and the first 3'-unit of nucleic acid play an important role in efficient synthesis and hybridization of support bound nucleic acids. The linker arm should be sufficiently long so that a high yield (>97%) can be achieved during automated synthesis. The required length of the linker will depend on the particular solid support used. For example, a six atom linker is generally sufficient to achieve a >97% yield during automated synthesis of nucleic acids when high cross-linked polystyrene is used as the solid support. The linker arm is preferably at least 20 atoms long in order to attain a high yield (>97%) during automated synthesis when CPG is used as the solid support.

Hybridization of a probe immobilized on a solid support generally requires that the probe be separated from the solid support by at least 30 atoms, more preferably at least 50 atoms. In order to achieve this separation, the linker generally includes a spacer positioned between the linker and the 3'-terminus. For nucleic acid synthesis, the linker arm is usually attached to the 3'-OH of the 3'-terminus by an ester linkage which can be cleaved with basic reagents to free the nucleic acid from the solid support.

A wide variety of linkers are known in the art, which may be used to attach the nucleic acid probe to the solid support. The linker may be formed of any compound, which does not significantly interfere with the hybridization of the target sequence to the probe attached to the solid support. The linker may be formed of, for example, a homopolymeric nucleic acid, which can be readily added on to the linker by automated synthesis. Alternatively, polymers such as functionalized polyethylene glycol can be used as the linker. Such polymers are presently preferred over homopolymeric nucleic acids because they do not significantly interfere with the hybridization of probe to the target nucleic acid. Polyethylene glycol is particularly preferred because it is commercially available, soluble in both organic and aqueous media, easy to functionalize, and completely stable under nucleic acid synthesis and post-synthesis conditions.

The linkages between the solid support, the linker and the probe are preferably not cleaved during synthesis or removal of base protecting groups under basic conditions at high temperature. These linkages can, however, be selected from groups that are cleavable under a variety of conditions. Examples of presently preferred linkages include carbamate, ester and amide linkages.

Acrylamide-Immobilized Probes

In another preferred embodiment, a species is within a matrix, such as an acrylamide matrix and the species bears a BHQ, or the presence of the immobilized species is ascertained using a probe bearing a BHQ. In a preferred embodiment, the immobilization is accomplished in conjunction with the "acrydite" process invented and commercialized by Mosaic Technologies (Cambridge, Mass., see, Rehman et al., *Nucleic Acids Research*, 27: 649-655 (1999)). The acrydite method allows immobilization of alkene labeled capture probes within a polymerized polyacrylamide network. When target mixes are run past the immobilized probe band under electrophoresis conditions, the target nucleic acid is captured substantially quantitatively. However, detection of this event currently requires a second probe. In one embodiment, probes bearing a BHQ, and/or a fluorophore, are immobilized in an acrylamide matrix and subsequently contacted with the target mix. By using fluorescent probes as capture probes, signals from target mixes can be directly detected in real time.

Microarrays

The present invention also provides microarrays including immobilized BHQs and compounds (e.g., peptides, nucleic acids, bioactive agents, etc.) functionalized with BHQs. Moreover, the invention provides methods of interrogating microarrays using probes that are functionalized with BHQs.

The immobilized species and the probes are selected from substantially any type of molecule, including, but not limited to, small molecules, peptides, enzymes nucleic acids and the like.

Nucleic acid microarrays consisting of a multitude of immobilized nucleic acids are revolutionary tools for the generation of genomic information, see, Debouck et al., in supplement to *Nature Genetics,* 21:48-50 (1999). The discussion that follows focuses on the use of BHQs in conjunction with nucleic acid microarrays. This focus is intended to be illustrative and does not limit the scope of materials with which this aspect of the present invention can be practiced.

In another preferred embodiment, the compounds of the present invention are utilized in a microarray format. The BHQs, or species bearing BHQs can themselves be components of a microarray or, alternatively they can be utilized as a tool to screen components of a microarray.

Thus, in a preferred embodiment, the present invention provides a method of screening a microarray. The method includes contacting the members of the microarray with, for example, a BHQ-bearing probe and interrogating the microarray for regions of fluorescence. In an exemplary embodiment, fluorescent regions are indicative of the presence of an interaction between the BHQ-bearing probe and a microarray component. In another version of this method, the microarray is interrogated for regions in which fluorescence is quenched by the BHQ, again indicating the presence of an interaction between the BHQ-bearing probe and a component of the microarray.

In another preferred embodiment, the array comprises immobilized BHQ-bearing donor-acceptor energy transfer probes as the interrogating species. In this embodiment, the probe "turns on" when hybridized to its target. Such arrays are easily prepared and read, and can be designed to give quantitative data. Arrays comprising BHQ-bearing probes are valuable tools for expression analysis and clinical genomic screening.

In another preferred embodiment, the immobilized BHQ-bearing probe is not a donor-acceptor energy transfer probe. A microarray based on such as format can be used to probe for the presence of interactions between an analyte and the immobilized probe by, for example, observing the quenching of analyte fluorescence upon interaction between the probe and analyte.

In a further preferred embodiment, the microarrays comprise n regions that comprise identical or different species (e.g., nucleic acid sequences, bioactive agents). For example, the microarray can comprise a mixture of n regions comprising groups of identical species. In a preferred embodiment, n is a number from 2 to 100, more preferably, from 10 to 1,000, and more preferably from 100 to 10,000. In a still further preferred embodiment, the n regions are patterned on a substrate as n distinct locations in a manner that allows the identity of each of the n locations to be ascertained.

In yet another preferred embodiment, the invention also provides a method for preparing a microarray of n BHQ-bearing probes. The method includes attaching BHQ-bearing probes to selected regions of a substrate. A variety of methods are currently available for making arrays of biological macromolecules, such as arrays nucleic acid molecules. The following discussion focuses on the assembly of a microarray of BHQ-bearing probes, this focus is for reasons of brevity and is intended to be illustrative and not limiting.

One method for making ordered arrays of BHQ-bearing probes on a substrate is a "dot blot" approach. In this method, a vacuum manifold transfers a plurality, e.g., 96, aqueous samples of probes from 3 millimeter diameter wells to a substrate. The probe is immobilized on the porous membrane by baking the membrane or exposing it to UV radiation. A common variant of this procedure is a "slot-blot" method in which the wells have highly-elongated oval shapes.

Another technique employed for making ordered arrays of probes uses an array of pins dipped into the wells, e.g., the 96 wells of a microtiter plate, for transferring an array of samples to a substrate, such as a porous membrane. One array includes pins that are designed to spot a membrane in a staggered fashion, for creating an array of 9216 spots in a 22×22 cm area. See, Lehrach, et al., HYBRIDIZATION FINGERPRINTING IN GENOME MAPPING AND SEQUENCING, GENOME ANALYSIS, Vol. 1, Davies et al, Eds., Cold Springs Harbor Press, pp. 39-81 (1990).

An alternate method of creating ordered arrays of probes is analogous to that described by Pirrung et al. (U.S. Pat. No. 5,143,854, issued 1992), and also by Fodor et al., (*Science,* 251: 767-773 (1991)). This method involves synthesizing different probes at different discrete regions of a particle or other substrate. This method is preferably used with relatively short probe molecules, e.g., less than 20 bases. A related method has been described by Southern et al. (*Genomics,* 13: 1008-1017 (1992)).

Khrapko, et al., *DNA Sequence,* 1: 375-388 (1991) describes a method of making an nucleic acid matrix by spotting DNA onto a thin layer of polyacrylamide. The spotting is done manually with a micropipette.

The substrate can also be patterned using techniques such as photolithography (Kleinfield et al., *J. Neurosci.* 8:4098-120 (1998)), photoetching, chemical etching and microcontact printing (Kumar et al., *Langmuir* 10:1498-511 (1994)). Other techniques for forming patterns on a substrate will be readily apparent to those of skill in the art.

The size and complexity of the pattern on the substrate is limited only by the resolution of the technique utilized and the purpose for which the pattern is intended. For example, using microcontact printing, features as small as 200 nm are layered onto a substrate. See, Xia, Y., *J. Am. Chem. Soc.* 117:3274-75 (1995). Similarly, using photolithography, patterns with features as small as 1 μm are produced. See, Hickman et al., *J. Vac. Sci. Technol.* 12:607-16 (1994). Patterns which are useful in the present invention include those which include features such as wells, enclosures, partitions, recesses, inlets, outlets, channels, troughs, diffraction gratings and the like.

In a presently preferred embodiment, the patterning is used to produce a substrate having a plurality of adjacent wells, indentations or holes to contain the probes. In general, each of these substrate features is isolated from the other wells by a raised wall or partition and the wells do not readily fluidically communicate. Thus, a particle, reagent or other substance, placed in a particular well remains substantially confined to that well. In another preferred embodiment, the patterning allows the creation of channels through the device whereby an analyte or other substance can enter and/or exit the device.

In another embodiment, the probes are immobilized by "printing" them directly onto a substrate or, alternatively, a "lift off" technique can be utilized. In the lift off technique, a patterned resist is laid onto the substrate, and a probe is laid down in those areas not covered by the resist and the resist is subsequently removed. Resists appropriate for use with the substrates of the present invention are known to those of skill in the art. See, for example, Kleinfield et al., *J. Neurosci.* 8:4098-120 (1998). Following removal of the photoresist, a second probe, having a structure different from the first probe can be bonded to the substrate on those areas initially covered by the resist. Using this technique, substrates with patterns of probes having different characteristics can be produced.

Similar substrate configurations are accessible through microprinting a layer with the desired characteristics directly onto the substrate. See, Mrkish et al. *Ann. Rev. Biophys. Biomol. Struct.* 25:55-78 (1996).

Spacer Groups

As used herein, the term "spacer group," refers to constituents of BHQ-bearing probes. The spacer group links donor and/or acceptor moieties and other groups to the nucleic acid, peptide or other component of the probe. The spacer groups can be hydrophilic (e.g., tetraethylene glycol, hexaethylene glycol, polyethylene glycol) or they can be hydrophobic (e.g., hexane, decane, etc.).

In a preferred embodiment, using solid supports the immobilized construct includes a spacer between the solid support reactive group and the BHQ analogue. The linker is preferably selected from $C_6$-$C_{30}$ alkyl groups, $C_6$-$C_{30}$ substituted alkyl groups, polyols, polyethers (e.g., poly(ethyleneglycol)), polyamines, polyamino acids, polysaccharides and combinations thereof.

In certain embodiments, it is advantageous to have the donor and/or acceptor of the probe attached to another polymeric component by a group that provides flexibility and distance from the polymeric component. Using such spacer groups, the properties of the donor and/or acceptor adjacent to another probe component is modulated. Properties that are usefully controlled include, for example, hydrophobicity, hydrophilicity, surface-activity, the distance of the donor and/or BHQ moiety from the other probe components (e.g., carrier molecule) and the distance of the donor from the BHQ.

In an exemplary embodiment, the spacer serves to distance the BHQ from a nucleic acid. Spacers with this characteristic have several uses. For example, a BHQ held too closely to the nucleic acid may not interact with the donor group, or it may interact with too low of an affinity. When a BHQ is itself sterically demanding, the interaction leading to quenching can be undesirably weakened, or it may not occur at all, due to a sterically-induced hindering of the approach of the two components.

When the construct comprising the BHQ is immobilized by attachment to, for example, a solid support, the construct can also include a spacer moiety between the reactive group of the solid support and the BHQ analogue, or other probe component bound to the solid support.

In yet a further embodiment, a spacer group used in the probes of the invention is provided with a group that can be cleaved to release a bound moiety, such as, for example, a BHQ, fluorophore, minor groove binder, intercalating moiety, and the like from the polymeric component. Many cleaveable groups are known in the art. See, for example, Jung et al., *Biochem. Biophys. Acta,* 761: 152-162 (1983); Joshi et al., *J. Biol. Chem.*, 265: 14518-14525 (1990); Zarling et al., *J. Immunol.*, 124: 913-920 (1980); Bouizar et al., *Eur. J. Biochem.*, 155: 141-147 (1986); Park et al., *J. Biol. Chem.*, 261: 205-210 (1986); Browning et al., *J. Immunol.*, 143: 1859-1867 (1989). Moreover a broad range of cleavable, bifunctional (both homo- and hetero-bifunctional) spacer arms are commercially available from suppliers such as Pierce.

An exemplary embodiment utilizing spacer groups is set forth in Formulae VII and VIII, above. In these formulae, $R^b$ is either stable or it can be cleaved by chemical or photochemical reactions. For example, $R^b$ groups comprising ester or disulfide bonds can be cleaved by hydrolysis and reduction, respectively. Also within the scope of the present invention is the use of $R^b$ groups which are cleaved by light such as, for example, nitrobenzyl derivatives, phenacyl groups, benzoin esters, etc. Other such cleaveable groups are well-known to those of skill in the art.

Kits

In another aspect, the present invention provides kits containing one or more of the BHQs or BHQ-bearing compositions of the invention. In one embodiment, a kit will include a reactive BHQ derivative and directions for attaching this derivative to another molecule. In another embodiment, the kit includes a BHQ-labeled nucleic acid that optionally is also labeled with a fluorophore and directions for using this nucleic acid in one or more assay formats. Other formats for kits will be apparent to those of skill in the art and are within the scope of the present invention.

The materials and methods of the present invention are further illustrated by the examples which follow. These examples are offered to illustrate, but not to limit the claimed invention.

EXAMPLES

The following Examples illustrate the synthesis and characterization of exemplary species of the invention.

Example 1 sets for the synthesis of the quencher BH1 and its conversion into a controlled pore glass conjugate. Examples 2 and 3, provide similar details regarding the quenchers BH2 and BH3.

Example 4 sets forth the incorporation of exemplary quenchers of the invention into nucleic acid-based donor-acceptor energy transfer probes. The quenching efficiency of the BHQs in the probes is assessed and compared to that of the art-recognized dark quencher DABCYL.

Example 1

This Example sets forth the synthesis and characterization of BH1 and derivatives thereof.

1.1 Synthesis of 4-methyl-2-nitrobenzylazo-2'-methyl-5'-nitrobenzylazo-4"-N,N-di(2-hydroxyethyl) azobenzene, (BH1 diol), 6

To a rapidly stirred suspension of 25 g (60 mmol) Fast Corinth V salt (Aldrich 22, 736-5) in 400 mL of chilled water (ice bath) was added 50 g (276 mmol) N-phenyldiethanolamine dissolved in 400 mL methanol and 300 mL sat'd $NaHCO_3$ over 20 min. The mixture changed color from yellow to deep red during the course of the addition. The mixture was chilled for an additional 1 hr after addition, then filtered through a medium glass frit. The dark red solid was washed with 300 ml of ice cold water and air dried for 3 days. The yield of 6 was 27 g, (91%). TLC rf 0.15 (Silica plate, 5% MeOH in $CH_2Cl_2$). MALDI M/e 493.11 (Calc'd 492.5). $^1$H NMR ($CDCl_3$, δ) 7.9 (d, 2H), 7.65 (m, 2H), 7.6 (s, 1H), 7.45 (d, 1H), 7.4 (s, 1H), 6.8 (d, 2H), 4.0 (s, 3H), 3.95 (t, 2H), 3.85 (t, 2H), 3.7 (t, 2H), 3.6 (t, 2H), 2.7 (s, 3H), 2.5 (s, 3H).

1.2 Synthesis of 4-methyl-2-nitrobenzylazo-2'-methyl-5'-nitrobenzylazo-4"-N,N-(2-hydroxyethyl)-(2-O-(4,4'dimethoxytrityl)ethylazobenzene (DMT-BH1), 7

A solution of 25 g (50 mmol) 6 in 400 mL of dry pyridine was stripped to dryness, and 7 g (21 mmol) of DMT-chloride was added in 300 mL of dry pyridine. The solution sat for 3 days at rt, then was stripped to a tar. The black residue was dissolved in 600 mL ethyl acetate, and washed with 300 mL of 1 N aqueous citric acid, followed by a 300 mL sat'd aqueous $NaHCO_3$ wash. The organic layer was dried over $MgSO_4$ and stripped to a tar. The residue was loaded onto a 55 by 8 cm chromatography column of neutral alumina, 7% by weight water, and eluted first with a mobile phase of 0.5% MeOH, 0.5% pyridine in $CH_2Cl_2$. After 1 L of solvent eluted, a gradient to 2% MeOH was run over 4 L. Fractions containing pure 7 (0.42 rf, silica plate, 2% MeOH, 2% pyridine in $CH_2Cl_2$) were pooled and evaporated. The yield was 2.8 g (17% yield) of 2 as a dark foam. MALDI M/e 793.88 (Calc'd 794.5). $^1$H NMR ($CDCl_3$, δ) 7.85 (d, 2H), 7.7 (m, 4H), 7.6 (s, 1H), 7.45 (d, 1H), 7.4-7.1 (m, 10H), 6.8 (m, 6H), 4.0 (s, 3H), 3.85 (m, 2H), 3.75 (s, 6H), 3.7 (m, 2H), 3.5-3.3 (m, 4H), 2.7 (s, 3H), 2.5 (s, 3H).

1.3 Synthesis of 4-methyl-2-nitrobenzylazo-2'-methyl-5'-nitrobenzylazo-4"-N,N-(2-O—(N',N'-diisopropyl-2-cyanoethylphosphite)ethyl)-(2-O-4,4'dimethoxytrityl)-ethyl)azobenzene, (DMT-BH1 amidite), 8

A solution of 2.8 g (3.5 mmol) of 7 in 50 mL of dry pyridine was evaporated to dryness and high vacuum applied for several hrs. A solution of 1.5 g (5 mmol) of N,N,N',N'-tetraisopropyl-2-cyanoethylphosphane and 60 mg of tetrazole were mixed in 20 mL of dry acetonitrile and added to the flask containing the dried 7. After 2 hrs, the solvent was stripped, and the residue was dissolved in 200 mL of EtOAc. The organic layer was washed with 100 mL sat'd aqueous $NaHCO_3$ and dried over $MgSO_4$. The solvent was evaporated, and the residue applied to a 25 by 3 cm chromatography column of neutral alumina, 7% by weight water, and eluted with a mobile phase of 75% Pet. ether, 23% EtOAc, 2% pyridine. Fractions containing pure 8 (0.67 rf, pre-run silica plate, 50% Pet. ether, 48% EtOAc, 2% pyridine) were pooled and evaporated. The yield was 1 g (20% yield) of 8 as a dark foam. MALDI M/e 995.5 (Calc'd 994.5).

1.4 Synthesis of BH1-CPG, 9

11 g DMT-2,2'-sulfonyldiethanol-succinyl controlled pore glass, 500 Å, Biosearch part # BGS-5000, was washed three times with 3% dichloroacetic acid to effect removal of the DMT group. The CPG was washed well with three 50 mL portions of $CH_2Cl_2$, followed by one 50 mL wash with dry pyridine. The CPG was added to the flask containing 1 g of 8. 25 mL of dry pyridine was added, and the solvent was removed by rotary evaporation, followed by high vacuum for 3 hrs. The dried CPG and amidite were treated with a solution of 1 g S-ethyl tetrazole in 20 mL of dry acetonitrile for 20 min. The CPG was washed in a sintered glass funnel twice with 50 mL of acetonitrile, then 50 mL of 0.02 M iodine in 90% THF, 8% water and 2% pyridine were added. After 5 min, the iodine solution was washed out of the CPG with three 50 mL portions of acetonitrile, then a capping solution of 10% $Ac_2O$, 10% N-methylimidazole and 10% pyridine in THF was added. After 20 min, the solution was washed out of the CPG with three 50 mL portions of acetonitrile, followed by three 50 mL portions of $CH_2Cl_2$. The material was dried overnight under high vacuum. DMT loading determination on the dried material was 16 μM/g.

Example 2

This Example sets forth the synthesis and characterization of BH2 and derivatives thereof.

2.1 Synthesis of 4-nitrobenzylazo-2',5'-dimethoxybenzylazo-4"-N,N-di(2-hydroxyethyl) azobenzene, (BH2 diol), 10

To a rapidly stirred suspension of 25 g (60 mmol) Fast Black K salt (Aldrich 20, 151-0) in 400 mL of chilled water (ice bath) was added 50 g (276 mmol) N-phenyldiethanolamine dissolved in 400 mL methanol and 300 mL sat'd $NaHCO_3$ over 20 min. The mixture changed color from brown to deep blue during the course of the addition. The mixture was chilled for an additional 1 hr after addition, then filtered through a medium glass frit. The dark blue solid was washed with 300 ml of ice cold water and air dried for 3 days. The yield of 10 was 22 g, (74%). TLC rf 0.2 (Silica plate, 5% MeOH in $CH_2Cl_2$). MALDI M/e 493.13 (Calc'd 494.4). $^1$H NMR ($CDCl_3$, δ) 8.3 (d, 2H), 8.0 (d, 2H), 7.85 (d, 2H), 7.4 (d, 2H), 6.7 (m, 2H), 4.1 (s, 3H), 3.95 (s, 3H), 3.9 (t, 2H), 3.8 (t, 2H), 3.7 (t, 2H), 3.5 (t, 3H).

2.2 Synthesis of 4-nitrobenzylazo-2',5'-dimethoxybenzylazo-4"-N,N-(2-hydroxy-ethyl)-(2-O-(4,4' dimethoxytrityl)ethylazobenzene 1, (DMT-BH2), 11

A solution of 22 g (44 mmol) 10 in 400 mL of dry pyridine was stripped to dryness, and 7 g (21 mmol) of DMT-chloride was added in 300 mL of dry pyridine. The solution sat for 3 days at rt, then was stripped to a tar. The black residue was dissolved in 600 mL ethyl acetate, and washed with 300 mL of 1 N aqueous citric acid, followed by a 300 mL sat'd aqueous $NaHCO_3$ wash. The organic layer was dried over $MgSO_4$ and stripped to a tar. The residue was loaded onto a 55 by 8 cm chromatography column of neutral alumina, 7% by weight water, and eluted first with a mobile phase of 0.5% MeOH, 0.5% pyridine in $CH_2Cl_2$. After 1 L of solvent eluted, a gradient to 2% MeOH was run over 4 L. Fractions containing pure 11 (0.4 rf, silica plate, 2% MeOH, 2% pyridine in $CH_2Cl_2$) were pooled and evaporated. The yield was 2.8 g (17% yield) of 11 as a dark foam. MALDI M/e 794.2 (Calc'd 796.4). $^1$H NMR ($CDCl_3$, δ) 8.3 (d, 2H), 7.9 (d, 2H), 7.75 (d, 2H), 7.4-7.1 (m, 9H), 6.7-6.5 (m, 6H), 4.1 (s, 3H), 3.95 (s, 3H), 3.9-3.6 (m, 12H), 3.3 (t, 3H).

2.3 Synthesis of 4-nitrobenzylazo-2',5'-dimethoxybenzylazo-4"-N,N-(2-O—(N',N'-diisopropyl-2-cyanoethylphosphite)ethyl)-(2-O-(4,4'dimethoxy-trityl) ethyl)-azobenzene, (DMT-BH2 amidite), 12

A solution of 2.8 g (3.5 mmol) 11 in 50 mL of dry pyridine was evaporated to dryness and high vacuum applied for several hrs. A solution of 1.5 g (5 mmol) of N,N,N',N'-tetraisopropyl-2-cyanoethylphosphane and 60 mg of tetrazole were mixed in 20 mL of dry acetonitrile and added to the flask containing the dried 11. After 2 hrs, the solvent was stripped, and the residue was dissolved in 200 mL of EtOAc. The organic layer was washed with 100 mL sat'd aqueous $NaHCO_3$ and dried over $MgSO_4$. The solvent was evaporated, and the residue applied to a 25 by 3 cm chromatography column of neutral alumina, 7% by weight water, and eluted with a mobile phase of 75% Pet. ether, 23% EtOAc, 2% pyridine. Fractions containing pure 12 (0.71 rf, pre-run silica plate, 50% Pet. ether, 48% EtOAc, 2% pyridine) were pooled and evaporated. The yield was 1 g (20% yield) of 11 as a dark foam. MALDI M/e 996.06 (Calc'd 996.4).

2.4 Synthesis of BH2-CPG, 13

10 g DMT-2,2'-sulfonyldiethanol-succinyl controlled pore glass, 500 Å, Biosearch part # BG5-5000, was washed three times with 3% dichloroacetic acid to effect removal of the DMT group. The CPG was washed well with three 50 mL portions of $CH_2Cl_2$, followed by one 50 mL wash with dry pyridine. The CPG was added to the flask containing 1 g of 12.

25 mL of dry pyridine was added, and the solvent was removed by rotary evaporation, followed by high vacuum for 3 hrs. The dried CPG and amidite were treated with a solution of 1 g S-ethyl tetrazole in 20 mL of dry acetonitrile for 20 min. The CPG was washed in a sintered glass funnel twice with 50 mL of acetonitrile, then 50 mL of 0.02 M iodine in 90% THF, 8% water and 2% pyridine were added. After 5 min, the iodine solution was washed out of the CPG with three 50 mL portions of acetonitrile, then a capping solution of 10% Ac$_2$O, 10% N-methylimidazole and 10% pyridine in THF was added. After 20 min, the solution was washed out of the CPG with three 50 mL portions of acetonitrile, followed by three 50 mL portions of CH$_2$Cl$_2$. The material was dried overnight under high vacuum. DMT loading determination on the dried material was 30 µM/g.

Example 3

This Example sets forth the synthesis and characterization of BH3 and derivatives thereof.

3.1 Synthesis of 3-diethylamino-5-phenylphenazium-7-(4'-N,N-di(2-hydroxyethyl) azobenzene) chloride, (BH3 diol), 14

3-amino-7-(diethylamino)-5-phenylphenazium chloride (methylene violet 3RAX, Aldrich 30, 750-5), 10 g (26 mmol) was stirred in 200 mL 1 N HCl while in an ice bath. A solution of 2 g NaNO$_2$ in 20 mL of cold water was added dropwise over 20 min. The solution was stirred for 30 min. N-phenyldiethanolamine, 4.7 g (27 mmol), was dissolved in 100 mL of methanol and added to the methylene violet solution, after the pH was adjusted to 6 with NaOH solution. The solution changed color from violet to dark green. The solution was stirred for 1 hr, then extracted three times with 200 mL of CH$_2$Cl$_2$. The aqueous layer was evaporated, and the dark green solid was triturated with 3 200 mL portions of pyridine. The pyridine was evaporated to give 2.9 g (21% yield) of 14 as a dark green solid. (0.85 rf, silica plate, 15% MeOH, 2% pyridine in CH$_2$Cl$_2$) MALDI M/e 535.6 (calc'd 535.75).

3.2 Synthesis of 3-diethylamino-5-phenylphenazium-7-(4'-N,N-(2-hydroxyethyl)-(2-O-(4,4'dimethoxytrityl)ethylazobenzene chloride, (DMT-BH3), 15

Compound 14, 2.9 g (5.4 mmol) was dried by stripping with 100 mL dry pyridine, and then re-dissolved in 100 mL dry pyridine along with 2 g (5.9 mmol) of DMT chloride. The mixture sat overnight, and the solvent was stripped. The residue was re-dissolved in 200 mL CH$_2$Cl$_2$ and washed with 200 mL 1 M aqueous citric acid. The aqueous layer was back-washed with two 200 mL portions of CH$_2$Cl$_2$, and the combined organic layers were evaporated to a tar. The residue was loaded onto a 20 by 3 cm chromatography column of neutral alumina, 7% by weight water, and eluted first with a mobile phase of 2% MeOH, 1% pyridine in CH$_2$Cl$_2$. A gradient to 6% MeOH was run over 3 L. Fractions containing pure 15 (0.9 rf, silica plate, 15% MeOH, 1% pyridine in CH$_2$Cl$_2$) were pooled and evaporated. The yield was 0.5 g (11% yield) of 15 as a dark foam. MALDI M/e 837.6 (calc'd 836.75)

3.3 Synthesis of 3-diethylamino-5-phenylphenazium-7-(4'-N,N-(2-O—(N',N'-diisopropyl-2-cyanoethylphosphite)ethyl)-(2-O-(4,4'dimethoxy-trityl)ethyl)azobenzene chloride, (DMT-BH3 amidite), 16

A solution of 0.5 g (0.6 mmol) 15 in 50 mL of dry pyridine was evaporated to dryness and high vacuum applied for several hrs. A solution of 0.5 g (1.7 mmol) of N,N,N',N'-tetraisopropyl-2-cyanoethylphosphane and 20 mg of tetrazole were mixed in 20 mL of dry acetonitrile and added to the flask containing the dried 15. After 2 hrs, the solvent was stripped, and the residue was dissolved in 100 mL of EtOAc. The organic layer was washed with 50 mL sat'd aqueous NaHCO$_3$ and dried over MgSO$_4$. The solvent was evaporated, and the residue applied to a 15 by 3 cm chromatography column of neutral alumina, 7% by weight water, and eluted first with a mobile phase of 1% MeOH, 1% pyridine in CH$_2$Cl$_2$. A gradient to 6% MeOH was run over 2 L. Fractions containing pure 16 (0.82 rf, pre-run silica plate, 5% MeOH, 1% pyridine in CH$_2$Cl$_2$) were pooled and evaporated. The yield was 0.26 g (42% yield) of 16 as a dark foam. MALDI M/e 1037.3 (Calc'd 1036.75).

Synthesis of BH3-CPG, 17

2 g DMT-2,2'-sulfonyldiethanol-succinyl controlled pore glass, 500 Å, Biosearch part # BG5-5000, was washed three times with 3% dichloroacetic acid to effect removal of the DMT group. The CPG was washed well with three 20 mL portions of CH$_2$Cl$_2$, followed by one 20 mL wash with dry pyridine. The CPG was added to the flask containing 0.26 g of 16. 25 mL of dry pyridine was added, and the solvent was removed by rotary evaporation, followed by high vacuum for 3 hrs. The dried CPG and amidite were treated with a solution of 0.5 g S-ethyl tetrazole in 10 mL of dry acetonitrile for 20 min. The CPG was washed in a sintered glass funnel twice with 20 mL of acetonitrile, then 20 mL of 0.02 M iodine in 90% THF, 8% water and 2% pyridine were added. After 5 min, the iodine solution was washed out of the CPG with three 20 mL portions of acetonitrile, then a capping solution of 10% Ac$_2$O, 10% N-methylimidazole and 10% pyridine in THF was added. After 20 min, the solution was washed out of the CPG with three 20 mL portions of acetonitrile, followed by three 20 mL portions of CH$_2$Cl$_2$. The material was dried overnight under high vacuum. DMT loading determination on the dried material was 12 µM/g.

Example 4

This Example sets forth the preparation and characterization of nucleic acid analogues of exemplary BHQs of the invention. The nucleic acid-BHQ conjugates are compared to a similar conjugate of DABCYL.

The efficiency of donor-acceptor energy transfer (FRET) is inversely proportional to the sixth power of the distance between the donor and acceptor molecules (Stryer, L. *Annu. Rev. Biochem.* 1978, 47, 819-846). This property can be utilized to monitor hybridization of nucleic acids labeled at one end with a donor fluorophore (reporter) and at the opposite end with an acceptor (quencher) (Parkhurst et al., *Biochemistry* 1995, 34, 285-292). In the absence of a complementary target sequence the dual labeled probe is very flexible and undergoes rapid conformational changes so that the average distance between the donor (D) and acceptor (A) is close enough for efficient FRET to occur. Upon hybridization to complementary target, a rigid DNA duplex is formed separating the D-A pair and reducing the efficiency of transfer. This manifests itself in an increase in the fluorescence intensity of the reporter.

4.1 Synthesis and Characterization of BHQ Probes

To evaluate the efficiency of the Black Hole Quencher dyes (BHQs), the ability of these dyes to quench a series of common fluorophores was compared to the standard quencher dyes DABCYL and TAMRA in a complementation assay. As TAMRA exhibits its own native fluorescence, it can only be used to quench lower wavelength dyes and thus was only used to quench FAM in this assay.

4.1a Materials and Methods

Nucleic acids were synthesized on a Biosearch 8700 automated DNA synthesizer using standard phosphoramidite chemistry. $A^{BZ}$, $C_{AC}$, T, and $G^{DMF}$ phosphoramidites were supplied by Chruachem. TAMRA, DABCYL, and BHQ controlled pore glass (CPG) supports from Biosearch Technologies were used for attachment of quencher dyes to the 3' terminus of nucleic acids. 5' fluorophore labeling was accomplished using fluorophore phosphoramidites with the exception of Cy5 which was added as a succinimidyl ester to 5' amino nucleic acids using the manufacturers' protocol. 6-FAM and TFA-aminohexyl amidite were from Biosearch. Cy3 phosphoramidite and Cy5 succinimidyl ester were from Amersham Pharmacia Biotech. Cleavage and deprotection of oligos was carried out in ammonia at 60° C. for 3 hrs, with the exception of 3' TAMRA oligos which were deprotected in 1:3 t-butylamine:$H_2O$ for 8 hours at 60° C., and 3' BH3 oligos which were deprotected for 1 hour at 60° C. in ammonia. Following deprotection, dual labeled probes were evaporated to dryness then resuspended in HPLC grade water and filtered through 0.45 µM filters to prepare for HPLC purification. A two step method of HPLC purification of anion exchange followed by reverse phase HPLC was used to purify all dual labeled probes. Purified probes were analyzed by both anion exchange and reverse phase HPLC. Complementary nucleic acid was purified on a Biosearch Micropure II reverse phase cartridge using the standard protocol.

All fluorescence measurements were taken using a Spectramax Gemini fluorescent microplate reader. Probes were dissolved at 200 nM in a buffer composed of 10 mM Tris-HCl, 50 mM KCl, and 3.5 mM $MgCl_2$, pH 8.3, both in the presence and absence of a five fold excess of perfectly complimentary nucleic acid. Fluorescein was excited at 470 nm and emission was read at 530 nm with a 515 nm cutoff filter in place. Cy3 was excited at 510 nm and read at 567 nm with a 550 nm cutoff filter. Cy5 was excited at 630 nm and read at 660 nm with a 630 nm cutoff filter. Average fluorescent intensity from a set of eight buffer blanks was subtracted from all probe fluorescence measurements before calculation of signal to noise ratios.

The set of nucleic acids displayed in Table 2 was synthesized and rigorously purified by HPLC:

TABLE 2

Dual labeled probes prepared for hybridization assay.

| Reporter (5') | em max (nm) | Sequence (5' to 3') | Quencher (3') |
|---|---|---|---|
| FAM | 518 | ATG CCC TCC CCC ATG CCA TCC TGC G (SEQ ID NO.: 1) | TAMRA |
| FAM | 518 | ATG CCC TCC CCC ATG CCA TCC TGC G (SEQ ID NO.: 1) | DABCYL |
| FAM | 518 | ATG CCC TCC CCC ATG CCA TCC TGC G (SEQ ID NO.: 1) | BH1 |
| FAM | 518 | ATG CCC TCC CCC ATG CCA TCC TGC G (SEQ ID NO.: 1) | BH2 |

TABLE 2-continued

Dual labeled probes prepared for hybridization assay.

| Reporter (5') | em max (nm) | Sequence (5' to 3') | Quencher (3') |
|---|---|---|---|
| Cy3 | 573 | ATG CCC TCC CCC ATG CCA TCC TGC G (SEQ ID NO.: 1) | DABCYL |
| Cy3 | 573 | ATG CCC TCC CCC ATG CCA TCC TGC G (SEQ ID NO.: 1) | BH1 |
| Cy3 | 573 | ATG CCC TCC CCC ATG CCA TCC TGC G (SEQ ID NO.: 1) | BH2 |
| Cy5 | 678 | ATG CCC TCC CCC ATG CCA TCC TGC G (SEQ ID NO.: 1) | DABCYL |
| Cy5 | 678 | ATG CCC TCC CCC ATG CCA TCC TGC G (SEQ ID NO.: 1) | BH2 |
| Cy5 | 678 | ATG CCC TCC CCC ATG CCA TCC TGC G (SEQ ID NO.: 1) | BH3 |

The signal to noise ratio (S:N) of hybridization for each probe was measured in the presence of a five fold molar excess of perfectly complementary nucleic acid. All hybridization assays were performed in a buffer composed of 10 mM Tris-HCl, 50 mM KCl, and 3.5 mM $MgCl_2$, pH 8.3. S:N was calculated by dividing the fluorescence intensity of the probe in the presence of complement by the fluorescence intensity of the probe alone after subtracting out the fluorescence intensity of the buffer blank from each. All fluorescence measurements were taken in triplicate using a Spectramax Gemini fluorescent plate reader.

4.2 Results

Improved quenching by the BHQs was demonstrated for three widely separated fluorophores. A two fold increase in signal to noise ratio is achieved by replacing DABCYL with BH1 for the fluorescein probe. S:N increases are more striking for the cyanine dye labeled probes, with approximately a ten fold increase in S:N observed for the BH2 quenched Cy3 probe and a thirty fold S:N increase for the BH3 quenched Cy5 probe over identical structures quenched with DABCYL. This is consistant with the theory that efficiency of FRET is proportional to the magnitude of overlap between the donor and acceptor (Haugland et al., *Proc. Natl. Acad. Sci. U.S.A.* 1969, 63, 23-30). DABCYL, which absorbs maximally at 474 nm, quenches the red shifted reporter dyes with decreasing efficiency, whereas the BHQs can be chosen accordingly to have maximum spectral overlap with the reporter of interest.

Data from the hybridization assay is presented in Table 3.

TABLE 3

| Signal to noise ratios of dual labeled FRET probes | | | | | | | | | |
|---|---|---|---|---|---|---|---|---|---|
| donor/acceptor | Noise | | | Signal | | | Average | Average | |
| measurement no. | #1 | #2 | #3 | #1 | #2 | #3 | Noise | Signal | S:N |
| FAMTAM | 89.18 | 91.50 | 89.54 | 279.13 | 277.08 | 272.78 | 90.08 | 276.33 | 3.07 |
| FAMDAB | 89.97 | 81.03 | 86.74 | 348.98 | 323.82 | 352.00 | 85.92 | 341.61 | 3.98 |
| FAMBH1 | 39.24 | 37.05 | 38.85 | 296.53 | 316.24 | 311.15 | 38.38 | 307.97 | 8.02 |
| FAMBH2 | 67.12 | 66.64 | 56.79 | 445.48 | 415.78 | 442.75 | 63.52 | 434.34 | 6.84 |
| Cy3DAB | 19.66 | 19.65 | 19.39 | 147.70 | 139.83 | 154.35 | 19.57 | 147.29 | 7.53 |
| Cy3BH1 | 1.86 | 2.09 | 2.41 | 140.72 | 135.20 | 135.25 | 2.12 | 137.06 | 64.51 |
| Cy3BH2 | 2.02 | 1.94 | 2.08 | 149.65 | 148.89 | 150.40 | 2.02 | 149.65 | 74.15 |
| Cy5/DAB | 57.09 | 59.15 | 50.50 | 157.36 | 176.04 | 216.59 | 55.58 | 183.33 | 3.30 |
| Cy5/BH2 | 19.92 | 21.47 | 22.53 | 263.64 | 288.20 | 256.07 | 21.31 | 269.31 | 12.64 |
| Cy5/BH3 | 1.65 | 2.17 | 1.55 | 197.96 | 210.71 | 208.06 | 1.79 | 205.58 | 114.79 |

It is understood that the examples and embodiments described herein are for illustrative purposes only and that various modifications or changes in light thereof will be suggested to persons skilled in the art and are to included within the spirit and purview of this application and are considered within the scope of the appended claims. All publications, patents, and patent applications cited herein are hereby incorporated by reference in their entirety for all purposes.

What is claimed is:

1. A quencher of excited state energy having the structure:

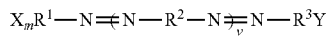

wherein
X and Y are members independently selected from reactive functional groups;
wherein at least one of X and Y is a substituted alkyl amine comprising a reactive functional group selected from carboxy, N-hydroxysuccinimide ester, N-hydroxybenztriazole ester, acid halide, acyl imidazole, thioester, p-nitrophenyl ester, alkenyl ester, alkynyl ester, aromatic ester, —NH$_2$, and phosphoramidite; or
at least one of X and Y is a substituted alkyl amine comprising a covalent bond to a solid support or to a nucleic acid;
m is a number selected from 0 to 4, inclusive, such that when m is greater than 1, the X groups are the same or different;
v is a number from 1 to 10 and when v is greater than 1, the R$^2$ groups are the same or different; and R$^1$, R$^2$, and R$^3$ are members independently selected from substituted or unsubstituted aryl, substituted or unsubstituted heteroaryl and substituted or unsubstituted unsaturated alkyl, with the proviso that at least two of R$^1$, R$^2$ and R$^3$ are members selected from substituted or unsubstituted aryl, substituted or unsubstituted heteroaryl and combinations thereof.

2. The quencher of excited state energy according to claim 1, wherein
at least one of X and Y is —NR'R", wherein R' and R" are members independently selected from unsubstituted alkyl and substituted alkyl,
with the proviso that at least one of R' and R" is selected such that it bears a reactive functional group selected from carboxy, N-hydroxysuccinimide ester, N-hydroxybenztriazole ester, acid halide, acyl imidazole, thioester, p-nitrophenyl ester, alkenyl ester, alkynyl ester, aromatic ester, —NH$_2$, and phosphoramidite, or at least one of R' and R" is covalently attached to a solid support or to a nucleic acid.

3. The quencher of excited state energy according to claim 2, wherein R' is unsubstituted alkyl; and R" is substituted alkyl.

4. The quencher of excited state energy according to claim 3, wherein R" is substituted C$_1$, C$_2$, C$_3$, C$_4$, C$_5$, or C$_6$ alkyl.

5. The quencher of excited state energy according to claim 3, wherein R" comprises a polyether.

6. The quencher of excited state energy according to claim 5, wherein said polyether is a member selected from poly (ethylene glycol), polypropylene glycol) and copolymers thereof.

7. The quencher of excited state energy according to claim 1, wherein said solid support is controlled pore glass (CPG).

8. A quencher of excited state energy having the structure:

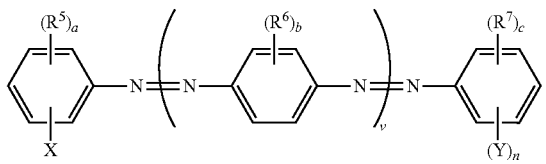

wherein
$R^5$, $R^6$ and $R^7$ are members independently selected from halogen, —NR'R", substituted or unsubstituted aryl, nitro, substituted or unsubstituted $C_1$-$C_6$ alkyl, and substituted or unsubstituted $C_1$-$C_6$ alkoxy,
  wherein R' and R" are independently selected from H and substituted or unsubstituted $C_1$-$C_6$ alkyl;
X is a substituted alkyl amine comprising a reactive functional group selected from carboxy, N-hydroxysuccinimide ester, N-hydroxybenztriazole ester, acid halide, acyl imidazole, thioester, p-nitrophenyl ester, alkenyl ester, alkynyl ester, aromatic ester, —$NH_2$, and phosphoramidite; or X is a substituted alkyl amine comprising a covalent bond to a solid support or to a nucleic acid;
Y is selected from the group consisting of reactive functional groups;
n is a number from 0 to 1, inclusive;
a is a number from 0 to 4, inclusive, such that when a is greater than 1, the $R^5$ groups are the same or different;
b is a number from 0 to 4, inclusive, such that when (v×b) is greater than 1, the $R^6$ groups are the same or different;
c is a number from 0 to 5, inclusive, such that when c is greater than 1, the $R^7$ groups are the same or different; and
v is a number from 1 to 10, inclusive, such that when v is greater than 1, the value of b on each of the v phenyl rings is the same or different.

9. The quencher of excited state energy according to claim 8, wherein
X is —NR'R", wherein, for X, R' and R" are members independently selected from unsubstituted alkyl and substituted alkyl,
  with the proviso that, for X, at least one of R' and R" is selected such that it bears a reactive functional group selected from carboxy, N-hydroxysuccinimide ester, N-hydroxybenztriazole ester, acid halide, acyl imidazole, thioester, p-nitrophenyl ester, alkenyl ester, alkynyl ester, aromatic ester, —$NH_2$, and phosphoramidite, or at least one of R' and R" is covalently attached to a solid support or to a nucleic acid.

10. The quencher of excited state energy according to claim 9, having the structure:

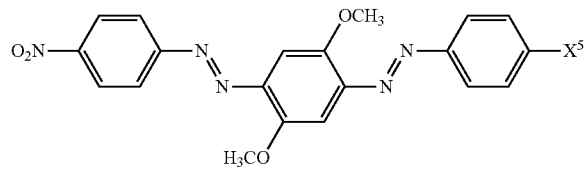

wherein $X^5$ is —NR'R",
  wherein R' and R" are members independently selected from unsubstituted alkyl and substituted alkyl,
    with the proviso that at least one of R' and R" is selected such that it bears a reactive functional group selected from carboxy, N-hydroxysuccinimide ester, N-hydroxybenztriazole ester, acid halide, acyl imidazole, thioester, p-nitrophenyl ester, alkenyl ester, alkynyl ester, aromatic ester, —$NH_2$, and phosphoramidite, or at least one of R' and R" is covalently attached to a solid support or to a nucleic acid.

11. The quencher of excited state energy according to claim 9, wherein R' is unsubstituted alkyl; and R" is substituted alkyl.

12. The quencher of excited state energy according to claim 11, wherein R" is substituted $C_1$, $C_2$, $C_3$, $C_4$, $C_5$, or $C_6$ alkyl.

13. The quencher of excited state energy according to claim 11, wherein R" comprises a polyether.

14. The quencher of excited state energy according to claim 13, wherein said polyether is a member selected from poly(ethylene glycol), polypropylene glycol) and copolymers thereof.

15. The quencher of excited state energy according to claim 8, wherein said solid support is controlled pore glass (CPG).

16. A quencher of excited state energy having the structure:

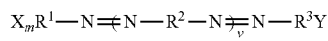

wherein
X and Y are members independently selected from reactive functional groups;
  wherein at least one of X and Y is —NR'R", wherein R' is unsubstituted alkyl; and R" is substituted $C_1$, $C_3$, $C_4$, $C_5$, or $C_6$ alkyl bearing a reactive functional group;
m is a number selected from 0 to 4, inclusive, such that when m is greater than 1, the X groups are the same or different;
v is a number from 1 to 10 and when v is greater than 1, the $R^2$ groups are the same or different; and
$R^1$, $R^2$, and $R^3$ are members independently selected from substituted or unsubstituted aryl, substituted or unsubstituted heteroaryl and substituted or unsubstituted unsaturated alkyl, with the proviso that at least two of $R^1$, $R^2$ and $R^3$ are members selected from substituted or unsubstituted aryl, substituted or unsubstituted heteroaryl and combinations thereof.

17. The quencher of excited state energy according to claim 16, wherein R" bears a reactive functional group selected from carboxy, N-hydroxysuccinimide ester, N-hydroxybenztriazole ester, acid halide, acyl imidazole, thioester, p-nitrophenyl ester, alkyl ester, alkenyl ester, alkynyl ester, aromatic ester, hydroxy, —$NH_2$, and phosphoramidite.

18. A quencher of excited state energy having the structure:

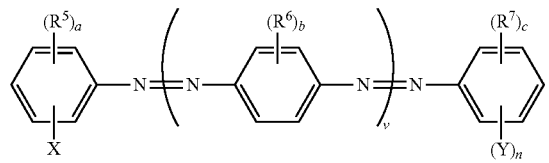

wherein
R[5], R[6] and R[7] are members independently selected from halogen, —NR'R", substituted or unsubstituted aryl, nitro, substituted or unsubstituted $C_1$-$C_6$ alkyl, and substituted or unsubstituted $C_1$-$C_6$ alkoxy,
wherein R' and R" are independently selected from H and substituted or unsubstituted $C_1$-$C_6$ alkyl;
X is —NR'R", wherein, for X, R' is unsubstituted alkyl; and R" is substituted $C_1$, $C_3$, $C_4$, $C_5$, or $C_6$ alkyl bearing a reactive functional group;
Y is selected from the group consisting of reactive functional groups;
n is a number from 0 to 1, inclusive;
a is a number from 0 to 4, inclusive, such that when a is greater than 1, the R[5] groups are the same or different;
b is a number from 0 to 4, inclusive, such that when (v×b) is greater than 1, the R[6] groups are the same or different;
c is a number from 0 to 5, inclusive, such that when c is greater than 1, the R[7] groups are the same or different; and
v is a number from 1 to 10, inclusive, such that when v is greater than 1, the value of b on each of the v phenyl rings is the same or different.

19. The quencher of excited state energy according to claim 18, having the structure:

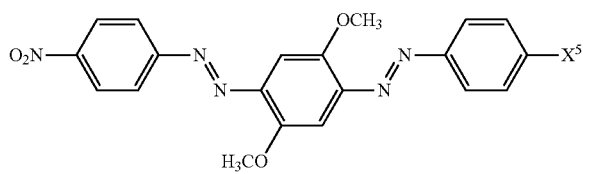

wherein $X^5$ is —NR'R",
wherein
R' is unsubstituted alkyl; and
R" is substituted $C_1$, $C_3$, $C_4$, $C_5$, or $C_6$ alkyl bearing a reactive functional group.

20. The quencher of excited state energy according to claim 18, wherein, for X, R" bears a reactive functional group selected from carboxy, N-hydroxysuccinimide ester, N-hydroxybenztriazole ester, acid halide, acyl imidazole, thioester, p-nitrophenyl ester, alkyl ester, alkenyl ester, alkynyl ester, aromatic ester, hydroxy, —NH$_2$, and phosphoramidite.

21. A quencher of excited state energy having the structure:

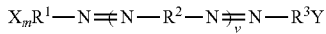

wherein
X and Y are members independently selected from reactive functional groups;
wherein at least one of X and Y is

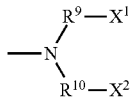

wherein
R[9] is unsubstituted alkyl;
R[10] is substituted alkyl;
$X^1$ is —CH$_3$; and
$X^2$ is a member selected from —OH, —COOH, —NH$_2$, —SH, and —OP(OX$^3$)N(X$^4$)$_2$,
wherein X$^3$ and X$^4$ are members independently selected from alkyl and substituted alkyl;
m is a number selected from 0 to 4, inclusive, such that when m is greater than 1, the X groups are the same or different;
v is a number from 1 to 10 and when v is greater than 1, the R[2] groups are the same or different; and
R[1], R[2], and R[3] are members independently selected from substituted or unsubstituted aryl, substituted or unsubstituted heteroaryl and substituted or unsubstituted unsaturated alkyl, with the proviso that at least two of R[1], R[2] and R[3] are members selected from substituted or unsubstituted aryl, substituted or unsubstituted heteroaryl and combinations thereof.

22. The quencher of excited state energy according to claim 21, wherein X$^3$ is cyanoethyl; and X$^4$ is isopropyl.

23. The quencher of excited state energy according to claim 21, wherein R[10] comprises a polyether.

24. The quencher of excited state energy according to claim 23, wherein said polyether is a member selected from poly (ethylene glycol), polypropylene glycol) and copolymers thereof.

25. A quencher of excited state energy having the structure:

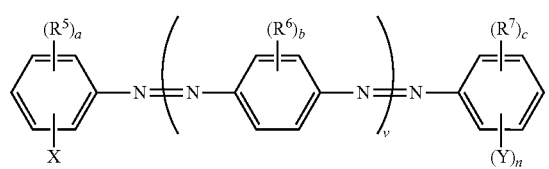

wherein
R[5], R[6] and R[7] are members independently selected from halogen, —NR'R", substituted or unsubstituted aryl, nitro, substituted or unsubstituted $C_1$-$C_6$ alkyl, and substituted or unsubstituted $C_1$-$C_6$ alkoxy,
wherein R' and R" are independently selected from H and substituted or unsubstituted $C_1$-$C_6$ alkyl;
X is

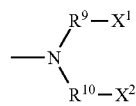

wherein
R[9] is unsubstituted alkyl;
R[10] is substituted alkyl;
$X^1$ is —CH$_3$; and
$X^2$ is a member selected from —OH, —COOH, —NH$_2$, —SH, and —OP(OX$^3$)N(X$^4$)$_2$,
wherein X$^3$ and X$^4$ are members independently selected from alkyl and substituted alkyl;
Y is selected from the group consisting of reactive functional groups;
n is a number from 0 to 1, inclusive;
a is a number from 0 to 4, inclusive, such that when a is greater than 1, the R[5] groups are the same or different;
b is a number from 0 to 4, inclusive, such that when (v×b) is greater than 1, the R[6] groups are the same or different;

c is a number from 0 to 5, inclusive, such that when c is greater than 1, the $R^7$ groups are the same or different; and v is a number from 1 to 10, inclusive, such that when v is greater than 1, the value of b on each of the v phenyl rings is the same or different.

26. The quencher of excited state energy according to claim 25, having the structure:

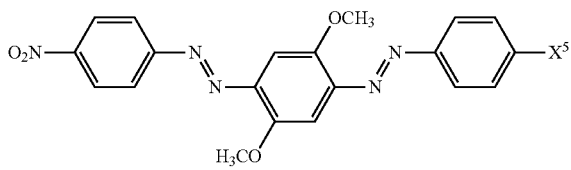

wherein $X^5$ is

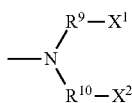

wherein
$R^9$ is unsubstituted alkyl;
$R^{10}$ is substituted alkyl;
$X^1$ is —$CH_3$; and
$X^2$ is a member selected from —OH, —COOH, —$NH_2$, —SH, and —OP($OX^3$)N($X^4$)$_2$,
wherein $X^3$ and $X^4$ are members independently selected from alkyl and substituted alkyl.

27. The quencher of excited state energy according to claim 25, wherein $X^3$ is cyanoethyl; and $X^4$ is isopropyl.

28. The quencher of excited state energy according to claim 25, wherein $R^{10}$ comprises a polyether.

29. The quencher of excited state energy according to claim 28, wherein said polyether is a member selected from poly(ethylene glycol), poly(propylene glycol) and copolymers thereof.

30. A quencher of excited state energy having the structure:

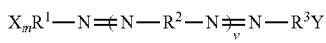

wherein
X and Y are members independently selected from reactive functional groups;
wherein at least one of X and Y is

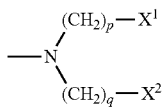

wherein
$X^1$ is —$CH_3$;
$X^2$ is a member selected from —COOH, —$NH_2$, —SH, and —OP($OX^3$)N($X^4$)$_2$,
wherein $X^3$ and $X^4$ are members independently selected from alkyl and substituted alkyl;
p is a number selected from 1, 2, 3, 4, 5, 6, 7, 8, 9, 10, 11, 12, 13, 14, 15, 16, 17, 18, 19, and 20; and q is a number selected from 1, 2, 3, 4, 5, 6, 7, 8, 9, 10, 11, 12, 13, 14, 15, 16, 17, 18, 19, and 20;
m is a number selected from 0 to 4, inclusive, such that when m is greater than 1, the X groups are the same or different;
v is a number from 1 to 10 and when v is greater than 1, the $R^2$ groups are the same or different; and
$R^1$, $R^2$, and $R^3$ are members independently selected from substituted or unsubstituted aryl, substituted or unsubstituted heteroaryl and substituted or unsubstituted unsaturated alkyl, with the proviso that at least two of $R^1$, $R^2$ and $R^3$ are members selected from substituted or unsubstituted aryl, substituted or unsubstituted heteroaryl and combinations thereof.

31. The quencher of excited state energy according to claim 30, wherein $X^3$ is cyanoethyl; and $X^4$ is isopropyl.

32. A quencher of excited state energy having the structure:

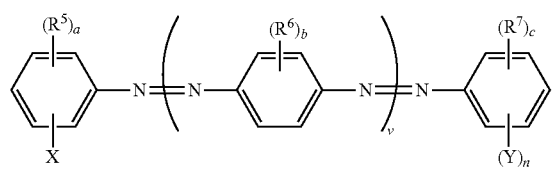

wherein
$R^5$, $R^6$ and $R^7$ are members independently selected from halogen, —NR'R", substituted or unsubstituted aryl, nitro, substituted or unsubstituted $C_1$-$C_6$ alkyl, and substituted or unsubstituted $C_1$-$C_6$ alkoxy,
wherein R' and R" are independently selected from H and substituted or unsubstituted $C_1$-$C_6$ alkyl;
X is

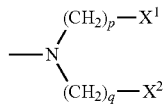

wherein
$X^1$ is —$CH_3$;
$X^2$ is a member selected from —COOH, —$NH_2$, —SH, and —OP($OX^3$)N($X^4$)$_2$,
wherein $X^3$ and $X^4$ are members independently selected from alkyl and substituted alkyl;
p is a number selected from 1, 2, 3, 4, 5, 6, 7, 8, 9, 10, 11, 12, 13, 14, 15, 16, 17, 18, 19, and 20; and
q is a number selected from 1, 2, 3, 4, 5, 6, 7, 8, 9, 10, 11, 12, 13, 14, 15, 16, 17, 18, 19, and 20;
Y is selected from the group consisting of reactive functional groups;
n is a number from 0 to 1, inclusive;
a is a number from 0 to 4, inclusive, such that when a is greater than 1, the $R^5$ groups are the same or different;
b is a number from 0 to 4, inclusive, such that when (v×b) is greater than 1, the $R^6$ groups are the same or different;
c is a number from 0 to 5, inclusive, such that when c is greater than 1, the $R^7$ groups are the same or different; and
v is a number from 1 to 10, inclusive, such that when v is greater than 1, the value of b on each of the v phenyl rings is the same or different.

33. The quencher of excited state energy according to claim 32, having the structure:

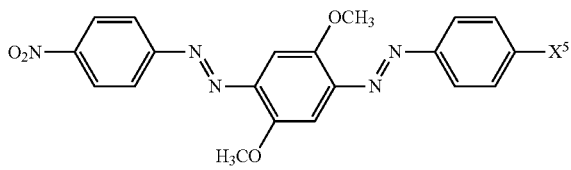

wherein $X^5$ is

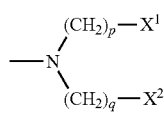

wherein
$X^1$ is —$CH_3$;
$X^2$ is a member selected from —COOH, —$NH_2$, —SH, and —OP(O$X^3$)N($X^4$)$_2$,
wherein $X^3$ and $X^4$ are members independently selected from alkyl and substituted alkyl;
p is a number selected from 1, 2, 3, 4, 5, 6, 7, 8, 9, 10, 11, 12, 13, 14, 15, 16, 17, 18, 19, and 20; and
q is a number selected from 1, 2, 3, 4, 5, 6, 7, 8, 9, 10, 11, 12, 13, 14, 15, 16, 17, 18, 19, and 20.

34. The quencher of excited state energy according to claim 32, wherein $X^3$ is cyanoethyl; and $X^4$ is isopropyl.

35. A quencher of excited state energy having the structure:

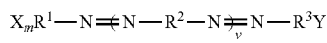

wherein
X and Y are members independently selected from reactive functional groups;
wherein at least one of X and Y is

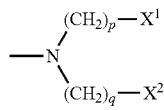

wherein
$X^1$ is —$CH_3$;
$X^2$ is a member selected from —OH, —COOH, —$NH_2$, —SH, and —OP(O$X^3$)N($X^4$)$_2$,
wherein $X^3$ and $X^4$ are members independently selected from alkyl and substituted alkyl;
p is a number selected from 1, 2, 3, 4, 5, 6, 7, 8, 9, 10, 11, 12, 13, 14, 15, 16, 17, 18, 19, and 20; and
q is a number selected from 1, 3, 4, 5, 6, 7, 8, 9, 10, 11, 12, 13, 14, 15, 16, 17, 18, 19, and 20;
m is a number selected from 0 to 4, inclusive, such that when m is greater than 1, the X groups are the same or different;
v is a number from 1 to 10 and when v is greater than 1, the $R^2$ groups are the same or different; and
$R^1$, $R^2$, and $R^3$ are members independently selected from substituted or unsubstituted aryl, substituted or unsubstituted heteroaryl and substituted or unsubstituted unsaturated alkyl, with the proviso that at least two of $R^1$, $R^2$ and $R^3$ are members selected from substituted or unsubstituted aryl, substituted or unsubstituted heteroaryl and combinations thereof.

36. The quencher of excited state energy according to claim 35, wherein $X^3$ is cyanoethyl; and $X^4$ is isopropyl.

37. A quencher of excited state energy having the structure:

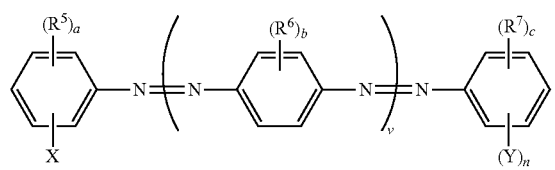

wherein
$R^5$, $R^6$ and $R^7$ are members independently selected from halogen, —NR'R", substituted or unsubstituted aryl, nitro, substituted or unsubstituted $C_1$-$C_6$ alkyl, and substituted or unsubstituted $C_1$-$C_6$ alkoxy,
wherein R' and R" are independently selected from H and substituted or unsubstituted $C_1$-$C_6$ alkyl;

X is

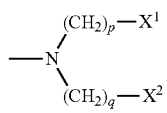

wherein
$X^1$ is —$CH_3$;
$X^2$ is a member selected from —OH, —COOH, —$NH_2$, —SH, and —OP(O$X^3$)N($X^4$)$_2$,
wherein $X^3$ and $X^4$ are members independently selected from alkyl and substituted alkyl;
p is a number selected from 1, 2, 3, 4, 5, 6, 7, 8, 9, 10, 11, 12, 13, 14, 15, 16, 17, 18, 19, and 20; and
q is a number selected from 1, 3, 4, 5, 6, 7, 8, 9, 10, 11, 12, 13, 14, 15, 16, 17, 18, 19, and 20;
Y is selected from the group consisting of reactive functional groups;
n is a number from 0 to 1, inclusive;
a is a number from 0 to 4, inclusive, such that when a is greater than 1, the $R^5$ groups are the same or different;
b is a number from 0 to 4, inclusive, such that when (v×b) is greater than 1, the $R^6$ groups are the same or different;
c is a number from 0 to 5, inclusive, such that when c is greater than 1, the $R^7$ groups are the same or different; and
v is a number from 1 to 10, inclusive, such that when v is greater than 1, the value of b on each of the v phenyl rings is the same or different.

38. The quencher of excited state energy according to claim 37, having the structure:

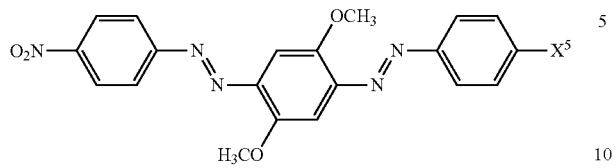

wherein $X^5$ is

wherein
$X^1$ is —$CH_3$;
$X^2$ is a member selected from —OH, —COOH, —$NH_2$, —SH, and —OP(O$X^3$)N($X^4$)$_2$,
  wherein $X^3$ and $X^4$ are members independently selected from alkyl and substituted alkyl;
p is a number selected from 1, 2, 3, 4, 5, 6, 7, 8, 9, 10, 11, 12, 13, 14, 15, 16, 17, 18, 19, and 20; and
q is a number selected from 1, 3, 4, 5, 6, 7, 8, 9, 10, 11, 12, 13, 14, 15, 16, 17, 18, 19, and 20.

39. The quencher of excited state energy according to claim 37, wherein $X^3$ is cyanoethyl; and $X^4$ is isopropyl.

* * * * *

```
SEQUENCE LISTING

<160> NUMBER OF SEQ ID NOS: 1

<210> SEQ ID NO 1
<211> LENGTH: 25
<212> TYPE: DNA
<213> ORGANISM: Artificial Sequence
<220> FEATURE:
<223> OTHER INFORMATION: probe synthetic

<400> SEQUENCE: 1
atgccctccc ccatgccatc ctgcg                                      25
```